(12) United States Patent
Huc et al.

(10) Patent No.: US 9,868,809 B2
(45) Date of Patent: Jan. 16, 2018

(54) METHOD FOR THE HIGH-YIELD PRODUCTION OF GIANT P-(R)CALIXARENES

(71) Applicant: UNIVERSITE PARIS-SUD XI, Orsay (FR)

(72) Inventors: Vincent Germain Huc, Orsay (FR); Cyril Martini, Bures sur Yvette (FR)

(73) Assignee: UNIVERSITE PARIS-SUD XI, Orsay (FR)

( * ) Notice: Subject to any disclaimer, the term of this patent is extended or adjusted under 35 U.S.C. 154(b) by 114 days.

(21) Appl. No.: 14/424,115

(22) PCT Filed: Aug. 28, 2013

(86) PCT No.: PCT/FR2013/051989
§ 371 (c)(1),
(2) Date: May 6, 2015

(87) PCT Pub. No.: WO2014/033407
PCT Pub. Date: Mar. 6, 2014

(65) Prior Publication Data
US 2015/0232603 A1    Aug. 20, 2015

(30) Foreign Application Priority Data
Aug. 28, 2012 (FR) ...................... 12 58054

(51) Int. Cl.
*C08G 14/02*  (2006.01)
*C08G 8/20*   (2006.01)
*C08G 8/08*   (2006.01)
*C07C 39/16*  (2006.01)
*C07C 39/17*  (2006.01)

(52) U.S. Cl.
CPC ............... *C08G 8/20* (2013.01); *C07C 39/16* (2013.01); *C07C 39/17* (2013.01); *C08G 8/08* (2013.01)

(58) Field of Classification Search
CPC . C08J 3/11; C08J 5/24; C08J 2361/06; C08G 8/10; C08L 9/00; C08L 61/06; C08L 21/00; C08L 2666/16; C08K 5/09
See application file for complete search history.

(56) References Cited

FOREIGN PATENT DOCUMENTS

| | | | |
|---|---|---|---|
| CA | 2251070 A1 | 4/1996 | |
| EP | 1361208 A1 | 11/2013 | |
| FR | 2795077 A1 | 12/2000 | |
| JP | 2008-214520 | * 9/2008 | ................ C08J 5/22 |

OTHER PUBLICATIONS

Alessandro Casnati et al, (Benzyloxy)calix[8]arene: One-Pot Synthesis and Functionalization, The Journal of Organic Chemi Stry, vol. 62, No. 18, Sep. 1, 1997 (Sep. 1, 1997), pp. 6236-6239.

(Continued)

*Primary Examiner* — Shane Fang
(74) *Attorney, Agent, or Firm* — Young & Thompson

(57) ABSTRACT

Giant p-(R)calixarenes, a process for the preparation of giant p-(R)calixarenes with high yields, and their use as the constitution of a material or in the context of the reinforcement of the material.

10 Claims, 36 Drawing Sheets

(56) References Cited

OTHER PUBLICATIONS

Vincent Huc et al: "C 3 V (Trimethyl) p-(Benzyloxy)calix[6]arene: A Versatile Platform for the Synthesis of Functionalized C 3 v Calix[6]arenes", European Journal of Organic Chemistry, vol. 2010, No. 11, Apr. 1, 2010, pp. 2199-2205.
C David Gutsche et al: "Calixarenes: paradoxes and paradigms in molecular baskets", Pure & Applied Chemistry, vol. 1. 62, No. 3, Jan. 1, 1990 (Jan. 1, 1990), pp. 485-491.
Ostaszewski R et al: "Influence of Base and Solvent on the Reaction between p-Cresol and Formaldehyde Leading to p-Methalcalix(n)arenes", Polish Journal of Chemistry, Polskie Towarzystwo Chemiczne, PL, vol. 1. 71, No. 8, Jan. 1, 1997 (Jan. 1, 1997), pp. 1053-1059.
Bernd Garska et al: "Molecular Reinforcement of Transparent Materials With Acrylamide-Modified Calix[4]arene as a Crosslinker", Macromolecular Materials and Engineering, va 1. 297, No. 8, Feb. 10, 2012 (Feb. 10, 2012), pp. 785-789.
Nakayama T et al: "New Positive-Type Photoresist Based on Mono-Substituted Hydroquinone Calix (8) Arene and Diazonaphthoquinone", Journal of Materials Chemistry, Royal Society of Chemistry, GB, vol. 9, No. 3, Mar. 1, 1999 (Mar. 1, 1999), pp. 697-702.
Database Registry [Online], Chemical Abstracts Service, Columbus, Ohio, US; Apr. 26, 2004 (Apr. 26, 2004), XP002694618.
Database chemcats [Online], Chemical Abstracts Service, Columbus, Ohio, US; Aug. 21, 2012 (Aug. 21, 2012), XP002694619.
Roger Lamartine et al: Solid State Polycondensation of Precursors of Phenolic Resins II, Molecular Crystals and Liquid Crystals, vol. 134, No. I, Apr. 1, 1986 (Apr. 1, 1986), pp. 219-236, XP55058975.
Takeharu Haino et al: "Synthesis and binding behavior of an artificial receptor based on "upper rim" functionalized ca 1 i x [5] arene", Tetrahedron, vo 1. 54, No. 40, Oct. 1, 1998 (Oct. 1, 1998), pp. 12185-12196, XP55058970.
Tyo Sone: "Inclusion Properties of Acyclic P-Substituted Phenol-Formaldehyde Oligomers", Bulletin of the Chemical Society of Japan, vo 1. 62, No. 4, Jan. 1, 1989 (Jan. 1, 1989), pp. 1111-1116.
Choi Sung-Seen: "Properties of butyl rubber vulcanizates cured by different type resoles", Polymer (Korea) Department of Chemical Engineering, Sogon University; Seoul, Korea, vol. 7, No. 3, Jan. 1, 1999 (Jan. 1, 1999), pp. 172-180.

* cited by examiner

Figure 21.1 : Fraction F0

Figure 21.2 : Fraction P3

Figure 21.3 : Fraction F5

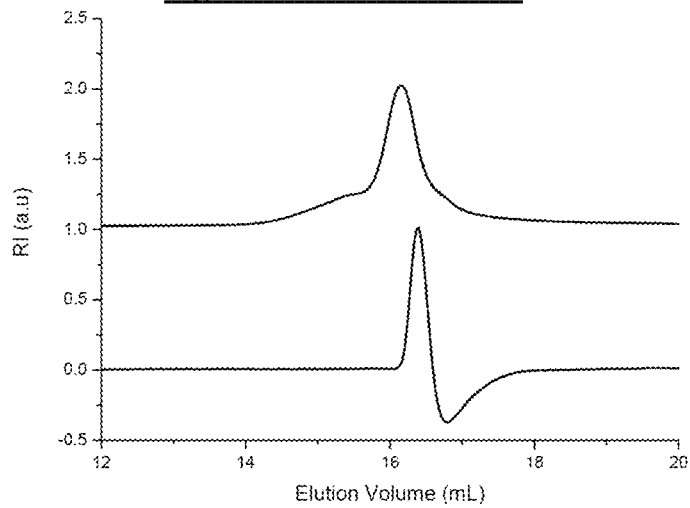
Figure 21.4 : Fraction P12
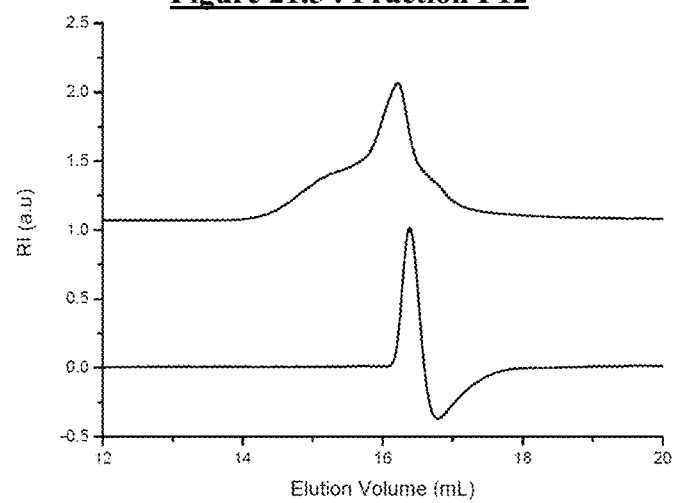
Figure 21.5 : Fraction F12
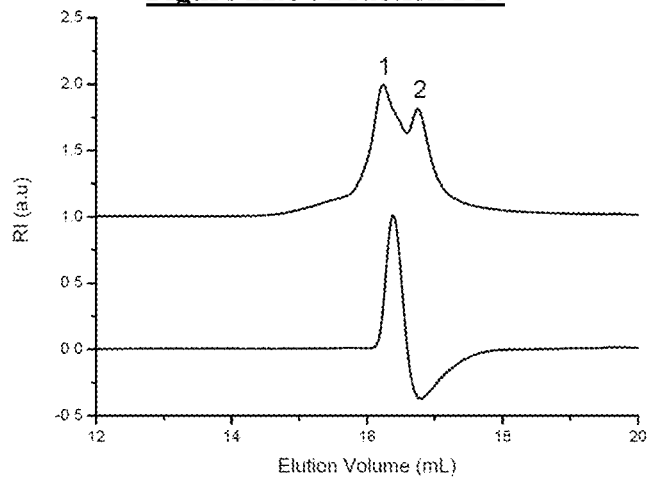
Figure 21.6 : Fraction P14

Figure 21.7 : Fraction F14
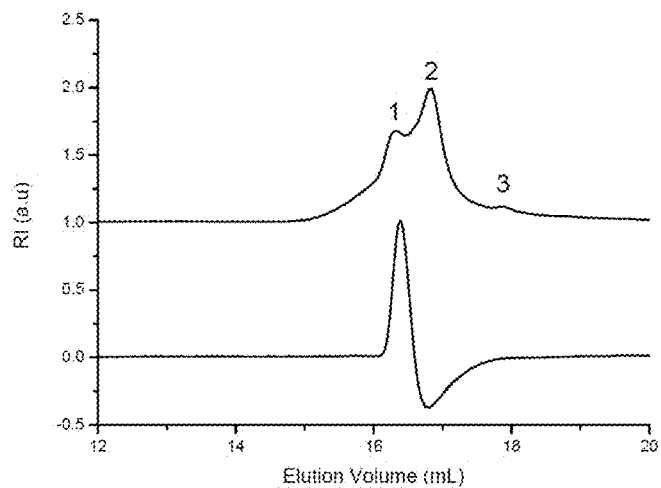
Figure 21.8 : Fraction P15
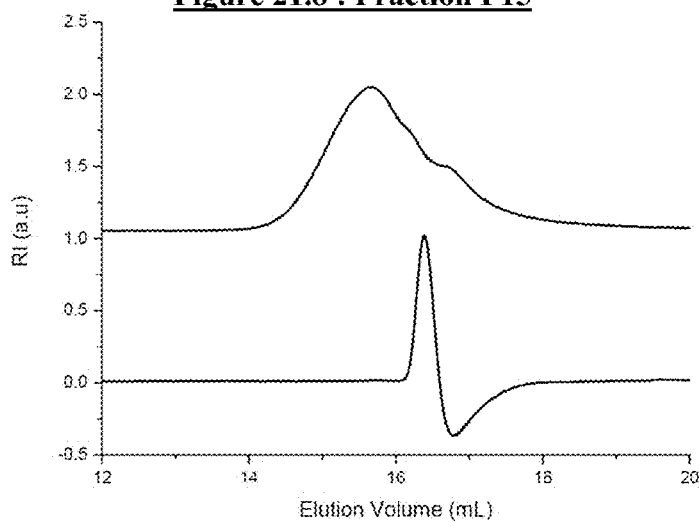
Figure 21.9 : Fraction P16
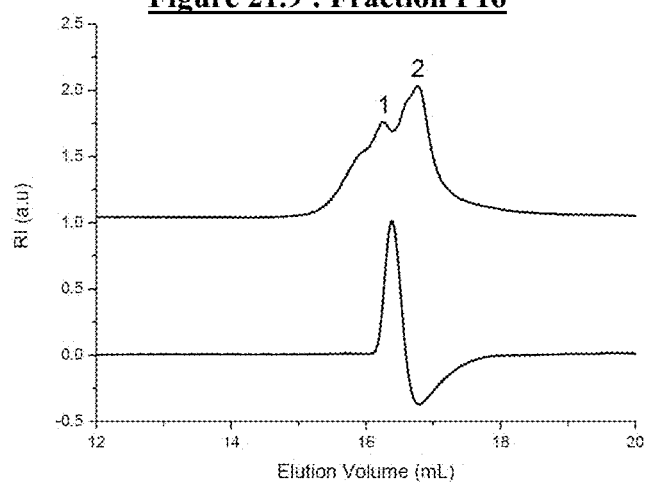

Figure 22.1 : Fraction F6b (Calix[9]arene)

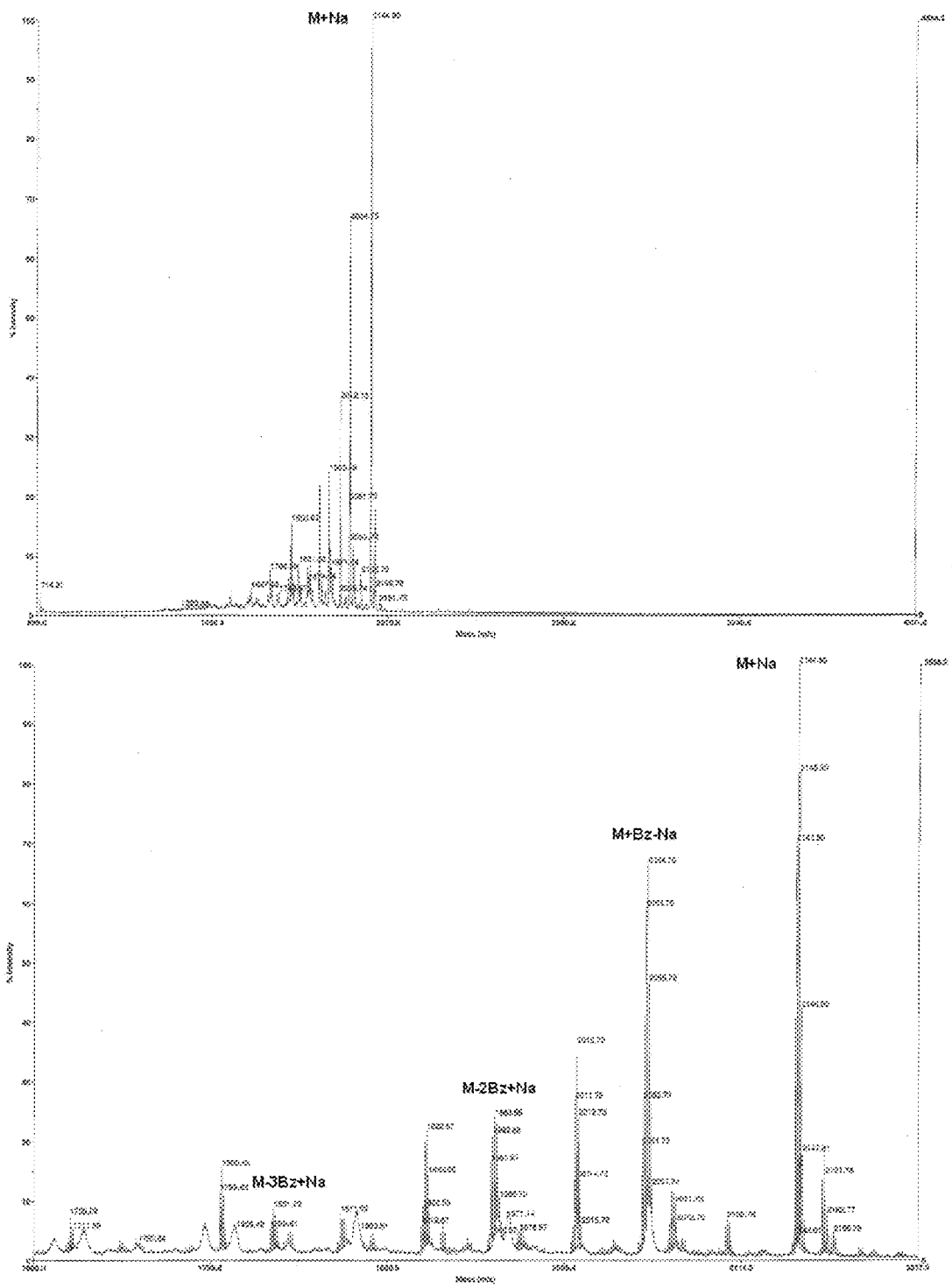
Figure 22.2 : Fraction P7 (Calix[10]arene)

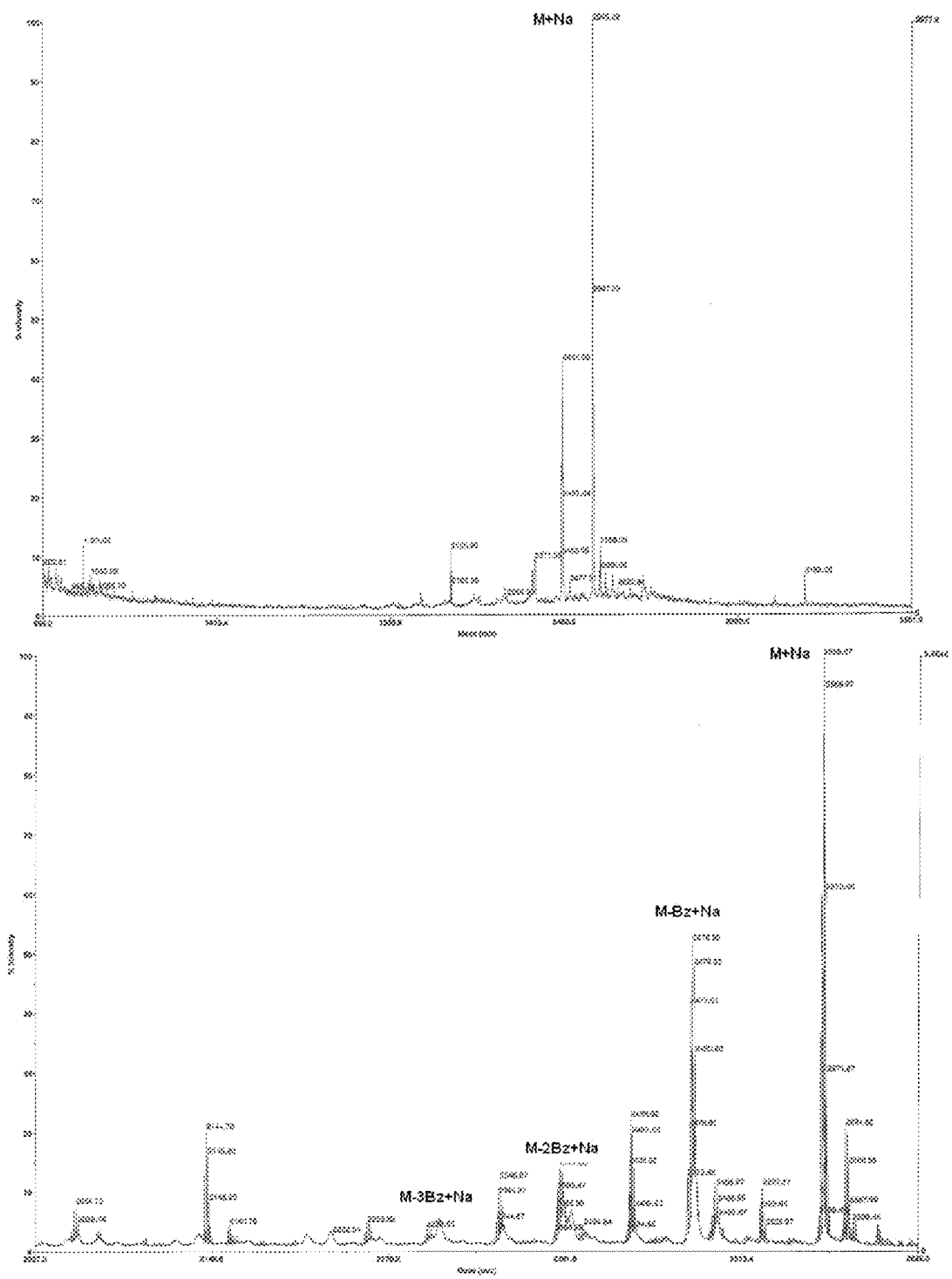
Figure 22.3 : Fraction P10 (Calix[12]arene)

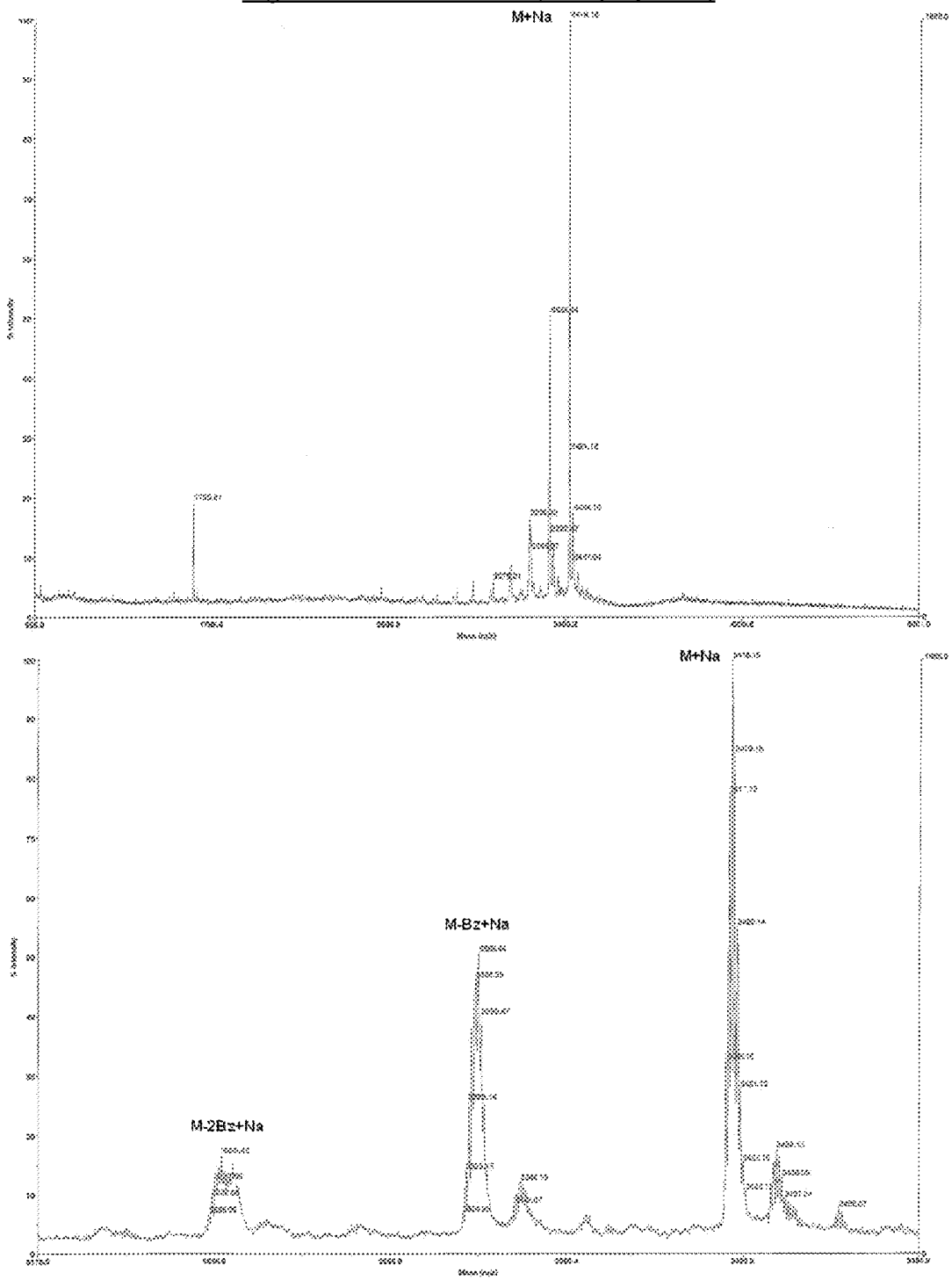
Figure 22.4 : Fraction P4 (calix[16]arene)

Figure 23.1 : Fraction F6b (Calix[9]arene)

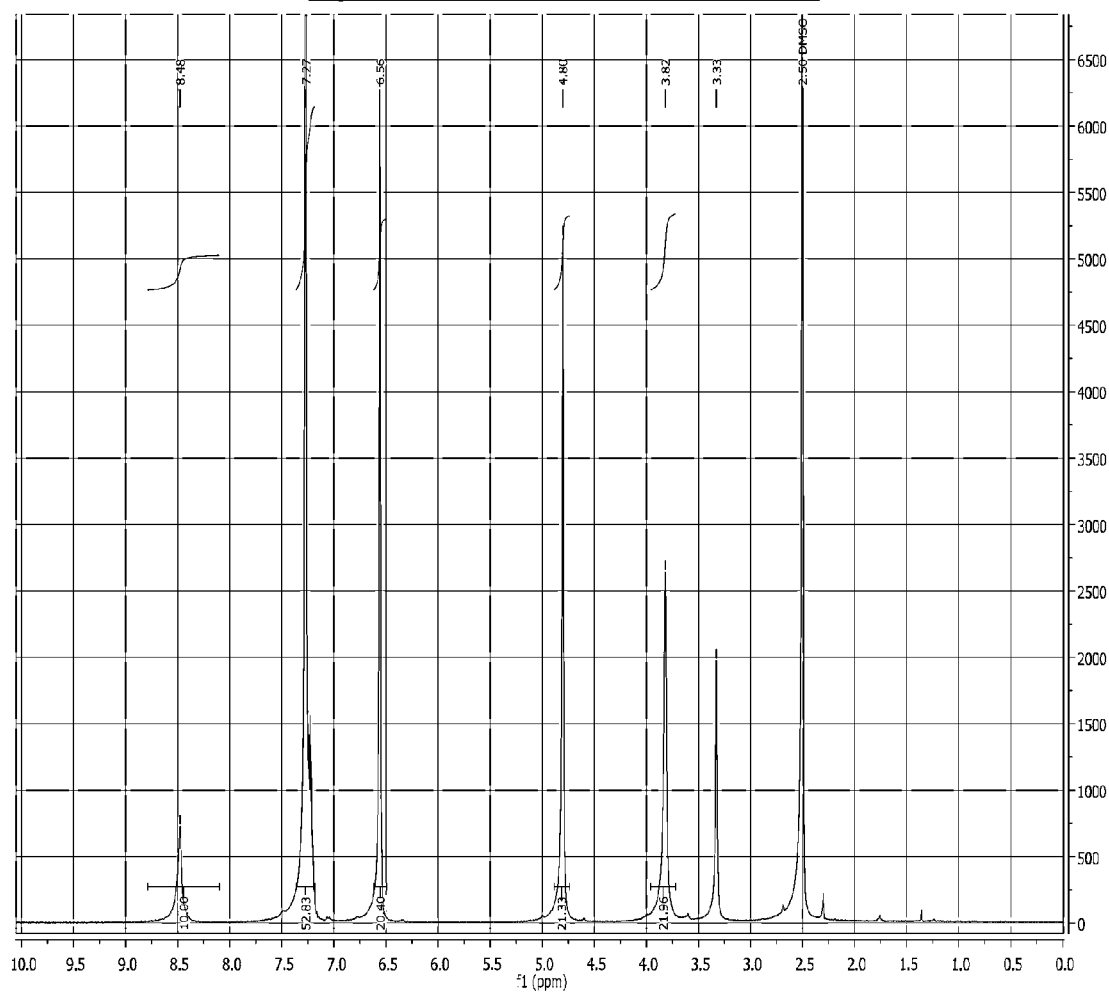
Figure 23.2 : Fraction P7 (Calix[10]arene)

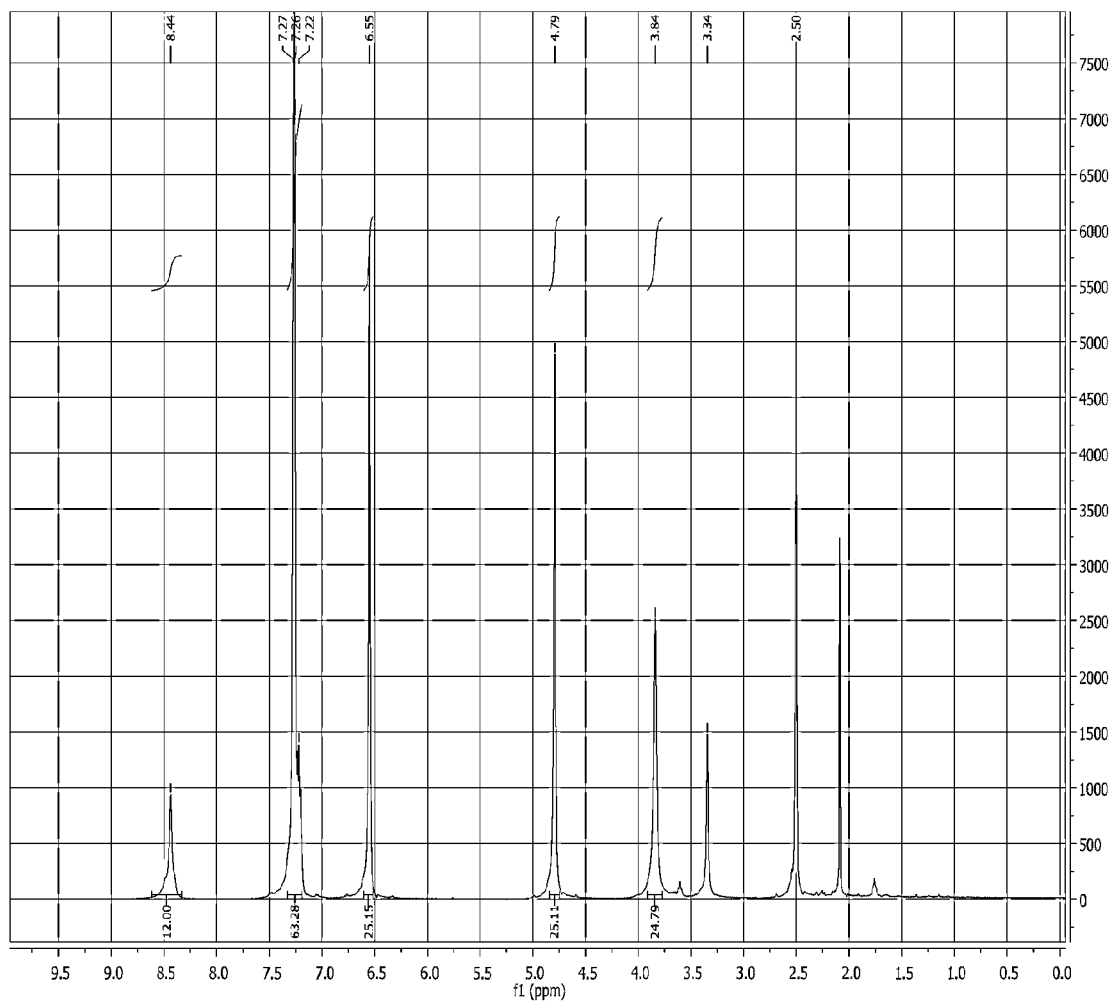
Figure 23.3 : Fraction P10 (Calix[12]arene)

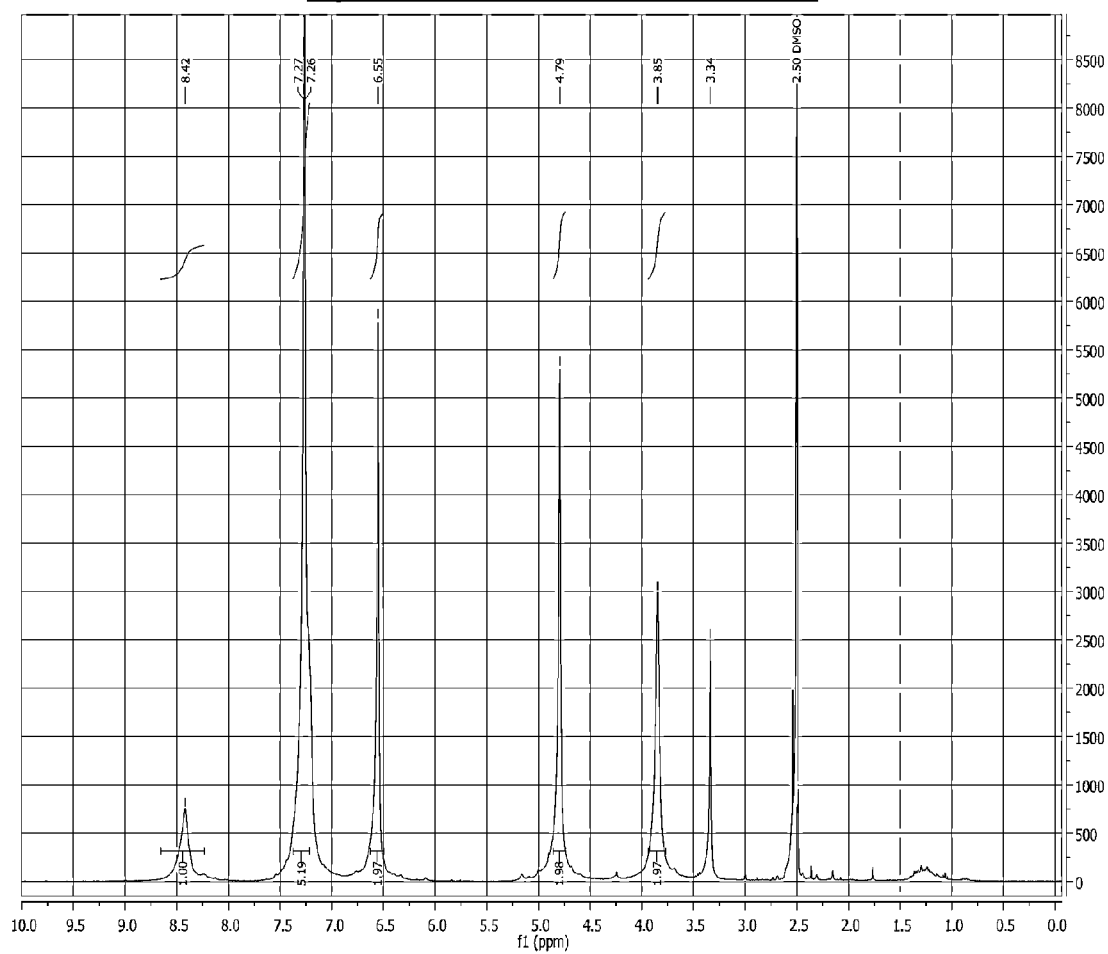
Figure 23.4 : Fraction F16 (calix[13]arene)

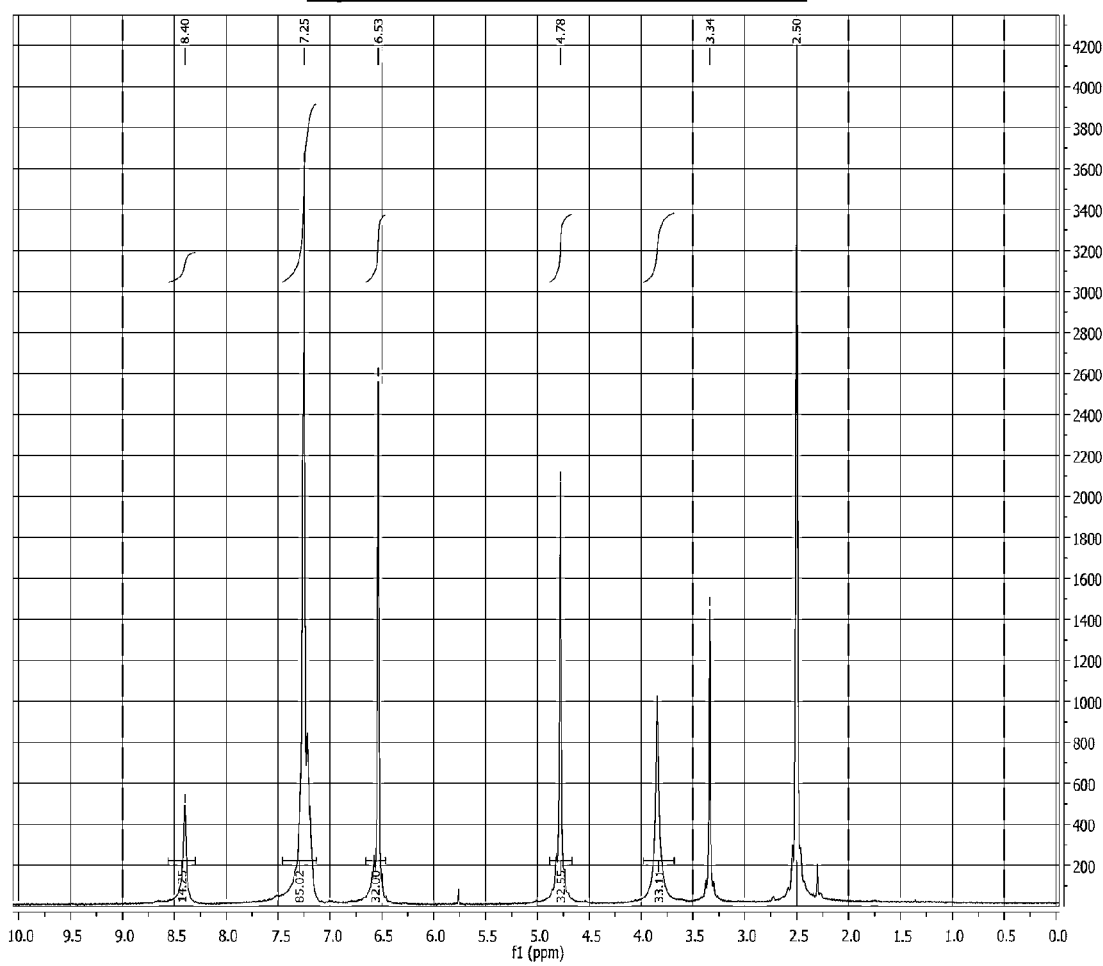
Figure 23.5 : Fraction P4 (calix[16]arene)

METHOD FOR THE HIGH-YIELD PRODUCTION OF GIANT P-(R)CALIXARENES

The present invention relates to a process for the high-yield preparation of giant p-(R)calixarenes.

The calixarenes have been the subject of particular study in the last ten years owing to the immense possibilities offered by these easily accessible macrocycles. These macrocycles are cup-shaped, the cavity generally being less than or equal to approximately 1 nm.

Some of the properties most studied include the phenomena of recognition of the ions and/or molecules, the supramolecular assemblies or also the synthesis of nanoparticles, among other things.

In most cases, these studies were carried out with calixarenes functionalized with a p-(t-butyl) or with calixarenes obtained by chemical modification of these p-(t-butyl)calixarenes, since the synthesis of p-(t-butyl)calixarenes is by far the most documented since the pioneering work of Gutsche et al.

D. Gutsche, *Calixarenes: An Introduction*, The Royal Society of Chemistry, Cambridge, 2008.

Z. Asfari, V. Böhmer, J. Harrowfield, J. Vicens, *Calixarenes 2001*, Kluwer, Dordrecht, the Netherlands, 2001.

Consequently, the use of other monomers of the functionalized phenol type for synthesis of calixarenes is largely unexplored, even if one-stage syntheses of other p-(alkyl) calixarenes are known (T. Patrick, R Egan, *J. Org. Chem.* 1977, 42, 382; T. Patrick, P. Egan, *J. Org. Chem.* 1978, 43, 4280; Z. Asfari, J. Vicens, *Tetrahedron Lett.* 1988, 29, 2659; F. Vocanson, M. Perrin, R. Lamartine, *J. Inclusion Phenom. Macrocyclic Chem.* 2001, 39, 127; Jerry L. Atwood et al.; *Org. Lett.* 1999, 1, 1523).

The p-substituted calixarenes are usually obtained in a mixture of p-calix[4, 5, 6, 7, 8]arenes by reaction of a p-substituted phenol with paraformaldehyde in the presence of at least one base such as potassium hydroxide or sodium hydroxide (B. Dahwan et al., *Macromolec. Chem.* 1987, 188, 921; C. D. Gutsche et al., *Org. Synth.* 1990, 68, 234; C. D. Gutsche et al., *Org. Synth.* 1990, 68, 238).

In general, the p-(alkyl)calix[8]arenes are the calixarenes that are obtained most easily, as they correspond to the kinetic product of the polycondensation reaction. For their part, the p-(alkyl)calix[4]arenes correspond to the thermodynamic product.

In most cases, withdrawal or substitution of the hydroxyl function of these calixarenes from the alkyl position to para, when it is possible, is at best difficult. In the commonest case of the p-(t-butyl)calixarenes, it is generally a multi-stage process. Firstly, a reagent of the Lewis acid type is generally combined with a phenol to remove the t-butyl group, then secondly, another function can be introduced in place of the t-butyl group, having halogenated the position beforehand. As the reaction is not quantitative, "deterbutylation" becomes problematic, in particular when the number of calixarene units increases. The presence of by-products limits the yield, makes a purification stage necessary and restricts the purity of the product. This can limit the final yield of fully deprotected product, as well as use thereof.

The p-(benzyloxy)calixarenes represent a very useful alternative to the p-(alkyl)calixarenes. The (benzyloxy)phenol units are in fact reduced quantitatively to phenols by hydrogenolysis catalysed by palladium on charcoal, allowing easy post-functionalization.

Few documents describe the synthesis of large calixarenes, i.e. comprising from 9 to 20 repeat units.

Thus, patent CA 2,251,070 describes the production of calixarenes comprising 9 and 11-14 repeat units in low yields, by a two-stage process by reaction of a p-(alkyl) or p-(aralkyl)phenol in an aqueous medium in the presence of a base in quantity of less than 0.5 eq. and then heating in an organic solvent without water. As regards calixarenes comprising 9 and 11-14 repeat units, this patent only describes t-(butyl)calixarenes.

The article of Gutsche et al. (*J. Am. Chem. Soc.* 1999, 121, 4136) describes the production of p-(t-butyl)calix[9-20] arenes in an acid medium.

In contrast, there are no documents describing the synthesis of giant calixarenes, i.e. comprising more than 20 repeat units, in particular from 21 to more than 200 repeat units.

Consequently, it remains an open question as to how to obtain calixarenes that can be easily functionalized on the high crown with a large variety of chemical groups under mild conditions and, in particular, how to obtain calixarenes such as the p-(R-oxy)calix[9-20]arenes with good yields.

One of the aims of the invention is the manufacture of giant p-(R)calixarenes with cumulative yields greater than 50%.

Another aim of the invention is to provide a two-stage synthesis process making it possible to:
obtain a mixture of giant p-(R)calixarenes as well as a single-stage purification procedure by simple crystallization of the mixture of giant p-(R)calixarenes, making it possible to obtain them pure, in particular free from p-(R)calix[7, 8]arenes and linear phenolic oligomers.

Another aim of the invention is to provide a phenolic dimer substituted in position 4 with an R group.

Yet another aim is to provide a solid precursor comprising a mixture of p-(R)-giant calixarenes and linear phenolic oligomers substituted in position 4 with an R group.

Yet another aim is the use of giant p-(R)calixarenes, in a mixture or separately, for the constitution of a material or in the context of reinforcement of materials.

The present invention relates to the use of at least one base in an aqueous solution, in particular selected from barium hydroxide, rubidium hydroxide, lithium hydroxide, caesium hydroxide, potassium hydroxide or sodium hydroxide, with at least one phenol substituted in position 4, of the following formula (I):

(I)

in which R is selected from:
a benzyl group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
a linear or branched $C_1$-$C_{20}$ alkyl group, excluding the t-butyl group,
a benzyloxy group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, P(O)OR$_a$OR$_b$, R$_a$ and R$_b$ representing, independently of one another, a linear or branched C$_1$-C$_{20}$ alkyl, a linear or branched C$_1$-C$_{20}$ alkyloxy group, a linear or branched PEG-1 to 10, the —OH end group of which is alkylated with a linear or branched C$_1$-C$_{20}$ alkyl, a benzyl thioether group —S—CH$_2$-Ph optionally substituted in the ortho and/or para and/or meta position with one or more substituents selected from a halogen, SR' and OR', NR$_a$R$_b$, PR$_a$R$_b$, P(O)R$_a$R$_b$, P(O)OR$_a$OR$_b$, R$_a$ and R$_b$ representing, independently of one another, a linear or branched C$_1$-C$_{20}$ alkyl, a linear or branched C$_1$-C$_{20}$ alkyl thioether group, of formula —S—(C$_1$-C$_{20}$-alkyl), an —NR$_a$R$_b$ group, R$_a$R$_b$ representing, independently of one another, a linear or branched C$_1$-C$_{20}$ alkyl, a dibenzylamine group of formula —N(benzyl)$_2$, in which the two benzyl groups are, independently of one another, optionally substituted in the ortho and/or para and/or meta position with one or more substituents selected from a halogen, SR' and OR', R' representing a linear or branched C$_1$-C$_{20}$ alkyl chain, a C$_3$ to C$_{20}$ cycloalkyl group, NR$_a$R$_b$, PR$_a$R$_b$, P(O)R$_a$R$_b$, P(O)OR$_a$OR$_b$, R$_a$ and R$_b$ representing, independently of one another, a linear or branched C$_1$-C$_{20}$ alkyl, and a source of aqueous formaldehyde, in the absence or in the presence of an organic solvent, thus constituting a reaction medium, said base being at a total concentration comprised from approximately 0.01 to 1 equivalent, in particular comprised from approximately 0.1 equivalent to approximately 0.4 equivalent, in particular equal to 0.13 or 0.4 or 1 equivalent, with respect to said at least one phenol substituted in position 4 of formula (I), said reaction medium being heated to a temperature comprised from 100 to 130° C., and said reaction medium optionally then being subjected to a heat treatment in the presence of heat transfer means, in particular an oven or a liquid, for carrying out a reaction for the preparation of a mixture of giant p-(R)calixarenes the size of which is greater than 20, in particular from 21 to more than 220, in particular from 21 to 220, in particular from 21 to 212, more particularly from 21 to approximately 200.

According to another aspect of the invention, R also represents any other group capable of inducing, in solution or in solid phase, a preorganization of the phenolic units with one another, for example by a micellization effect, by conferring a marked amphiphilic character on the monomer or by interaction with groups of the same nature (for example pi-pi stacking interactions) between extended aromatic units present on the monomer, of the naphthalene, anthracene, pyrene, or perylene type, or also for example by a coordination effect of metal cations on coordinating sites present on the monomers.

The inventors found, surprisingly, that the combination of at least one base in an aqueous solution, in particular selected from barium hydroxide, rubidium hydroxide, lithium hydroxide, caesium hydroxide, potassium hydroxide or sodium hydroxide, in the absence or in the presence of an organic solvent, with at least one phenol substituted in position 4 of formula (I) and with a total concentration of base comprised from approximately 0.01 to 1 equivalent, in particular comprised from approximately 0.1 equivalent to approximately 0.4 equivalent, in particular equal to 0.15 or 0.4 equivalent, or 1 equivalent with respect to said at least one phenol substituted in position 4 of formula (I), made it possible to obtain a mixture of p-(benzyloxy)calix[21-220] arenes mainly, or purified, with good yields.

This result is all the more unexpected in that:

the use of a base such as potassium hydroxide, sodium hydroxide or caesium hydroxide at a concentration equivalent to that of the invention in an organic solvent such as xylene, with a p-(benzyloxy)phenol, leads mainly, with good yields, to a mixture of p-(benzyloxy) calix[6-8]arenes, the use of barium hydroxide in an aqueous solution at a concentration equivalent to that of the invention in an organic medium or at a concentration above 0.5 eq. in an organic medium does not allow access to small calixarenes (i.e. calixarenes of size smaller than nine units) and in particular the calix[6-8]arenes, nor to large calixarenes, and, the use of a base such as potassium hydroxide, sodium hydroxide or caesium hydroxide at a concentration equivalent to that of the invention in the absence of an organic solvent, with a p-(tert-butyl)phenol, does not allow giant calixarenes to be obtained.

This unexpected result can be explained by the concomitant presence of a slightly hindered hydrophobic group (R) in para position of the hydroxide phenol thus making the compound of formula (I) amphiphilic, in such a way that the monomers can be orientated or even be organized with respect to one another in an aqueous solution. The presence of an oxygen atom (potentially coordinating) in para position of the (—OH) group of the phenol can also induce coordination effects on the metal cations present in the reaction medium. Such coordination effects are absent in the case of the p-(alkyl)phenols, and are therefore capable of playing a role in the surprising behaviour observed by the inventors.

The term base denotes any base soluble in an aqueous medium of the metal hydroxide, tertiary amine, carbonate, sulphate, carboxylate type, for example.

It can also denote the use of an organic base of amine type in combination with a metal salt (CsI for example).

The expression "source of aqueous formaldehyde" signifies that formaldehyde in an aqueous solution such as formalin or formol can be used.

The expression "in an aqueous solution" throughout the description signifies that the base is dissolved in a medium mainly consisting of water.

Advantageously, the expression "in an aqueous solution" exclusively denotes water.

The expression "in the absence or in the presence of an organic solvent" signifies that the reaction medium (which comprises water) is respectively devoid of or provided with solvents which are organic compounds which contain carbon atoms, the base as such, the formaldehyde or source of formaldehyde and the phenol also not being considered as organic solvents.

The expression "reaction medium" signifies the mixture of the different components, comprising the base(s), or the phenol(s) substituted in position 4 of formula (I), the source of formaldehyde, all being in an aqueous solution, in the absence of an organic solvent, or in a water-organic solvent medium, in the presence of an organic solvent.

When said mixture has just been constituted, it is called an initial reaction medium, i.e. a reaction medium in which the reaction for the preparation of the p-(R)calixarenes has not yet been carried out, in particular before any heating of said mixture of different compounds.

The giant p-(R)calixarenes have the following structure:

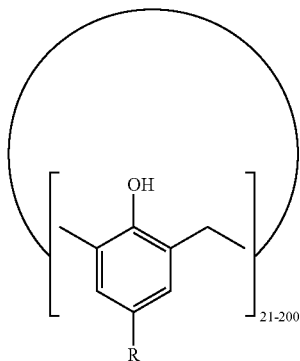

and are therefore constituted by:

a mixture of at least two to more than 180 giant p-(R) calixarenes selected from the group of p-(R)calix[21-220]arenes irrespective of the proportion of each p-(R) calixarene present in the mixture and may also be called "giant p-(R)calixarenes" throughout the description, or one of the p-(R)calix[21-200]arenes, purified or pure.

The p-(R)calix[9-20]arenes are called large calixarenes and as such do not fall within the scope of the invention. It is however possible that they are obtained in minority quantities in a mixture with the p-(R)calix[21-220]arenes.

Throughout the description, the term "purified" or "pure" denotes a compound having a purity greater than or equal to 90%.

The mixture of purified p-(R)calix[21-220]arenes or p-(R) calixarenes are as a general rule obtained in neutralized form after neutralization of the base present in the final reaction medium.

By the expression "in neutralized form", is meant a purified p-(R)calixarene in which all the hydroxyls of the phenol groups have been neutralized, i.e. are in the non-salified OH form.

Without neutralization of the base, the mixture of purified p-(R)calix[21-220]arenes or p-(R)calixarenes are obtained in the potentially salified form (according to the concentration of base and the number of calixarene units), i.e. at least one of the phenol groups is in the form salified with the metal cation originating from the base, in particular the mixture of p-(R)calixarenes or purified p-(R)calixarenes are obtained in the mono-salified form, i.e. only one of the free phenol groups is in the form salified with the metal cation originating from the base.

The term $C_1$-$C_{20}$ alkyl used throughout the description denotes a linear or branched alkyl group comprising 1 to 20 carbon atoms.

By linear $C_1$ to $C_{20}$ alkyl group is meant: a methyl, an ethyl, a propyl, a butyl, a pentyl, a hexyl, a heptyl, an octyl, a nonyl, a decyl, an undecyl, a dodecyl, tridecyl, tetradecyl, pentadecyl, hexadecyl, heptadecyl, octadecyl, nonadecyl and the eicosyl group, as well as certain of their isomers capable of interacting with groups of the same nature (effects of Wan der Waals type "packing") and/or of inducing preorganizations in solution and in solid phase.

By branched alkyl group, is meant an alkyl group as defined above comprising substituents selected from the list of linear alkyl groups defined above, said linear alkyl groups being also capable of being branched.

By $C_3$ to $C_{20}$ cycloalkyl group is meant a cyclopropyl, cyclobutyl, cyclopentyl, cyclohexyl, cycloheptyl, cyclooctyl, cyclonyl, cyclodecyl, cycloundecyl, cyclododecyl, cyclotridecyl, cyclotetradecyl, cyclopentadecyl, cyclohexadecyl, cycloheptadecyl, cyclooctadecyl, cyclononadecyl and cycloeicosyl group.

Such cycloalkyl groups can themselves be substituted with a linear or branched alkyl group as defined above.

Said reaction medium is heated to a temperature comprised from 100 to 130° C. for 30 minutes to 5 hours.

The expression "and then optionally subjected to a heat treatment in the presence of heat transfer means" signifies that after said heating at a temperature comprised from 100 to 130° C., during which water is optionally removed, heat transfer means are applied to the reaction medium, then said reaction medium is heated again.

The heat transfer means are in particular an oven or a solvent, in particular a solvent heated at a temperature comprised from 120° C. to 140° C., for example a solvent the boiling point of which is comprised from 120° C. to 140° C.

By solvent is meant:

a solvent, in particular an organic solvent, in which the organic compounds of the reaction medium are at least partially soluble, for example an aromatic solvent, with a boiling point greater than 50° C., in particular greater than 100° C., or a liquid in which the organic compounds of the reaction medium are not soluble, for example a linear or branched alkane, in particular octane, or a silicone oil, with a boiling point greater than 50° C., in particular greater than 100° C.

By "solvent in which the organic compounds of the reaction medium are at least partially soluble" is meant a solvent that can optionally, depending on its nature, solubilize certain of the constituents of said reaction medium, disperse them (in order to form a colloidal suspension) or to change all or part of them into a gel state.

Thus, when the heat transfer means are for example an oven or a solvent in which the organic compounds of the reaction medium are not soluble, said heat treatment takes place in the solid phase, preferably without stirring.

In an advantageous embodiment, the reaction medium is devoid of organic solvent, the water is removed during said heating at a temperature comprised from 100 to 130° C., and said heat treatment is carried out in the presence of a solvent in which the organic compounds of the reaction medium are at least partially soluble.

In another advantageous embodiment, the reaction medium is devoid of organic solvent, the water is removed during said heating at a temperature comprised from 100 to 130° C., and said heat treatment is carried out in the presence of a solvent in which the organic compounds of the reaction medium are not soluble.

In another advantageous embodiment, the reaction medium is devoid of organic solvent, the water is not removed during said heating at a temperature comprised from 100 to 130° C., and said heat treatment is carried out in the presence of a solvent in which the organic compounds of the reaction medium are at least partially soluble.

In another advantageous embodiment, the reaction medium is devoid of organic solvent, the water is not removed during said heating at a temperature comprised from 100 to 130° C., and said heat treatment is carried out in the presence of a solvent in which the organic compounds of the reaction medium are not soluble.

In another advantageous embodiment, the reaction medium comprises, besides water, an organic solvent, the water is not removed during heating, and said reaction medium is not subjected to said additional heat treatment.

In another advantageous embodiment, the reaction medium comprises, besides water, an organic solvent, the water is not removed during heating, and said reaction medium is subjected to said additional heat treatment, the water being in particular removed during said heat treatment.

The water-organic solvent system is capable of promoting solubilization of all of the organic and inorganic compounds, at the start of the reaction. This therefore makes it possible to maintain the constituents of the reaction medium for a longer time in solution. This is reflected by a better consumption of the reagents and therefore allows 1) a better yield, 2) less by-products (starting products, reaction intermediates etc.) and therefore makes purification easier.

The present invention also relates to the use of at least one base in an aqueous solution, in particular selected from barium hydroxide, rubidium hydroxide, lithium hydroxide, caesium hydroxide, potassium hydroxide or sodium hydroxide, with at least one phenol substituted in position 4 of the following formula (I):

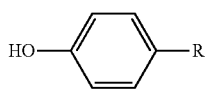

(I)

in which R is selected from:
a benzyl group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
a linear or branched $C_1$-$C_{20}$ alkyl group, excluding the t-butyl group,
a benzyloxy group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
a linear or branched $C_1$-$C_{20}$ alkyloxy group, a linear or branched PEG-1 to 10, the —OH end group of which is alkylated with a linear or branched $C_1$-$C_{20}$ alkyl,
a benzyl thioether group —S—$CH_2$-Ph optionally substituted in the ortho and/or para and/or meta position with one or more substituents selected from a halogen, SR' and OR', $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
a linear or branched $C_1$-$C_{20}$ alkyl thioether group, of formula —S—($C_1$-$C_{20}$-alkyl),
and a source of aqueous formaldehyde,
in the absence of an organic solvent, thus constituting a reaction medium,
said base being at a total concentration comprised from approximately 0.01 to 1 equivalent, in particular comprised from approximately 0.1 equivalent to approximately 0.4 equivalent, in particular equal to 0.13 or 0.4 or 1 equivalent, with respect to said at least one phenol substituted in position 4 of formula (I),
said reaction medium being heated to a temperature comprised from 100 to 130° C., and then optionally subjected to a heat treatment in the presence of an organic solvent,
for carrying out a reaction for the preparation of a mixture of giant p-(R)calixarenes the size of which is greater than 20, in particular from 21 to more than 220, in particular from 21 to 220, in particular from 21 to 212, more particularly from 21 to approximately 200.

The expression "in the absence of an organic solvent" signifies that the reaction medium is devoid of solvents containing carbon atoms, the base as such, the formaldehyde or source of formaldehyde and the phenol also not being considered as organic solvents.

The expression "reaction medium" signifies the mixture of the different components, comprising the base(s), the phenol(s) substituted in position 4 of formula (I), the source of formaldehyde, all being in an aqueous solution.

The expression "and then optionally subjected to a heat treatment in the presence of an organic solvent" signifies that after said heating at a temperature comprised from 100 to 130° C., an organic solvent such as a linear or branched alkane, an aromatic solvent, a silicone oil with a boiling point greater than 50° C., in particular greater than 100° C. is introduced, then the reaction medium is heated again.

In an advantageous embodiment, the present invention relates to the use of at least one base in an aqueous solution with at least one phenol substituted in position 4 of formula (I), as defined above, in which R is selected from:
a benzyloxy group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
a linear or branched $C_1$-$C_{20}$ alkyloxy group, a linear or branched PEG-1 to 10, the —OH end group of which is alkylated with a linear or branched $C_1$-$C_{20}$ alkyl,
a benzyl thioether group —S—$CH_2$-Ph optionally substituted in the ortho and/or para and/or meta position with one or more substituents selected from a halogen, SR' and OR', $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
a linear or branched $C_1$-$C_{20}$ alkyl thioether group, of formula —S—($C_1$-$C_{20}$-alkyl),
an —$NR_aR_b$ group, $R_a$ and $R_b$ representing, independently of one another, a linear or branched $C_1$-$C_{20}$ alkyl,
a dibenzylamine group of formula —N(benzyl)$_2$, in which the two benzyl groups are, independently of one another, optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
and a source of aqueous formaldehyde,
in the absence or in the presence of an organic solvent, thus constituting a reaction medium, said base being at a total concentration comprised from approximately 0.01 to 1 equivalent, in particular comprised from approximately 0.1 equivalent to approximately 0.4 equivalent, in particular equal to 0.15 or 0.4 or 1 equivalent, with respect to said at least one phenol substituted in position 4 of formula (I),
said reaction medium being heated to a temperature comprised from 100 to 130° C., and said reaction medium then optionally being subjected to a heat treatment in the presence of heat transfer means, in particular an oven or a solvent,
for carrying out a reaction for the preparation of a mixture of giant p-(R)calixarenes the size of which is greater than 20, in particular from 21 to more than 220, in particular from 21 to 220, in particular from 21 to 212, more particularly from 21 to approximately 200, even more particularly from 21 to approximately 100.

In an advantageous embodiment, the present invention relates to the use of at least one base in an aqueous solution with at least one phenol substituted in position 4 of formula (I), as defined above, in which R is selected from:
  a benzyloxy group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
  a linear or branched $C_1$-$C_{20}$ alkyloxy group, a linear or branched PEG-1 to 10, the —OH end group of which is alkylated with a linear or branched $C_1$-$C_{20}$ alkyl,
  a benzyl thioether group —S—CH$_2$-Ph optionally substituted in the ortho and/or para and/or meta position with one or more substituents selected from a halogen, SR' and OR', $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
  a linear or branched $C_1$-$C_{20}$ alkyl thioether group, of formula —S—($C_1$-$C_{20}$-alkyl),
and a source of aqueous formaldehyde,
in the absence of an organic solvent, thus constituting a reaction medium,
said base being at a total concentration comprised from approximately 0.01 to 1 equivalent, in particular comprised from approximately 0.1 equivalent to approximately 0.4 equivalent, in particular equal to 0.15 or 0.4 or 1 equivalent, with respect to said at least one phenol substituted in position 4 of formula (I),
said reaction medium being heated to a temperature comprised from 100 to 130° C., and then optionally subjected to a heat treatment in the presence of an organic solvent,
for carrying out a reaction for the preparation of a mixture of giant p-(R)calixarenes the size of which is greater than 20, in particular from 21 to more than 220, in particular from 21 to 220, in particular from 21 to 212, more particularly from 21 to approximately 200, even more particularly from 21 to approximately 100.
  In the above, R can also represent:
  an —$NR_aR_b$ group, $R_a$ and $R_b$ representing, independently of one another, a linear or branched $C_1$-$C_{20}$ alkyl,
  a dibenzylamine group of formula —N(benzyl)$_2$, in which the two benzyl groups are, independently of one another, optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl.

In this embodiment, the phenol in position 4 is substituted with a $C_1$-$C_{20}$ O-alkyl(alkyloxy) or an O-benzyl(benzyloxy), substituted or unsubstituted, but cannot have an alkyl or a benzyl directly bound in position 4.

In an advantageous embodiment, the present invention relates to the use of at least one base in an aqueous solution with at least one phenol substituted in position 4 of formula (I), as defined above, in which R is selected from:
  a benzyl group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
  a linear or branched $C_5$-$C_{20}$ alkyl group,
  a benzyloxy group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
  a linear or branched $C_5$-$C_{20}$ alkyloxy group, a linear or branched PEG-1 to 10, the —OH end group of which is alkylated with a linear or branched $C_1$-$C_{20}$ alkyl,
  a benzyl thioether group —S—CH$_2$-Ph optionally substituted in the ortho and/or para and/or meta position with one or more substituents selected from a halogen, SR' and OR', $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
  a linear or branched $C_5$-$C_{20}$ alkyl thioether group, of formula —S—($C_5$-$C_{20}$-alkyl).
  In the above, R can also represent:
  an —$NR_aR_b$ group, $R_a$ and $R_b$ representing, independently of one another, a linear or branched $C_1$-$C_{20}$ alkyl,
  a dibenzylamine group of formula —N(benzyl)$_2$, in which the two benzyl groups are, independently of one another, optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl.

In this embodiment, the phenol of formula (I) cannot therefore be substituted in position 4 with a methyl, ethyl, isopropyl, propyl, butyl, isobutyl, sec-butyl or t-butyl or by a methyloxy, ethyloxy, isopropyloxy, propyloxy, butyloxy, isobutyloxy, sec-butyloxy or t-butyloxy.

In an advantageous embodiment, the present invention relates to the use of at least one base in an aqueous solution with at least one phenol substituted in position 4 of formula (I), as defined above, in which water is produced during the reaction, said water being removed from the reaction medium during said heating at a temperature comprised from 100 to 130° C. and in which a solid precursor in the form of an optionally isolated, hard brittle resin is obtained.

During the condensation reaction of phenol with formaldehyde in the presence of the base, water is also formed during the reaction.

The water formed in the reaction medium during the reaction as well as a part of the water initially present is removed by techniques well known to a person skilled in the art, for example by means of a Dean-Stark apparatus or by flushing the reaction medium during the reaction using an inert gas such as nitrogen or argon.

It is of course understood that not all the water initially present is totally removed.

In this case, the proportion of water present after obtaining the resin is less than 5% by weight The removal of the water leads to the complete solidification of the medium, i.e. caking of the medium and to the formation of a solid precursor which essentially comprises a mixture of giant p-(R)calixarenes the size distribution and purity of which depend on R and the nature of the base. The precursor further comprises a variable the proportion of linear oligomers including linear dimer precursors of giant p-(R)calixarenes.

The precursor being in solid form, it can easily be isolated by simple filtration of the reaction medium.

In an advantageous embodiment, the present invention relates to the use of at least one base in an aqueous solution with at least one phenol substituted in position 4 of formula (I) in which water is produced during the reaction, said water being removed from the reaction medium during said heating at a temperature comprised from 100 to 130° C., as defined above, in which said solid precursor obtained in the form of a hard brittle resin is isolated from the reaction medium, and not subjected to heat treatment, for the preparation of a mixture of giant p-(R)calixarenes the size of which is comprised from 21 to 50 phenolic units.

In this embodiment, the solid precursor obtained is isolated but is not subjected to said heat treatment in the presence of heat transfer means.

In an advantageous embodiment, the present invention relates to the use of at least one base in an aqueous solution with at least one phenol substituted in position 4 of formula (I) in which water is produced during the reaction, said water being removed from the reaction medium during said heating at a temperature comprised from 100 to 130° C., as defined above, in which said solid precursor obtained in the form of a hard brittle resin is isolated from the reaction medium, and not subjected to heat treatment in the presence of an organic solvent, for the preparation of a mixture of giant p-(R) calixarenes the size of which is comprised from 21 to 50 phenolic units.

In this embodiment, the solid precursor obtained is isolated but is not subjected to said heat treatment in the presence of an organic solvent.

The product obtained in the hard brittle resin is therefore essentially constituted by giant p-(R)calixarenes and does not therefore require heat treatment to complete the formation of the macrocycles (giant p-(R)calixarenes).

Depending on R, the base used (as well as its concentration), and time, it can also contain however, in a variable proportion, linear oligomers originating from the condensation of the phenol substituted in position 4 of formula (I) and then requires a purification stage.

In an advantageous embodiment, said heating at a temperature comprised from 100 to 130° C. is carried out from 30 minutes to 5 hours, advantageously from 1 h to 5 h, more advantageously from 2 h to 5 h.

Advantageously, said heating at a temperature comprised from 100 to 130° C. is carried out in particular for 3 h.

Advantageously, said heating at a temperature comprised from 100 to 130° C. is carried out in particular for 4 h.

Advantageously, said heating at a temperature comprised from 100 to 130° C. is carried out in particular for 5 h.

The duration of said heating depends on the concentration of base. A low concentration of base, for example 0.1 equivalent with respect to the phenol, the complete solidification in the form of a hard brittle resin is slow, for example 3 h, whereas at a high concentration of base, for example from 0.4 to 1 equivalent with respect to the phenol, solidification is more rapid, for example 1 h.

In an advantageous embodiment, the present invention relates to the use of at least one base in an aqueous solution with at least one phenol substituted in position 4 of formula (I) in which water is produced during the reaction, said water being removed from the reaction medium during said heating at a temperature comprised from 100 to 130° C., as defined above, in which said solid precursor obtained in the form of a hard brittle resin is isolated from the reaction medium, and not subjected to heat treatment, as defined above, in which the phenol substituted in position 4 of formula (I) is 4-octyloxyphenol or 4-octylphenol.

In an advantageous embodiment, the present invention relates to the use of at least one base in an aqueous solution with at least one phenol substituted in position 4 of formula (I) in which water is produced during the reaction, said water being removed from the reaction medium during said heating at a temperature comprised from 100 to 130° C., as defined above, in which said solid precursor obtained in the form of a hard brittle resin is isolated from the reaction medium, and not subjected to heat treatment, as defined above, in which the phenol substituted in position 4 of formula (I) is 4-octyloxyphenol, 4-methoxyphenol, 4-benzyloxyphenol, 4-dibenzylaminophenol, 4-methylphenol, 4-ethylphenol or 4-benzylphenol.

In an advantageous embodiment, the present invention relates to the use of at least one base in an aqueous solution with at least one phenol substituted in position 4 of formula (I) in which water is produced during the reaction, said water being removed from the reaction medium during said heating at a temperature comprised from 100 to 130° C., as defined above, in which said solid precursor obtained in the form of a hard brittle resin is isolated from the reaction medium, and not subjected to heat treatment in the presence of an organic solvent, as defined above, in which the phenol substituted in position 4 of formula (I) is 4-octyloxyphenol or 4-octylphenol.

In an advantageous embodiment, the present invention relates to the use of at least one base in an aqueous solution with at least one phenol substituted in position 4 of formula (I) in which water is produced during the reaction, said water being removed from the reaction medium during said heating at a temperature comprised from 100 to 130° C., as defined above, in which said solid precursor obtained in the form of a hard brittle resin is isolated from the reaction medium, and not subjected to heat treatment in the presence of an organic solvent, as defined above, in which the phenol substituted in position 4 of formula (I) is 4-octyloxyphenol, 4-methoxyphenol, 4-benzyloxyphenol, 4-dibenzylaminophenol, 4-methylphenol, 4-ethylphenol or 4-benzylphenol.

In these embodiments, the average size of the giant p-(octyloxy)calix[21-50]arenes obtained is 35, determined by the centred Gaussian using gel permeation chromatography (GPC), with a average size of 54 phenolic units.

The giant p-(octyloxy)calix[21-50]arenes have the advantage of being more stable in an acid medium and in a reducing medium than the p-(benzyloxy)calix[21-50]arenes.

The giant p-(octyloxy)calix[21-50]arenes and the p-(octyl)calix[21-50]arenes have a more marked amphiphilic character, which is potentially useful for the production of supramolecular architectures (micelles, vesicles etc.). This is demonstrated by the fact that these giant octyloxy calixarenes are perfectly (and very rapidly) dispersed in chloroform in the form of large size aggregates (very broadened NMR signals and the presence of a light diffusion peak at 200 nm). This behaviour is not observed with the p-(benzyloxy)calixarenes.

In an advantageous embodiment, the present invention relates to the use of at least one base in an aqueous solution with at least one phenol substituted in position 4 of formula (I) in which water is produced during the reaction, said water being removed from the reaction medium during said heating at a temperature comprised from 100 to 130° C., as defined above, in which said solid precursor obtained in the form of a hard brittle resin is isolated from the reaction medium, and not subjected to heat treatment, in which the phenol substituted in position 4 of formula (I) is 4-octyloxyphenol or 4-octylphenol, as defined above,
in which the base used is barium hydroxide.

In an advantageous embodiment, the present invention relates to the use of at least one base in an aqueous solution with at least one phenol substituted in position 4 of formula (I) in which water is produced during the reaction, said water being removed from the reaction medium during said heating at a temperature comprised from 100 to 130° C., as defined above, in which said solid precursor obtained in the form of a hard brittle resin is isolated from the reaction medium, and not subjected to heat treatment, in which the phenol substituted in position 4 of formula (I) is 4-octyloxyphenol, 4-methoxyphenol, 4-benzyloxyphenol, 4-dibenzylaminophenol, 4-methylphenol, 4-ethylphenol or 4-benzylphenol, as defined above,
in which the base used is barium hydroxide.

In an advantageous embodiment, the present invention relates to the use of at least one base in an aqueous solution with at least one phenol substituted in position 4 of formula (I) in which water is produced during the reaction, said water being removed from the reaction medium during said heating at a temperature comprised from 100 to 130° C., as defined above, in which said solid precursor obtained in the form of a hard brittle resin is isolated from the reaction medium, and not subjected to heat treatment in the presence of an organic solvent, in which the phenol substituted in position 4 of formula (I) is 4-octyloxyphenol or 4-octylphenol, as defined above,
in which the base used is barium hydroxide.

In an advantageous embodiment, the present invention relates to the use of at least one base in an aqueous solution with at least one phenol substituted in position 4 of formula (I) in which water is produced during the reaction, said water being removed from the reaction medium during said heating at a temperature comprised from 100 to 130° C., as defined above, in which said solid precursor obtained in the form of a hard brittle resin is isolated from the reaction medium, and not subjected to heat treatment in the presence of an organic solvent, in which the phenol substituted in position 4 of formula (I) is 4-octyloxyphenol, 4-methoxyphenol, 4-benzyloxyphenol, 4-dibenzylaminophenol, 4-methylphenol, 4-ethylphenol or 4-benzylphenol, as defined above,
in which the base used is barium hydroxide.

In an advantageous embodiment, the present invention relates to the use of at least one base in an aqueous solution with at least one phenol substituted in position 4 of formula (I) in which water is produced during the reaction, said water being removed from the reaction medium during said heating at a temperature comprised from 100 to 130° C., as defined above, in which said solid precursor in the form of a hard brittle resin is preceded by the formation of an optionally isolated phenolic dimer.

Depending on the heating time at a temperature comprised from 100 to 130° C. of the phenol substituted in position 4 of formula (I) with the so-called base and the aqueous formaldehyde, with removal of the water formed, linear oligomers of the following formula (III), of variable size corresponding to the condensation of the phenol substituted in position 4 of formula (I) with the formaldehyde before cyclization to giant p-(R)calixarenes are firstly obtained:

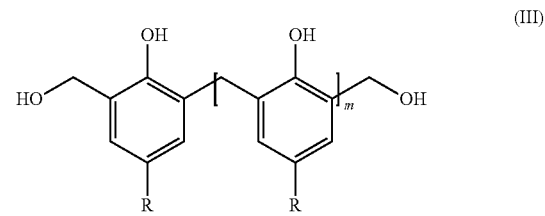

(III)

in which R is selected from:
a benzyl group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
a linear or branched $C_1$-$C_{20}$ alkyl group, excluding the t-butyl group,
a benzyloxy group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
a linear or branched $C_1$-$C_{20}$ alkyloxy group, a linear or branched PEG-1 to 10, the —OH end group of which is alkylated with a linear or branched $C_1$-$C_{20}$ alkyl,
a benzyl thioether group —S—$CH_2$-Ph optionally substituted in the ortho and/or para and/or meta position with one or more substituents selected from a halogen, SR' and OR', $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
a linear or branched $C_1$-$C_{20}$ alkyl thioether group, of formula —S—($C_1$-$C_{20}$-alkyl), and m is an integer comprised from 2 to more than 200.

In the above, R can also represent:
an —$NR_aR_b$ group, $R_a$ and $R_b$ representing, independently of one another, a linear or branched $C_1$-$C_{20}$ alkyl,
a dibenzylamine group of formula —$N(benzyl)_2$, in which the two benzyl groups are, independently of one another, optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)$ $OR_aOR_b$, $R_a$ and $R_b$ representing, independently of one another, a linear or branched $C_1$-$C_{20}$ alkyl.

Advantageously, heating at a temperature comprised from 100 to 130° C. is carried out from approximately 10 minutes to approximately 25 minutes in order to obtain the oligomers.

More advantageously, heating at a temperature comprised from 100 to 130° C. is carried out for approximately 20 minutes in order to obtain the oligomers.

These oligomers are then transformed to dimers corresponding to the following formula (II), if heating of an initial reaction medium is carried out for 30 minutes to 2 h:

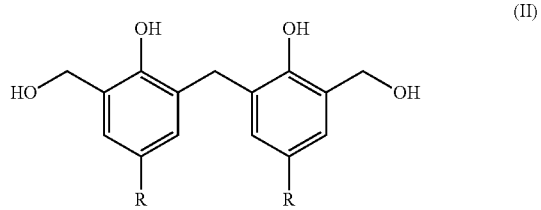

(II)

where R is as described above.

Said dimer can then be isolated or not isolated.

Said dimer which is not isolated is rearranged in order to form oligomers of various size or combines with another dimer or residual oligomers in order to form solid material in the form of a resin comprising approximately 50% to 90% of giant p-(R)calixarenes (depending on the alkyl or alkyloxy group in para position and the base) when heating at a temperature comprised from 100 to 130° C. is continued for an additional 1 h to 3 h after formation of the dimer.

Advantageously, the additional heating is carried out for approximately 1 h.

Advantageously, the additional heating is carried out for approximately 2 h.

Advantageously, the additional heating is carried out for approximately 3 h.

When the heating time at a temperature comprised from 100 to 130° C. is controlled, especially when the base is LiOH, between 30 minutes and 5 hours, the dimer can then be isolated by filtration and then returned to react in an aqueous medium comprising at least one base in an aqueous solution in order to continue heating at a temperature comprised from 100 to 130° C. for 1 to 3 h.

Advantageously, the continuation of the additional heating is carried out for approximately 1 h.

Advantageously, the continuation of the additional heating is carried out for approximately 2 h.

Advantageously, the continuation of the additional heating is carried out for approximately 3 h.

In an advantageous embodiment, the present invention relates to the use of at least one base in an aqueous solution with at least one phenol substituted in position 4 of formula (I), in which water is produced during the reaction, said water being removed from the reaction medium during said heating at a temperature comprised from 100 to 130° C. and a solid precursor in the form of an optionally isolated, hard brittle resin is obtained, said solid precursor in the form of a hard brittle resin being preceded by the formation of an optionally isolated phenolic dimer, as defined above, in which said solid precursor in the form of a hard brittle resin or said phenolic dimer, optionally isolated from the reaction medium, is placed in the presence of heat transfer means, in particular a solvent in which said solid precursor in the form of a hard brittle resin and said phenolic dimer are insoluble, in particular in a linear or branched alkane with a boiling point greater than 50° C., in particular greater than 100° C., in particular in octane or a silicone oil, and is subjected to said heat treatment, for the preparation of a mixture of giant p-(R)calixarenes the size of which is comprised from 21 to 50 phenolic units, the average size of the giant p-(R)calix[21-50]arenes obtained is 28, determined by the centred Gaussian using light scattering experiments.

The heat treatment is in particular carried out under reflux of said solvent, with or without stirring, preferably without stirring of the reaction medium, and in particular has the effect on the one hand, of completing the formation of the macrocycles, in particular those comprised in the solid precursor in the form of a resin, but also of increasing the size of the macrocycles obtained starting equally well from the solid precursor in the form of a resin as from said dimer.

In an advantageous embodiment, the present invention relates to the use of at least one base in an aqueous solution with at least one phenol substituted in position 4 of formula (I), in which water is produced during the reaction, said water being removed from the reaction medium during said heating at a temperature comprised from 100 to 130° C. and a solid precursor in the form of an optionally isolated, hard brittle resin is obtained, said solid precursor in the form of a hard brittle resin being preceded by the formation of an optionally isolated phenolic dimer, as defined above, in which said solid precursor in the form of a hard brittle resin or said phenolic dimer, optionally isolated from the reaction medium, is placed in the presence of an organic solvent in which said solid precursor in the form of a hard brittle resin and said phenolic dimer are insoluble, in particular in a linear or branched alkane with a boiling point greater than 50° C., in particular greater than 100° C., in particular in octane or a silicone oil, and is subjected to said heat treatment, for the preparation of a mixture of giant p-(R)calixarenes the size of which is comprised from 21 to 50 phenolic units, the size of the giant p-(R)calix[21-50]arenes obtained is 28, determined by the centred Gaussian observed using GPC and confirmed by light scattering experiments.

This size of 28 therefore corresponds to the size of the peak, i.e. the most represented size in the sample.

The heat treatment is carried out under reflux of said organic solvent, with or without stirring, preferably without stirring of the reaction medium, and in particular has the effect on the one hand, of completing the formation of the macrocycles, in particular those comprised in the solid precursor in the form of a resin, but also of increasing the size of the macrocycles obtained starting equally well from the solid precursor in the form of a resin as from said dimer.

The giant calixarenes obtained comprise however a proportion of calix[7]arenes and/or calix[8]arenes which is variable depending on R.

The more the solid precursor in the form of a resin or the dimer is insoluble in the organic solvent, the more the proportion of giant calixarenes increases.

When the heat treatment is carried out with stirring, the macrocycles obtained are of greater purity than those obtained in the absence of stirring; however, the proportion of small calixarenes and in particular of calix[7]arenes and/or calix[8]arenes is greater than that capable of being obtained in the absence of stirring.

However, when the heat treatment is carried out without stirring, the yield of giant calixarenes is greater than that obtained with stirring, the proportion of small calixarenes and in particular of calix[7]arenes and/or calix[8]arenes being lower than that capable of being obtained with stirring.

However, the macrocycles obtained are of lower purity than that of those obtained with stirring.

The duration of the heat treatment must also be controlled and must be comprised from 3 to 8 h depending on R and the base used.

Above 8 h, the proportion of small calixarenes obtained increases until only small calixarenes are obtained, the giant calixarenes disappearing by dissociating in favour of said small calixarenes.

The kinetics of the formation and dissociation mechanisms of the giant calixarenes is directly linked to:
- the size of the counter-ion of the base; the appearance of the small calixarenes is more rapid with small alkali metals such as lithium and sodium, and is slower with large alkali metals and with barium hydroxide;
- the sequence of reactions leading from oligomers to dimers, then giant calixarenes and finally small calixarenes is much more rapid when the concentration of the base is low, i.e. comprised from 0.1 to 0.4 equivalent.

Advantageously, the heat treatment is comprised from approximately 3 to 4 h.

Advantageously, when the heat treatment is comprised from 3 to 4 h, the base used is LiOH, KOH, NaOH, CsOH or RbOH.

Advantageously, the heat treatment is comprised from approximately 6 to 8 h, in particular 7 h.

Advantageously, when the heat treatment is comprised from approximately 6 to 8 h, in particular 7 h, the base used is $Ba(OH)_2$.

Depending on the solvent used for the heat treatment, the size of the macrocycles obtained can be modulated.

The lower the reaction temperature mixture, the more the size of the macrocycles obtained decreases.

In an advantageous embodiment, the present invention relates to the use of at least one base in an aqueous solution with at least one phenol substituted in position 4 of formula (I), in which water is produced during the reaction, said water being removed from the reaction medium during said heating at a temperature comprised from 100 to 130° C. and a solid precursor in the form of an optionally isolated, hard brittle resin is obtained, said solid precursor in the form of a hard brittle resin being preceded by the formation of an optionally isolated phenolic dimer, as defined above, in which said solid precursor in the form of a hard brittle resin or said phenolic dimer, optionally isolated from the reaction medium, is placed in the presence of an organic solvent in which said solid precursor in the form of a hard brittle resin or said phenolic dimer are at least partially soluble, in particular in xylene or toluene, DMSO or DMF, and is subjected to said heat treatment,
for the preparation of a mixture of giant p-(R)calixarenes the size of which is comprised from 21 to approximately 212 phenolic units.

The heat treatment is carried out under reflux of said organic solvent, with or without stirring, preferably without stirring of the reaction medium.

When the solid precursor in the form of a resin or a dimer is dissolved for the heat treatment stage, the macrocycles obtained are of greater purity with respect to those obtained in the absence of dissolution of the solid precursor in the form of a resin, or of the dimer in the organic solvent; however, the proportion of small calixarenes and in particular of calix[7]arenes and/or calix[8]arenes is greater.

The duration of the heat treatment must also be controlled and must be comprised from 3 to 8 h depending on R and the base used.

Above 8 h, the proportion of small calixarenes obtained increases until only small calixarenes are obtained, the giant calixarenes disappearing by dissociating in favour of said small calixarenes.

Advantageously, the heat treatment is comprised from approximately 3 to 4 h.

Advantageously, when the heat treatment is comprised from 3 to 4 h, the base used is LiOH, KOH, NaOH, CsOH or RbOH.

Advantageously, the heat treatment is comprised from approximately 6 to 8 h, in particular 7 h.

Advantageously, when the heat treatment is comprised from approximately 6 to 8 h, in particular 7 h, the base used is $Ba(OH)_2$.

In the case where said solid precursor in the form of a hard brittle resin or said phenolic dimer is placed in the presence of heat transfer means in the form of an organic solvent in which it is partially soluble, it should be noted that the duration of the heat treatment is shorter than that of the heat treatment relating to the case where said solid precursor in the form of a hard brittle resin or said phenolic dimer is placed in the presence of heat transfer means in the form of an oven or of a solvent in which it is insoluble.

In the case where said solid precursor in the form of a hard brittle resin or said phenolic dimer is placed in the presence of an organic solvent in which it is partially soluble, it should be noted that the heat treatment is shorter than that relating to the case where said solid precursor in the form of a hard brittle resin or said phenolic dimer is insoluble in said organic solvent.

Depending on the solvent used for the heat treatment with dissolution, the size of the macrocycles obtained can be modulated.

The lower the temperature of the reaction mixture, the more the size of the macrocycles obtained decreases.

In an advantageous embodiment, the present invention relates to the use of at least one base in an aqueous solution with at least one phenol substituted in position 4 of formula (I), in which water is produced during the reaction, said water being removed from the reaction medium during said heating at a temperature comprised from 100 to 130° C. and a solid precursor in the form of an optionally isolated, hard brittle resin is obtained, said solid precursor in the form of a hard brittle resin being preceded by the formation of an optionally isolated phenolic dimer, in which said solid precursor in the form of a hard brittle resin or said phenolic dimer, optionally isolated from the reaction medium, is placed in the presence of heat transfer means in the form of an oven or of a solvent, in which said solid precursor in the form of a hard brittle resin and said phenolic dimer are insoluble, or of an organic solvent in which said solid precursor in the form of a hard brittle resin and said phenolic dimer are at least partially soluble,
said phenol substituted in position 4 of formula (I) being 4-benzyloxyphenol.

In particular, the heat treatment is carried out under reflux of said organic solvent, in which said solid precursor in the form of a hard brittle resin and said phenolic dimer are at least partially soluble, with or without stirring, preferably without stirring of the reaction medium.

The heat treatment can be carried out under reflux of said solvent, in which said solid precursor in the form of a hard brittle resin and said phenolic dimer are insoluble, with or without stirring, preferably without stirring of the reaction medium.

In the case where the resin is subjected to a heat treatment in a solvent, in which it is insoluble, it is possible for example to use a silicone oil with a high enough boiling point to not use a refrigeration system, which simplifies the process.

In an advantageous embodiment, the present invention relates to the use of at least one base in an aqueous solution with at least one phenol substituted in position 4 of formula (I), in which water is produced during the reaction, said water being removed from the reaction medium during said heating at a temperature comprised from 100 to 130° C. and a solid precursor in the form of an optionally isolated, hard brittle resin is obtained, said solid precursor in the form of a hard brittle resin being preceded by the formation of an optionally isolated phenolic dimer, in which said solid precursor in the form of a hard brittle resin or said phenolic dimer, optionally isolated from the reaction medium, is placed in the presence of an organic solvent in which said solid precursor in the form of a hard brittle resin and said phenolic dimer are insoluble, or of an organic solvent in which said solid precursor in the form of a hard brittle resin and said phenolic dimer are at least partially soluble, said phenol substituted in position 4 of formula (I) being 4-benzyloxyphenol.

The heat treatment is carried out under reflux of said organic solvent, with or without stirring, preferably without stirring of the reaction medium.

In the case where the resin is subjected to a heat treatment in a solvent in which it is insoluble, it is possible to use a silicone oil with a high enough boiling point not to have to use a refrigeration system, which simplifies the process.

In an advantageous embodiment, the present invention relates to the use of at least one base in an aqueous solution with at least one phenol substituted in position 4 of formula (I), as defined above, in which water is produced during the reaction, said water being retained in the reaction medium during said heating at a temperature comprised from 100 to 130° C. and a solid precursor, in the form of an optionally isolated precipitate is obtained.

In this embodiment, the water formed during the reaction is not removed but retained in the reaction medium.

The consequence of this is that the reaction medium does not solidify completely but quite the opposite; a precipitate, in suspension in water, is obtained. The precipitate can be isolated by simple filtration.

In an advantageous embodiment, the present invention relates to the use of at least one base in an aqueous solution with at least one phenol substituted in position 4 of formula (I), in which water is produced during the reaction, said water being retained in the reaction medium during said heating at a temperature comprised from 100 to 130° C. and a solid precursor, in the form of an optionally isolated precipitate is obtained, as defined above, in which said solid precursor in the form of a precipitate is isolated from the reaction medium and not subjected to heat treatment, for the preparation of a mixture of giant p-(R)calixarenes the size of which is comprised from 21 to 35 phenolic units.

In an advantageous embodiment, the present invention relates to the use of at least one base in an aqueous solution with at least one phenol substituted in position 4 of formula (I), in which water is produced during the reaction, said water being retained in the reaction medium during said heating at a temperature comprised from 100 to 130° C. and a solid precursor, in the form of an optionally isolated precipitate is obtained, as defined above, in which said solid precursor in the form of a precipitate is isolated from the reaction medium and not subjected to heat treatment in the presence of an organic solvent, for the preparation of a mixture of giant p-(R)calixarenes the size of which is comprised from 21 to 35 phenolic units.

The product obtained in the precipitate is therefore essentially constituted by giant p-(R)calixarenes and does not necessarily require heat treatment in order to complete the formation of the macrocycles (giant p-(R)calixarenes).

The giant p-(R)calixarenes are of lower size when water is retained with respect to the embodiment with removal of the water.

Depending on R and the base used, the product obtained in the precipitate can however also contain, in a variable proportion, linear oligomers originating from the condensation of the phenol substituted in position 4 of formula (I) and then requires a purification stage.

In an advantageous embodiment, said heating at a temperature comprised from 100 to 130° C. is carried out for 30 minutes at 5 hours, advantageously for 1 h at 5 h, more advantageously for 2 h at 5 h.

Advantageously, said heating at a temperature comprised from 100 to 130° C. is carried out in particular for 3 h.

Advantageously, said heating at a temperature comprised from 100 to 130° C. is carried out in particular for 4 h.

Advantageously, said heating at a temperature comprised from 100 to 130° C. is carried out in particular for 5 h.

In an advantageous embodiment, the present invention relates to the use of at least one base in an aqueous solution with at least one phenol substituted in position 4 of formula (I), in which water is produced during the reaction, said water being retained in the reaction medium during said heating at a temperature comprised from 100 to 130° C. and a solid precursor, in the form of a precipitate is obtained, said solid precursor in the form of a precipitate being isolated from the reaction medium and not subjected to heat treatment, as defined above, in which the base used is barium hydroxide.

In an advantageous embodiment, the present invention relates to the use of at least one base in an aqueous solution with at least one phenol substituted in position 4 of formula (I), in which water is produced during the reaction, said water being retained in the reaction medium during said heating at a temperature comprised from 100 to 130° C. and a solid precursor, in the form of a precipitate is obtained, said solid precursor in the form of a precipitate being isolated from the reaction medium and not subjected to heat treatment in the presence of an organic solvent, as defined above, in which the base used is barium hydroxide.

In an advantageous embodiment, the present invention relates to the use of at least one base in an aqueous solution with at least one phenol substituted in position 4 of formula (I), in which water is produced during the reaction, said water being retained in the reaction medium during said heating at a temperature comprised from 100 to 130° C. and a solid precursor, in the form of a precipitate is obtained, in which said solid precursor in the form of a precipitate is preceded by the formation of an optionally isolated phenolic dimer.

Depending on the heating time at a temperature comprised from 100 to 130° C., of the phenol substituted in position 4 of formula (I) with said base and the aqueous formaldehyde, with removal of the water formed, the following linear oligomers of formula (III), of variable size, corresponding to the condensation of the phenol substituted in position 4 of formula (I) with the formaldehyde are obtained before cyclization to giant p-(R)calixarenes:

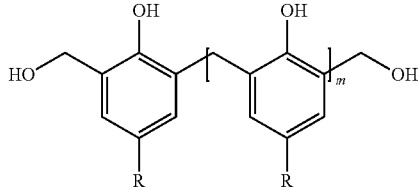

(III)

in which R is selected from:
a benzyl group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
a linear or branched $C_1$-$C_{20}$ alkyl group, excluding the t-butyl group,
a benzyloxy group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
a linear or branched $C_1$-$C_{20}$ alkyloxy group, a linear or branched PEG-1 to 10, the —OH end group of which is alkylated with a linear or branched $C_1$-$C_{20}$ alkyl,
a benzyl thioether group —S—$CH_2$-Ph optionally substituted in the ortho and/or para and/or meta position with one or more substituents selected from a halogen, SR' and OR', $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
a linear or branched $C_1$-$C_{20}$ alkyl thioether group, of formula —S—($C_1$-$C_{20}$-alkyl),
and m is an integer comprised from 2 to more than 200.
In the above, R can also represent:
an —$NR_aR_b$ group, $R_a$ and $R_b$ representing, independently of one another, a linear or branched $C_1$-$C_{20}$ alkyl,
a dibenzylamine group of formula —N(benzyl)$_2$, in which the two benzyl groups are, independently of one another, optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl.

Advantageously, heating at a temperature comprised from 100 to 130° C. is carried out for approximately 10 minutes at approximately 25 minutes in order to obtain the oligomers.

More advantageously, heating at a temperature comprised from 100 to 130° C. is carried out for approximately 20 minutes in order to obtain the oligomers.

These oligomers are then converted to corresponding dimers of the following formula (II), if heating of an initial reaction medium is carried out for 30 minutes to 2 h:

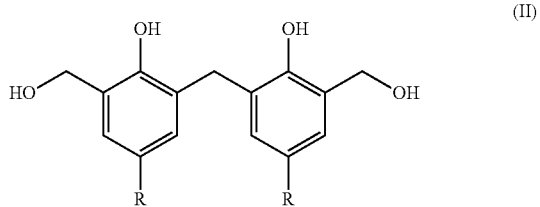

(II)

in which R is as described above.

Said dimer can then be isolated or not isolated.

Said dimer which is not isolated is rearranged to form oligomers of various size either combining with another dimer or residual oligomers in order to form the solid precursor in the form of a resin comprising approximately 50% giant p-(R)calixarenes when heating at a temperature comprised from 100 to 130° C. is continued for an additional 1 h to 3 h.

Advantageously, the additional heating is carried out for approximately 1 h.

Advantageously, the additional heating is carried out for approximately 2 h.

Advantageously, the additional heating is carried out for approximately 3 h.

When the heating time at a temperature comprised from 100 to 130° C. is controlled, between 30 minutes and 2 hours, the dimer can then be isolated by filtration and then returned to react in an aqueous medium or a water-organic solvent combination comprising at least one base in an aqueous solution in order to continue heating at a temperature comprised from 100 to 130° C. for 1 to 3 h.

Advantageously, the additional heating is continued for approximately 1 h.

Advantageously, the additional heating is continued for approximately 2 h.

Advantageously, the additional heating is continued for approximately 3 h.

In an advantageous embodiment, the present invention relates to the use of at least one base in an aqueous solution with at least one phenol substituted in position 4 of formula (I), in which water is produced during the reaction, said water being retained in the reaction medium during said heating at a temperature comprised from 100 to 130° C. and a solid precursor, in the form of an optionally isolated precipitate is obtained, said solid precursor in the form of a precipitate being preceded by the formation of an optionally isolated phenolic dimer, as defined above,
in which said solid precursor in the form of a precipitate or said phenolic dimer, optionally isolated from the aforesaid reaction medium, is placed in the presence of heat transfer means in the form of an oven or of a solvent, in particular a solvent in which said solid precursor in the form of a precipitate and said phenolic dimer are insoluble, in particular in a linear or branched alkane with a boiling point greater than 50° C., in particular greater than 100° C., in particular in octane, and is subjected to said heat treatment,
for the preparation of a mixture of giant p-(R)calixarenes the size of which is comprised from 21 to approximately 212 phenolic units.

In particular, the heat treatment is carried out under reflux of said solvent, in particular organic, with or without stirring, preferably without stirring of the reaction medium, and in particular has the effect on the one hand, of completing the formation of the macrocycles, in particular starting from linear oligomers comprised in the solid precursor in the form of a resin, but also of increasing the size of the macrocycles obtained starting equally well from the solid precursor in the form of a resin as from said dimer.

In an advantageous embodiment, the present invention relates to the use of at least one base in an aqueous solution with at least one phenol substituted in position 4 of formula (I), in which water is produced during the reaction, said water being retained in the reaction medium during said heating at a temperature comprised from 100 to 130° C. and a solid precursor, in the form of an optionally isolated precipitate is obtained, said solid precursor in the form of a precipitate being preceded by the formation of an optionally isolated phenolic dimer, as defined above, in which said solid precursor in the form of a precipitate or said phenolic dimer, optionally isolated from the aforesaid reaction medium, is placed in the presence of an organic solvent in which said solid precursor in the form of a precipitate and said phenolic dimer are insoluble, in particular in a linear or branched alkane with a boiling point greater than 50° C., in particular greater than 100° C., in particular in octane, and is subjected to said heat treatment, for the preparation of a mixture of giant p-(R)calixarenes the size of which is comprised from 21 to approximately 212 phenolic units.

The heat treatment is carried out under reflux of said organic solvent, with or without stirring, preferably without stirring of the reaction medium, and in particular has the effect on the one hand, of completing the formation of the macrocycles, in particular starting from linear oligomers comprised in the solid precursor in the form of a resin, but also of increasing the size of the macrocycles obtained starting equally well from the solid precursor in the form of a resin as from said dimer.

The giant calixarenes obtained comprise however a proportion of calix[7]arene and/or of calix[8]arene which is variable depending on R.

The more the solid precursor in the form of a resin or a dimer is insoluble in the organic solvent the more the proportion of giant calixarenes increases.

The duration of the heat treatment must also be controlled and must be comprised from 3 to 8 h depending on R and the base used.

Above 8 h, the proportion of small calixarenes obtained increases until only small calixarenes are obtained, the giant calixarenes disappearing by dissociating in favour of said small calixarenes.

Advantageously, the heat treatment is comprised from approximately 3 to 4 h.

Advantageously, when the heat treatment is comprised from 3 to 4 h, the base used is LiOH, KOH, NaOH, CsOH or RbOH.

Advantageously, the heat treatment is comprised from approximately 6 to 8 h, in particular 7 h.

Advantageously, when the heat treatment is comprised from approximately 6 to 8 h, in particular 7 h, the base used is $Ba(OH)_2$.

Depending on the solvent used for the heat treatment, the size of the macrocycles obtained can be modulated, the polarity of the solvent having an action both on the dissociation and on the reactivity of the chemical compounds.

The lower the temperature of the reaction mixture, the more the size of the macrocycles obtained decreases.

In an advantageous embodiment, the present invention relates to the use of at least one base in an aqueous solution with at least one phenol substituted in position 4 of formula (I), in which water is produced during the reaction, said water being retained in the reaction medium during said heating at a temperature comprised from 100 to 130° C. and a solid precursor, in the form of an optionally isolated precipitate is obtained, said solid precursor in the form of a precipitate being preceded by the formation of an optionally isolated phenolic dimer, as defined above, in which said solid precursor in the form of a precipitate or said phenolic dimer, optionally isolated from the aforesaid reaction medium, is placed in the presence of an organic solvent in which said solid precursor in the form of a precipitate and said phenolic dimer are at least partially soluble, in particular in xylene, toluene, DMSO or DMF and is subjected to said heat treatment, for the preparation of a mixture of giant p-(R)calixarenes the size of which is comprised from 21 to approximately 212 phenolic units.

The heat treatment is carried out under reflux of said organic solvent, with or without stirring, preferably without stirring of the reaction medium.

When the solid precursor in the form of a precipitate or the dimer are dissolved during the heat treatment stage, the macrocycles obtained are of greater purity with respect to those obtained in the absence of dissolution of the precursor in the form of a precipitate or of the dimer in the organic solvent; however, the proportion of small calixarenes and in particular of calix[7]arene and/or of calix[8]arene is greater.

The duration of the heat treatment must also be controlled and must be comprised from 3 to 8 h depending on R and the base used.

Above 8 h, the proportion of small calixarenes obtained increases until only small calixarenes are obtained, the giant calixarenes disappearing by dissociating in favour of said small calixarenes.

Advantageously, the heat treatment is comprised from approximately 3 to 4 h.

Advantageously, when the heat treatment is comprised from 3 to 4 h, the base used is LiOH, KOH, NaOH, CsOH or RbOH.

Advantageously, the heat treatment is comprised from approximately 6 to 8 h, in particular 7 h.

Advantageously, when the heat treatment is comprised from approximately 6 to 8 h, in particular 7 h, the base used is $Ba(OH)_2$.

Depending on the solvent used for the heat treatment with dissolution, the size of the macrocycles can be modulated.

The lower the temperature of the reaction mixture the smaller the size of the macrocycles obtained.

In an advantageous embodiment, the present invention relates to the use of at least one base in an aqueous solution with at least one phenol substituted in position 4 of formula (I), in which water is produced during the reaction, said water being retained in the reaction medium during said heating at a temperature comprised from 100 to 130° C. and a solid precursor, in the form of an optionally isolated precipitate is obtained, said solid precursor in the form of a precipitate being preceded by the formation of an optionally isolated phenolic dimer, as defined above, said solid precursor in the form of a precipitate or said phenolic dimer, optionally isolated from the aforesaid reaction medium, being placed in the presence of an organic solvent in which said solid precursor in the form of a precipitate and said phenolic dimer are insoluble, or of an organic solvent in which said solid precursor in the form of a precipitate and said phenolic dimer are at least partially soluble, and is subjected to said heat treatment, as defined above, in which the phenol substituted in position 4 of formula (I) is 4-benzyloxyphenol.

The heat treatment is carried out under reflux of said organic solvent, with or without stirring, preferably without stirring of the reaction medium.

It should be noted that this process with retention of water makes it possible to access calixarenes the size range of which is different from those obtained during the process with removal of the water during heating.

According to another aspect, the invention relates to a phenolic dimer substituted in position 4 of the following formula (II):

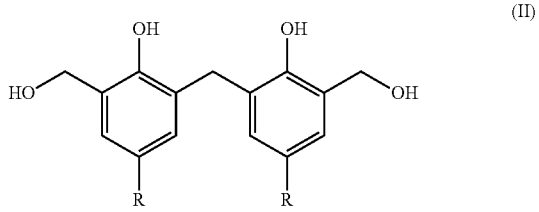

(II)

in which R is selected from:
a benzyl group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
a linear or branched $C_1$-$C_{20}$ alkyl group, excluding the t-butyl group,
a benzyloxy group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
a linear or branched $C_1$-$C_{20}$ alkyloxy group, a linear or branched PEG-1 to 10, the —OH end group of which is alkylated with a linear or branched $C_1$-$C_{20}$ alkyl,
a benzyl thioether group —S—$CH_2$-Ph optionally substituted in the ortho and/or para and/or meta position with one or more substituents selected from a halogen, SR' and OR', $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
a linear or branched $C_1$-$C_{20}$ alkyl thioether group, of formula —S—($C_1$-$C_{20}$-alkyl).

In the above, R can also represent:
an —$NR_aR_b$ group, $R_a$ and $R_b$ representing, independently of one another, a linear or branched $C_1$-$C_{20}$ alkyl,
a dibenzylamine group of formula —N(benzyl)$_2$, in which the two benzyl groups are, independently of one another, optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl.

In an advantageous embodiment, the present invention relates to a phenolic dimer substituted in position 4 of formula (II) as defined above, in which R is selected from:
a benzyloxy group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
a linear or branched $C_1$-$C_{20}$ alkyloxy group, a linear or branched PEG-1 to 10, the —OH end group of which is alkylated with a linear or branched $C_1$-$C_{20}$ alkyl.

In an advantageous embodiment, the present invention relates to a phenolic dimer substituted in position 4 of formula (II) as defined above, in which the linear or branched alkyl group or the linear or branched alkyloxy group is $C_5$-$C_{20}$.

In an advantageous embodiment, the present invention relates to a phenolic dimer substituted in position 4 of formula (II) as defined above, in which R is selected from the benzyloxy group, benzyl group, octyl group or octyoxy group.

According to another aspect, the present invention relates to a solid precursor in the form of a resin or a precipitate comprising a mixture of giant p-(R)calixarenes and phenolic oligomers of the following formula (III):

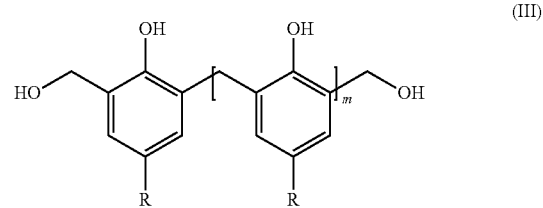

(III)

in which R is selected from:
a benzyl group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
a linear or branched $C_1$-$C_{20}$ alkyl group, excluding the t-butyl group,
a benzyloxy group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
a linear or branched $C_1$-$C_{20}$ alkyloxy group, a linear or branched PEG-1 to 10, the —OH end group of which is alkylated with a linear or branched $C_1$-$C_{20}$ alkyl,
a benzyl thioether group —S—$CH_2$-Ph optionally substituted in the ortho and/or para and/or meta position with one or more substituents selected from a halogen, SR' and OR', $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
a linear or branched $C_1$-$C_{20}$ alkyl thioether group, of formula —S—($C_1$-$C_{20}$-alkyl),
and m is an integer comprised from 2 to more than 200.

In the above, R can also represent:
an —$NR_aR_b$ group, $R_a$ and $R_b$ representing, independently of one another, a linear or branched $C_1$-$C_{20}$ alkyl,
a dibenzylamine group of formula —N(benzyl)$_2$, in which the two benzyl groups are, independently of one another, optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl.

In an advantageous embodiment, the present invention relates to a solid precursor in the form of a resin or a precipitate comprising a mixture of giant p-(R)calixarenes and phenolic oligomers of formula (III) as defined above, in which R is selected from:

- a benzyloxy group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
- a linear or branched $C_1$-$C_{20}$ alkyloxy group, a linear or branched PEG-1 to 10, the —OH end group of which is alkylated with a linear or branched $C_1$-$C_{20}$ alkyl.

Solid precursor in the form of a resin or a precipitate comprising a mixture of giant p-(R)calixarenes and phenolic oligomers of formula (III) as defined above, in which R is selected from:

- a benzyl group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
- a linear or branched $C_5$-$C_{20}$ alkyl group, excluding the t-butyl group,
- a benzyloxy group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
- a linear or branched $C_5$-$C_{20}$ alkyloxy group, a linear or branched PEG-1 to 10, the —OH end group of which is alkylated with a linear or branched $C_1$-$C_{20}$ alkyl.

According to another aspect, the present invention relates to a mixture of calixarenes of the following formula (IV):

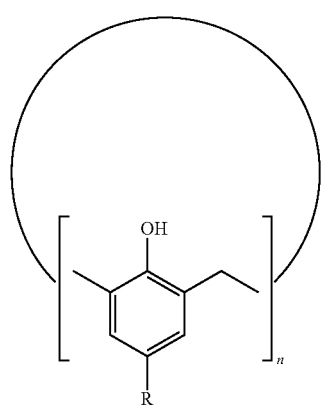

(IV)

in which n is an integer comprised from 21 to at most 220, in particular from 21 to 220, in particular from 21 to 212, more particularly from 21 to 200, R is selected from:

- a benzyl group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
- a linear or branched $C_1$-$C_{20}$ alkyl group, excluding the t-butyl group,
- a benzyloxy group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
- a linear or branched $C_1$-$C_{20}$ alkyloxy group, a linear or branched PEG-1 to 10, the —OH end group of which is alkylated with a linear or branched $C_1$-$C_{20}$ alkyl,
- a benzyl thioether group —S—$CH_2$-Ph optionally substituted in the ortho and/or para and/or meta position with one or more substituents selected from a halogen, SR' and OR', $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
- a linear or branched $C_1$-$C_{20}$ alkyl thioether group, of formula —S—($C_1$-$C_{20}$-alkyl).

In the above, R can also represent:

- an —$NR_aR_b$ group, $R_a$ and $R_b$ representing, independently of one another, a linear or branched $C_1$-$C_{20}$ alkyl,
- a dibenzylamine group of formula —N(benzyl)$_2$, in which the two benzyl groups are, independently of one another, optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl.

Said mixture of calixarenes of formula (IV), in a medium devoid of a base and under suitable conditions, in particular a temperature less than 100° C., is stable, i.e. the calixarenes of formula (IV) do not dissociate in favour of small calixarenes of the calix[6-8]arenes type over time, for example over a duration at least greater than 2 years.

In an advantageous embodiment, the present invention relates to a mixture of calixarenes of formula (IV) as defined above, with an average number of units n=approximately 100.

In an advantageous embodiment, the present invention relates to a mixture of calixarenes of formula (IV) in which n corresponds to a number of phenolic units of approximately 35.

In an advantageous embodiment, the present invention relates to a mixture of calixarenes of formula (IV) as defined above, in which R is selected from:

- a benzyloxy group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
- a linear or branched $C_1$-$C_{20}$ alkyloxy group, a linear or branched PEG-1 to 10, the —OH end group of which is alkylated with a linear or branched $C_1$-$C_{20}$ alkyl.

In an advantageous embodiment, the present invention relates to a mixture of calixarenes of formula (IV), as defined above, in which R is selected from:
- a benzyl group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
- a linear or branched $C_5$-$C_{20}$ alkyl group, excluding the t-butyl group,
- a benzyloxy group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
- a linear or branched $C_5$-$C_{20}$ alkyloxy group, a linear or branched PEG-1 to 10, the —OH end group of which is alkylated with a linear or branched $C_1$-$C_{20}$ alkyl.

In the above, R can also represent:
- an —$NR_aR_b$ group, $R_a$ and $R_b$ representing, independently of one another, a linear or branched $C_1$-$C_{20}$ alkyl,
- a dibenzylamine group of formula —$N(benzyl)_2$, in which the two benzyl groups are, independently of one another, optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl.

In an advantageous embodiment, the present invention relates to a mixture of calixarenes of formula (IV) as defined above, in which R is an octyloxy group and having a peak molar mass corresponding to 35 phenolic units according to GPC.

In an advantageous embodiment, the present invention relates to a mixture of calixarenes of formula (IV) as defined above, in which R is a benzyloxy group and the size determined by the centred Gaussian using GPC varies from 21 to approximately 212.

According to another aspect, the present invention relates to a process for the preparation of a mixture of giant p-(R)calixarenes the size of which is greater than 20, in particular from 21 to more than 220, in particular from 21 to approximately 220, in particular from 21 to approximately 212, more particularly from 21 to approximately 200, comprising a stage of bringing at least one base, in particular selected from barium hydroxide, rubidium hydroxide, lithium hydroxide, caesium hydroxide, potassium hydroxide or sodium hydroxide, into contact with at least one phenol substituted in position 4 of the following formula (I):

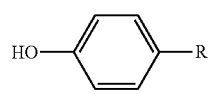

(I)

in which R is selected from:
- a benzyl group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
- a linear or branched $C_1$-$C_{20}$ alkyl group, excluding the t-butyl group,
- a benzyloxy group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
- a linear or branched $C_1$-$C_{20}$ alkyloxy group, a linear or branched PEG-1 to 10, the —OH end group of which is alkylated with a linear or branched $C_1$-$C_{20}$ alkyl,
- a benzyl thioether group —S—$CH_2$-Ph optionally substituted in the ortho and/or para and/or meta position with one or more substituents selected from a halogen, SR' and OR', $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
- a linear or branched $C_1$-$C_{20}$ alkyl thioether group, of formula —S—($C_1$-$C_{20}$-alkyl),
- an —$NR_aR_b$ group, $R_a$ and $R_b$ representing, independently of one another, a linear or branched $C_1$-$C_{20}$ alkyl,
- a dibenzylamine group of formula —$N(benzyl)_2$, in which the two benzyl groups are, independently of one another, optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl, and a source of aqueous formaldehyde,
in the absence or in the presence of an organic solvent, thus constituting a reaction medium,
said base being at a total concentration comprised from approximately 0.01 to 1 equivalent, in particular comprised from approximately 0.1 equivalent to approximately 0.4 equivalent, in particular equal to 0.15 or 0.4 equivalent, or 1 equivalent, with respect to said at least one phenol substituted in position 4 of formula (I),
said reaction medium being heated to a temperature comprised from 100 to 130° C., in order to obtain a heated reaction medium,
and comprising, optionally, after said heating, a stage of heat treatment of said heated reaction medium, in the presence of heat transfer means, in particular an oven or a liquid.

The term base denotes any base which is soluble in an aqueous medium of the metal hydroxide, tertiary amine, carbonate, sulphate, carboxylate type, for example.

It can also denote the use of an organic base of the amine type in combination with a metal salt (CsI for example).

The expression "source of aqueous formaldehyde" signifies that formaldehyde in an aqueous solution such as formalin or formol can be used.

The expression "in an aqueous solution" throughout the description signifies that the base is dissolved in a medium mainly constituted by water.

Advantageously, the expression "in an aqueous solution" denotes exclusively water.

The expression "in the absence or in the presence of an organic solvent" signifies that the reaction medium (which comprises water) is respectively devoid of or provided with solvents which are organic compounds which contain carbon atoms, the base as such, the formaldehyde or source of formaldehyde and phenol also not being considered as an organic solvent.

The expression "reaction medium" signifies the mixture of the different components, comprising the base(s), the phenol(s) substituted in position 4 of formula (I), and the source of formaldehyde, all being in an aqueous solution or in a water-organic solvent medium.

When said mixture has just been constituted, it is called an initial reaction medium, i.e. a reaction medium in which the reaction for the preparation of the p-(R)calixarenes has not yet been carried out, in particular before any heating of said mixture of the different compounds.

The heated reaction medium corresponds to the initial reaction medium which has been heated to a temperature comprised from 100 to 130° C. for approximately 30 minutes to 5 hours.

When the reaction for the preparation of the giant p-(R) calixarenes is carried out, in particular after heating said mixture of the different compounds, and heat treatment, the reaction medium is then called the final reaction medium.

The expression "and then optionally subjected to a heat treatment in the presence of heat transfer means" signifies that after said heating at a temperature comprised from 100 to 130° C., during which the water is optionally removed, the heat transfer means are applied to the reaction medium, then said reaction medium is heated again.

The heat transfer means are in particular an oven or a solvent, in particular a solvent heated at a temperature comprised from 120° C. to 140° C., for example a solvent the boiling point of which is comprised from 120° C. to 140° C.

By solvent is meant:
  a solvent, in particular an organic solvent, in which the organic compounds of the reaction medium are at least partially soluble, for example an aromatic solvent, with a boiling point greater than 50° C., in particular greater than 100° C.,
  or
  a liquid in which the organic compounds of the reaction medium are not soluble, for example a linear or branched alkane, in particular octane, or a silicone oil, with a boiling point greater than 50° C., in particular greater than 100° C.

By "solvent in which the organic compounds of the reaction medium are at least partially soluble" is meant a solvent that can optionally, depending on its nature, solubilize certain of the constituents of said reaction medium, disperse them (in order to form a colloidal suspension) or change some or all of them into a gel state.

Thus, when the heat transfer means are for example an oven or a solvent in which the organic compounds of the reaction medium are not soluble, said heat treatment takes place in a solid phase, preferably without stirring.

In an advantageous embodiment, the reaction medium is devoid of organic solvent, the water is removed during said heating at a temperature comprised from 100 to 130° C., and said heat treatment is carried out in the presence of a solvent in which the organic compounds of the reaction medium are at least partially soluble.

In another advantageous embodiment, the reaction medium is devoid of organic solvent, the water is removed during said heating at a temperature comprised from 100 to 130° C., and said heat treatment is carried out in the presence of a solvent in which the organic compounds of the reaction medium are not soluble.

In another advantageous embodiment, the reaction medium is devoid of organic solvent, the water is not removed during said heating at a temperature comprised from 100 to 130° C., and said heat treatment is carried out in the presence of a solvent in which the organic compounds of the reaction medium are at least partially soluble.

In another advantageous embodiment, the reaction medium is devoid of organic solvent, the water is not removed during said heating at a temperature comprised from 100 to 130° C., and said heat treatment is carried out in the presence of a solvent in which the organic compounds of the reaction medium are not soluble.

In another advantageous embodiment, the reaction medium comprises, besides water, an organic solvent, the water is not removed during heating, and said reaction medium is not subjected to said additional heat treatment.

In another advantageous embodiment, the reaction medium comprises, besides water, an organic solvent, the water is not removed during heating, and said reaction medium is subjected to said additional heat treatment, the water being in particular removed during said heat treatment.

The water-organic solvent system is capable of promoting solubilization of all of the organic and inorganic compounds, at the start of the reaction. This therefore makes it possible to maintain the constituents of the reaction medium for longer in solution. This results in a better consumption of reagents, which leads to 1) a better yield, and 2) less by-products (starting products, reaction intermediates etc.). This makes purification easier.

The present invention also relates to a process for the preparation of a mixture of giant p-(R)calixarenes the size of which is greater than 20, in particular from 21 to more than 220, in particular from 21 to approximately 220, in particular from 21 to approximately 212, more particularly from 21 to approximately 200,
comprising a stage of bringing at least one base, in particular selected from barium hydroxide, rubidium hydroxide, lithium hydroxide, caesium hydroxide, potassium hydroxide or sodium hydroxide, into contact with at least one phenol substituted in position 4 of the following formula (I):

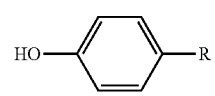

(I)

in which R is selected from:
  a benzyl group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
  a linear or branched $C_1$-$C_{20}$ alkyl group, excluding the t-butyl group,
  a benzyloxy group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, P(O)OR$_a$OR$_b$, R$_a$ and R$_b$ representing, independently of one another, a linear or branched C$_1$-C$_{20}$ alkyl, a linear or branched C$_1$-C$_{20}$ alkyloxy group, a linear or branched PEG-1 to 10, the —OH end group of which is alkylated with a linear or branched C$_1$-C$_{20}$ alkyl, a benzyl thioether group —S—CH$_2$-Ph optionally substituted in the ortho and/or para and/or meta position with one or more substituents selected from a halogen, SR' and OR', NR$_a$R$_b$, PR$_a$R$_b$, P(O)R$_a$R$_b$, P(O)OR$_a$OR$_b$, R$_a$ and R$_b$ representing, independently of one another, a linear or branched C$_1$-C$_{20}$ alkyl, a linear or branched C$_1$-C$_{20}$ alkyl thioether group, of formula —S—(C$_1$-C$_{20}$-alkyl), and a source of aqueous formaldehyde, in the absence of an organic solvent, thus constituting a reaction medium, said base being at a total concentration comprised from approximately 0.01 to 1 equivalent, in particular comprised from approximately 0.1 equivalent to approximately 0.4 equivalent, in particular equal to 0.15 or 0.4 equivalent, or 1 equivalent, with respect to said at least one phenol substituted in position 4 of formula (I), said reaction medium being heated to a temperature comprised from 100 to 130° C., in order to obtain a heated reaction medium, and comprising, optionally, after said heating, a stage of heat treatment of said heated reaction medium, in the presence of an organic solvent.

The expression "in the absence of an organic solvent" signifies that the reaction medium is devoid of solvents which are organic compounds which contain carbon atoms, the base as such, the formaldehyde or source of formaldehyde and phenol also not being considered as an organic solvent.

The expression "reaction medium" signifies the mixture of the different components, comprising the base(s), the phenol(s) substituted in position 4 of formula (I), the source of formaldehyde, all being in an aqueous solution.

In an advantageous embodiment, the present invention relates to a process for the preparation of a mixture of giant p-(R)calixarenes as defined above, in which R is selected from:

a benzyloxy group optionally substituted in the ortho and/or para and/or meta position with one or more substituents selected from a halogen, SR' and OR', R' representing a linear or branched C$_1$-C$_{20}$ alkyl chain, a C$_3$ to C$_{20}$ cycloalkyl group, NR$_a$R$_b$, PR$_a$R$_b$, P(O)R$_a$R$_b$, P(O)OR$_a$OR$_b$, R$_a$ and R$_b$ representing, independently of one another, a linear or branched C$_1$-C$_{20}$ alkyl, a linear or branched C$_1$-C$_{20}$ alkyloxy group, a linear or branched PEG-1 to 10, the —OH end group of which is alkylated with a linear or branched C$_1$-C$_{20}$ alkyl.

In an advantageous embodiment, the present invention relates to a process for the preparation of a mixture of giant p-(R)calixarenes as defined above, in which R is selected from:

a benzyl group optionally substituted in the ortho and/or para and/or meta position with one or more substituents selected from a halogen, SR' and OR', R' representing a linear or branched C$_1$-C$_{20}$ alkyl chain, a C$_3$ to C$_{20}$ cycloalkyl group, NR$_a$R$_b$, PR$_a$R$_b$, P(O)R$_a$R$_b$, P(O)OR$_a$OR$_b$, R$_a$ and R$_b$ representing, independently of one another, a linear or branched C$_1$-C$_{20}$ alkyl, a linear or branched C$_5$-C$_{20}$ alkyl group, excluding the t-butyl group, a benzyloxy group optionally substituted in the ortho and/or para and/or meta position with one or more substituents selected from a halogen, SR' and OR', R' representing a linear or branched C$_1$-C$_{20}$ alkyl chain, a C$_3$ to C$_{20}$ cycloalkyl group, NR$_a$R$_b$, PR$_a$R$_b$, P(O)R$_a$R$_b$, P(O)OR$_a$OR$_b$, R$_a$ and R$_b$ representing, independently of one another, a linear or branched C$_1$-C$_{20}$ alkyl, a linear or branched C$_5$-C$_{20}$ alkyloxy group, a linear or branched PEG-1 to 10, the —OH end group of which is alkylated with a linear or branched C$_1$-C$_{20}$ alkyl.

In an advantageous embodiment, the present invention relates to a process for the preparation of a mixture of giant p-(R)calixarenes as defined above, in which the water produced during the reaction is removed from said reaction medium during said heating and a solid precursor in the form of an optionally isolated, hard brittle resin is obtained.

In an advantageous embodiment, the present invention relates to a process for the preparation of a mixture of giant p-(R)calixarenes, the water produced during the reaction being removed from said reaction medium during said heating and a solid precursor in the form of an optionally isolated, hard brittle resin being obtained, as defined above, in which said solid precursor in the form of a hard brittle resin is preceded by the formation of an optionally isolated phenolic dimer.

In this embodiment, the process leads intermediately to the production of an oligomer of formula (III) and then to a phenolic dimer of formula (II) which can be isolated or not isolated.

The production of said oligomer is carried out at the end of heating at a temperature comprised from 100 to 130° C. for 10 to 25 minutes and the production of the dimer is carried out at the end of heating at a temperature comprised from 100 to 130° C. for a period of time comprised from 30 minutes to 2 h starting from an initial reaction medium.

If heating at a temperature comprised from 100 to 130° C. is continued for a period of time comprised from 1 to 3 h without isolating the dimer obtained, a hard brittle resin is then obtained.

In this case, a proportion of the water present after the production of the resin is less than 5% by weight In an advantageous embodiment, the present invention relates to a process for the preparation of a mixture of giant p-(R)calixarenes, the water produced during the reaction being removed from said reaction medium during said heating, a solid precursor in the form of an optionally isolated, hard brittle resin being obtained, said solid precursor in the form of a hard brittle resin being preceded by the formation of an optionally isolated phenolic dimer, as defined above, in which said solid precursor in the form of a hard brittle resin is isolated from the aforesaid reaction medium and not subjected to heat treatment.

In an advantageous embodiment, the present invention relates to a process for the preparation of a mixture of giant p-(R)calixarenes, the water produced during the reaction being removed from said reaction medium during said heating, a solid precursor in the form of an optionally isolated, hard brittle resin being obtained, said solid precursor in the form of a hard brittle resin being preceded by the formation of an optionally isolated phenolic dimer, as defined above, in which said solid precursor in the form of a hard brittle resin is isolated from the aforesaid reaction medium and not subjected to heat treatment in the presence of an organic solvent.

The product obtained in these embodiments is 50% to 90% constituted by giant p-(R)calixarenes (depending on the precise nature of the R group, the base and the concentration) optionally comprising said residual dimer and/or said residual oligomers.

Depending on R, the product obtained requires purification or does not.

In an advantageous embodiment, the present invention relates to a process for the preparation of a mixture of giant p-(R)calixarenes, the water produced during the reaction being removed from said reaction medium during said heating, a solid precursor in the form of an optionally isolated, hard brittle resin being obtained, said solid precursor in the form of a hard brittle resin being preceded by the formation of an optionally isolated phenolic dimer, said solid precursor in the form of a hard brittle resin being isolated from the aforesaid reaction medium and not subjected to heat treatment in the presence of an organic solvent, as defined above,
comprising the following stages:
  a. bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I),
    with aqueous formaldehyde, in order to constitute a reaction medium and heating said reaction medium for a period of time comprised from 20 minutes to 2 hours, in particular 1 hour, while removing the water formed,
    in order to obtain a dimer of formula (II) as defined above,
  b. optionally continuing the heating of said reaction medium containing said dimer for 1 to 3 hours while removing the water formed in order to obtain a reaction medium containing a solid precursor, in the form of a hard brittle resin,
  c. optionally, after neutralization of the base, washing of said solid precursor with a polar solvent, in particular methanol, in order to obtain a washed mixture of giant calixarenes, in which R is as defined above, in neutralized form.
  d. optionally the recrystallization of said washed mixture of giant calixarenes, from a solvent based on DMSO, in order to obtain a purified mixture of giant calixarenes in which R is as defined above, and substantially devoid of p-(R)calix[7]arene and/or of p-(R)calix[8]arene.
  e. optionally, the purification of said purified mixture of giant calixarenes devoid of p-(R)calix[7]arene and/or p-(R)calix[8]arene using GPC, by separating different fractions depending on their elution time. In stage a, at the end of 10 to 25 minutes, there is the appearance of the oligomers or polymers of formula (III) which then leads, with more prolonged heating, to the dimer of formula (II).

The heating is carried out at a temperature of approximately 100 to 130° C.

Advantageously, heating is at approximately 110° C., 120° C. or 130° C.

If the dimer is the desired product, it is then recovered by filtration of the reaction medium.

In stage b., the heating is continued at a temperature of approximately 100 to 130° C., if the dimer is not the desired product, which leads to said precursor in the form of a hard brittle resin. Advantageously, the heating is continued for 1 h, 2 h or 3 h and at a temperature comprised from 100° C. to 130° C., advantageously at 110° C., 120° C. or 130° C.

In stage c., the solid precursor in the form of a hard brittle resin, obtained after neutralization with an acid such as HCl or $H_2SO_4$, in particular HCl dilute or not dilute, is 50 to 90% constituted by giant p-(R)calixarenes which can also comprise other by-products such the residual oligomers or the residual dimer, but also p-(R)calix[7]arene and/or p-(R)calix[8]arene.

A first purification stage consists of a washing with a polar solvent, for example methanol, which makes it possible to partially purify said precursor and in particular to remove certain residual linear oligomers or the residual dimer.

In stage d., the recrystallization from a mixture based on DMSO makes it possible to complete the purification, in particular by removing the p-(R)calix[7]arene and/or p-(R)calix[8]arene.

The solvent mixture based on DMSO is in particular a mixture of DMSO with toluene or acetone, DMSO being in a proportion of 5% to 50% by volume in the solvent mixture, in particular 10%.

The DMSO can be replaced by an aprotic polar solvent, preferably DMF.

Stage e. is carried out in order to separate the mixture of purified giant p-(R)calixarenes devoid of p-(R)calix[7]arene and/or p-(R)calix[8]arene into fractions of giant p-(R)calixarenes of different sizes.

In an advantageous embodiment, the base used in stage a. is $Ba(OH)_2$ and R represents octyloxy. The mixture of giant p-(R)calixarenes obtained is p-(octyloxy)calix[21-50]arenes and the size determined by the centred Gaussian using GPC corresponds to approximately 35 phenolic units (peak size).

In an advantageous embodiment, the present invention relates to a process for the preparation of a mixture of giant p-(R)calixarenes, the water produced during the reaction being removed from said reaction medium during said heating, a solid precursor in the form of an optionally isolated, hard brittle resin being obtained, said solid precursor in the form of a hard brittle resin being preceded by the formation of an optionally isolated phenolic dimer, as defined above,
in which said phenolic dimer or said solid precursor in the form of a hard brittle resin, contained in said reaction medium, is placed in the presence of heat transfer means in the form of an oven or of a solvent, in particular a solvent in which said solid precursor in the form of a hard brittle resin, and said phenolic dimer, are insoluble, in particular in a linear or branched alkane with a boiling point greater than 50° C., in particular greater than 100° C., in particular octane, and is subjected to a heat treatment.

In an advantageous embodiment, the present invention relates to a process for the preparation of a mixture of giant p-(R)calixarenes, the water produced during the reaction being removed from said reaction medium during said heating, a solid precursor in the form of an optionally isolated, hard brittle resin being obtained, said solid precursor in the form of a hard brittle resin being preceded by the formation of an optionally isolated phenolic dimer, as defined above,
in which said phenolic dimer or said solid precursor in the form of a hard brittle resin, contained in said reaction medium, is placed in the presence of an organic solvent, in particular an organic solvent in which said solid precursor in the form of a hard brittle resin, and said phenolic dimer, are insoluble, in particular in a linear or branched alkane with a boiling point greater than 50° C., in particular greater than 100° C., in particular octane, and is subjected to a heat treatment.

The organic solvent can be any organic solvent provided that, on the one hand, it does not react with the precursor in the form of a resin and that, on the other hand, said precursor in the form of a resin is insoluble therein.

The boiling point of an organic solvent is in particular greater than or equal to 110° C.

The heat treatment is carried out under reflux of said organic solvent, with or without stirring, preferably without stirring of the reaction medium, for a period of time comprised from 3 to 8 h depending on R and the base, and in particular has the effect on the one hand, of completing the formation of the macrocycles, in particular those comprised in the solid precursor in the form of a resin, but also of increasing the size of the macrocycles obtained starting equally well from the solid precursor in the form of a resin as from said dimer.

The giant calixarenes obtained comprise however a proportion of calix[7]arenes and/or calix[8]arenes which is variable depending on R, the concentration of base, the nature of the base and the temperature, accompanied by a variable proportion of dimer/linear oligomers.

The more insoluble the solid precursor in the form of a resin or a dimer in the organic solvent, the more the proportion of giant calixarenes increases.

The duration of the heat treatment must also be controlled and must be comprised from 3 to 8 h depending on R and the base used.

Above 8 h, the proportion of small calixarenes obtained increases until only small calixarenes are obtained, the giant calixarenes disappearing by dissociating in favour of said small calixarenes.

Depending on the solvent used for the heat treatment, the size of the macrocycles obtained can be modulated.

The lower the temperature of the reaction mixture, the more the size of the macrocycles obtained decreases.

In an advantageous embodiment, the present invention relates to a process for the preparation of a mixture of giant p-(R)calixarenes, the water produced during the reaction being removed from said reaction medium during said heating, a solid precursor in the form of an optionally isolated, hard brittle resin being obtained, said solid precursor in the form of a hard brittle resin being preceded by the formation of an optionally isolated phenolic dimer, said phenolic dimer or said solid precursor in the form of a hard brittle resin, contained in said reaction medium, being placed in the presence of heat transfer means in the form of an oven or of a solvent, in particular a solvent in which said solid precursor in the form of a hard brittle resin, and said phenolic dimer, are insoluble, in particular in a linear or branched alkane with a boiling point greater than 50° C., in particular greater than 100° C., in particular octane, or a silicone oil and is subjected to a heat treatment, as defined above, comprising the following stages:

a. bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I), with aqueous formaldehyde, in order to constitute a reaction medium and heating said reaction medium for a period of time comprised from 30 minutes to 2 hours, in particular 1 hour while removing the water formed, in order to obtain a dimer of formula (II) as defined above, b. optionally continuing the heating of said reaction medium containing said dimer while removing the water formed in order to obtain a reaction medium containing a solid precursor, in the form of a hard brittle resin, for 1 to 5 hours, the duration being variable depending on the concentration of the base used, and optionally filtration of said solid precursor, in the form of a hard brittle resin, c. heating said reaction medium using heat transfer means in the form of an oven, or the addition to said reaction medium containing said solid precursor in the form of a hard brittle resin of a solvent in which said solid precursor in the form of a hard brittle resin is insoluble, in particular in a linear or branched alkane with a boiling point greater than 50° C., in particular greater than 100° C., in particular greater than or equal to 110° C., in particular octane or a silicone oil, in order to obtain a reaction medium containing a solid in the form of a hard brittle resin, in an oven or a solvent and heating said reaction medium containing a solid in the form of a hard brittle resin, for 3 to 8 hours, in order to obtain a mixture of giant calixarenes in which R is as defined above, further comprising, a p-(R)calix[7]arene and/or a p-(R)calix[8]arene, d. recrystallization, after neutralization of the base, of said mixture of giant calixarenes, from a solvent based on DMSO, in order to obtain a purified mixture of giant calixarenes in which R is as defined above, substantially devoid of p-(R)calix 7]arene and/or p-(R)calix 8]arene.

e. optionally, purification using GPC, by separating different fractions depending on their elution time.

In an advantageous embodiment, the present invention relates to a process for the preparation of a mixture of giant p-(R)calixarenes, the water produced during the reaction being removed from said reaction medium during said heating, a solid precursor in the form of an optionally isolated, hard brittle resin being obtained, said solid precursor in the form of a hard brittle resin being preceded by the formation of an optionally isolated phenolic dimer, said phenolic dimer or said solid precursor in the form of a hard brittle resin, contained in said reaction medium, being placed in the presence of an organic solvent, in particular an organic solvent in which said solid precursor in the form of a hard brittle resin, and said phenolic dimer, are insoluble, in particular in a linear or branched alkane with a boiling point greater than 50° C., in particular greater than 100° C., in particular octane, or a silicone oil and being subjected to a heat treatment, as defined above, comprising the following stages:

a. bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I), with aqueous formaldehyde, in order to constitute a reaction medium and heating said reaction medium for a period of time comprised from 30 minutes to 2 hours, in particular 1 hour while removing the water formed, in order to obtain a dimer of formula (II) as defined above, b. optionally continuing the heating of said reaction medium containing said dimer while removing the water formed in order to obtain a reaction medium containing a solid precursor, in the form of a hard brittle resin, for 1 to 5 hours, the duration being variable, depending on the concentration of base used, and optionally filtration of said solid precursor, in the form of a hard brittle resin, c. the addition to said reaction medium containing said solid precursor in the form of a hard brittle resin, of an organic solvent in which said solid precursor in the form of a hard brittle resin is insoluble, in particular in a linear or branched alkane with a boiling point greater than 50° C., in particular greater than 100° C., in particular greater than 110° C., in particular octane or a silicone oil, in order to obtain a reaction medium containing a solid in the form of a hard brittle resin, in a solvent and heating said reaction medium containing a solid in the form of a hard brittle resin, for 3 to 8 hours,
   in order to obtain a mixture of giant calixarenes in which R is as defined above, further comprising, a p-(R)calix[7]arene and/or a p-(R)calix[8]arene,
d. recrystallization, after neutralization of the base, of said mixture of giant calixarenes, from a solvent based on DMSO, in order to obtain a purified mixture of giant calixarenes in which R is as defined above, substantially devoid of p-(R)calix 7]arene and/or p-(R)calix 8]arene.
e. optionally, purification using GPC, by separating different fractions depending on their elution time.

In stage a., at the end of 10 to 25 minutes, there is the appearance of the oligomers or polymers of formula (III) which then leads, with more prolonged heating, to the dimer of formula (II).

The heating is carried out at a temperature of approximately 100 to 130° C. for 30 minutes to 2 h starting from an initial reaction medium in order to form the dimer of formula (II)

Advantageously, the heating is at approximately 110° C., 120° C. or 130° C.

If the dimer is the desired product, it is then recovered by filtration of the reaction medium.

In stage b., the heating is continued at a temperature of approximately 100 to 130° C., if the dimer is not the desired product, this leads to said precursor in the form of a hard brittle resin. Advantageously, the heating is continued for 1 h, 2 h or 3 h and at a temperature comprised from 100° C. to 130° C., advantageously at 110° C., 120° C. or 130° C.

The mixture obtained in stage b. is approximately 50% to 90% constituted by giant p-(R)calixarenes, depending on the R group, and can be isolated by simple filtration.

In stage c., either the solvent is introduced directly into the reaction medium of the preceding stage b., or said solid precursor in the form of a hard brittle resin is introduced into an apparatus for carrying out a reaction and the organic solvent into which said solid precursor in the form of a hard, brittle and insoluble resin is introduced, thus constituting the reaction medium.

In particular, the heat treatment is carried out under reflux of said organic solvent, with or without stirring, preferably without stirring of the reaction medium.

The heat treatment makes it possible to complete the formation of the macrocycles and to increase the size of the giant p-(R)calixarenes.

Advantageously, the heat treatment is comprised from approximately 3 to 4 h.

Advantageously, when the heat treatment is comprised from 3 to 4 h, the base used is LiOH, KOH, NaOH, CsOH or RbOH.

Advantageously, the heat treatment is comprised from approximately 6 to 8 h, in particular 7 h.

Advantageously, when the heat treatment is comprised from approximately 6 to 8 h, in particular 7 h, the base used is $Ba(OH)_2$.

In stage d, the solvent mixture based on DMSO is in particular a mixture of DMSO with toluene or acetone, DMSO being in a proportion from 5% to 50% by volume in the solvent mixture, in particular 10%.

The DMSO can be replaced by an aprotic polar solvent, preferably DMF.

Stage e. is carried out in order to separate the purified mixture of giant p-(R)calixarenes devoid of p-(R)calix[7]arene and/or of p-(R)calix[8]arene into fractions of giant p-(R)calixarenes of different sizes.

In an advantageous embodiment, the base used in stage a. is $Ba(OH)_2$, LiOH, KOH, NaOH, CsOH or RbOH and R represents benzyloxy.

The mixture of giant p-(R)calixarenes obtained is p-(benzyloxy)calix[21-60]arenes depending on the base used and different experiments, and the size determined by the centred Gaussian using GPC depends in particular on the base used, its concentration and reaction times; the centred Gaussian corresponds for example to approximately 30 phenolic units, with 0.4 equivalent of KOH, and octane as the solvent during heat treatment.

In an advantageous embodiment, the present invention relates to a process for the preparation of a mixture of giant p-(R)calixarenes, the water produced during the reaction being removed from said reaction medium during said heating, a solid precursor in the form of an optionally isolated, hard brittle resin being obtained, said solid precursor in the form of a hard brittle resin being preceded by the formation of an optionally isolated phenolic dimer, as defined above,
in which said phenolic dimer or said solid precursor in the form of a hard brittle resin, contained in said reaction medium, is placed in the presence of an organic solvent, in particular an organic solvent in which said solid precursor in the form of a hard brittle resin, and said phenolic dimer, are at least partially soluble, in particular in xylene, toluene, DMSO or DMF, and is subjected to a heat treatment. In fact, dispersion of the solid precursor in the form of a hard brittle resin, and of the phenolic dimer is complete, in particular under vigorous stirring, but a precipitate remains therein. that can be constituted by calix[8]arene and/or calix[21-220] arenes.

When the solid precursor in the form of a resin or the dimer is dissolved for the heat treatment stage, the macrocycles obtained are of greater purity than when no solid precursor in the form of a resin or the dimer is dissolved in the organic solvent; however, the proportion of small calixarenes present and in particular of calix[7]arenes and/or of calix[8]arenes is greater.

The heat treatment is carried out under reflux of said organic solvent, with or without stirring, preferably with stirring of the reaction medium.

The duration of the heat treatment must also be controlled and must be comprised from 3 to 8 h depending on R and the base used.

Above 8 h, the proportion of small calixarenes obtained increases until only small calixarenes are obtained, the giant calixarenes disappearing by dissociating in favour of said small calixarenes.

Depending on the solvent used for the heat treatment with dissolution, the size of the macrocycles obtained can be modulated.

The lower the temperature of the reaction mixture, the more the size of the macrocycles obtained decreases.

For example, a mixture of giant p-(R)calixarenes obtained has a size determined by the centred Gaussian using GPC, of approximately 30 phenolic units.

In an advantageous embodiment, the present invention relates to a process for the preparation of a mixture of giant p-(R)calixarenes, the water produced during the reaction being removed from said reaction medium during said heating, a solid precursor in the form of an optionally isolated, hard brittle resin being obtained, said solid precursor in the form of a hard brittle resin being preceded by the formation of an optionally isolated phenolic dimer, said phenolic dimer or said solid precursor in the form of a hard brittle resin, contained in said reaction medium, being placed in the presence of an organic solvent, in particular an organic solvent in which said solid precursor in the form of a hard brittle resin and said phenolic dimer are at least partially soluble, in particular in xylene, toluene, DMSO or DMF, and being subjected to a heat treatment, as defined above, comprising the following stages:

a. bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I),
   with aqueous formaldehyde, in order to constitute a reaction medium and heating said reaction medium for a period of time comprised from 30 minutes to 2 hours, in particular 1 hour, while removing the water formed,
   in order to obtain a dimer of formula (II) as defined above, b. optionally continuing the heating of said reaction medium containing said dimer while removing the water formed in order to obtain a reaction medium containing a solid precursor, in the form of a hard brittle resin, for 1 to 3 hours, and optionally filtration of said solid precursor in the form of a hard brittle resin, c. the addition to said reaction medium containing said solid precursor in the form of a hard brittle resin, of an organic solvent in which said solid precursor in the form of a hard brittle resin is at least partially soluble, in particular xylene or toluene, DMSO or DMF, in order to obtain a reaction medium containing a solid, in the form of a hard brittle resin, introduced into a solvent and heating of said reaction medium containing a solid in the form of a dissolved resin, for 3 to 8 hours,
   in order to obtain a mixture of giant calixarenes in which R is as defined above, further comprising, a p-(R)calix[7]arene and/or a p-(R)calix[8]arene, d. recrystallization, after neutralization of the base, of said mixture of giant calixarenes, from a solvent based on DMSO, in order to obtain a purified mixture of giant calixarenes in which R is as defined above, substantially devoid of p-(R)calix[7]arene and/or p-(R)calix[8]arene.

e. optionally purification using GPC, by separating different fractions depending on their elution time.

In stage a., at the end of 10 to 25 minutes, there is the appearance of the oligomers or polymers of formula (III) which then leads, with more prolonged heating, to the dimer of formula (II).

The heating is carried out at a temperature of approximately 100 to 130° C. for 30 minutes to 2 h starting from the initial reaction medium in order to form the dimer of formula (II)

Advantageously, the heating is at approximately 110° C., 120° C. or 130° C.

If the dimer is the desired product, it is then recovered by filtration of the reaction medium.

In stage b., the heating is continued at a temperature of approximately 100 to 130° C., if the dimer is not the desired product, which leads to said precursor in the form of a hard brittle resin. Advantageously, the heating is continued for 1 h, 2 h or 3 h and at a temperature comprised from 100° C. to 130° C., advantageously at 110° C., 120° C. or 130° C.

The mixture obtained in stage b. is approximately 50% to 90% constituted by giant p-(R)calixarenes, depending on the nature of the R group, and can be isolated by simple filtration.

In stage c., the heat treatment makes it possible to complete the formation of the macrocycles and to increase the size of giant p-(R)calixarenes.

Advantageously, the heat treatment is comprised from approximately 3 to 4 h.

Advantageously, when the heat treatment is comprised from 3 to 4 h, the base used is LiOH, KOH, NaOH, CsOH or RbOH.

Advantageously, the heat treatment is comprised from approximately 6 to 8 h, in particular 7 h.

Advantageously, when the heat treatment is comprised from approximately 6 to 8 h, in particular 7 h, the base used is $Ba(OH)_2$.

In stage d., the solvent mixture based on DMSO is in particular a mixture of DMSO with toluene or acetone, DMSO being in a proportion of 5% to 50% by volume in the solvent mixture, in particular 10%.

The DMSO can be replaced by an aprotic polar solvent, preferably DMF.

Stage e. is carried out in order to separate the purified mixture of giant p-(R)calixarenes devoid of p-(R)calix[7]arene and/or p-(R)calix[8]arene into fractions of giant p-(R) calixarenes of different sizes. In an advantageous embodiment, the base used in stage a. is $Ba(OH)_2$, LiOH, KOH, NaOH, CsOH or RbOH and R represents benzyloxy.

The mixture of giant p-(R)calixarenes obtained is p-(benzyloxy)calix[21-50]arenes and the size determined by the centred Gaussian using GPC is approximately 30.

In an advantageous embodiment, the present invention relates to a process for the preparation of a mixture of giant p-(R)calixarenes, the water produced during the reaction being removed from said reaction medium during said heating, as defined above, in which said phenolic dimer is isolated, then subjected to a heat treatment as described above and to a recrystallization as defined in stages c. and d. above.

When the dimer is isolated in the neutral form, a base, in particular the base having been used in order to obtain said dimer, more particularly at the concentration used in order to obtain said dimer, is added prior to the heat treatment.

When the dimer is isolated in the form of a salt, the addition of a base is not necessary.

Said isolated dimer is then placed in the presence of an organic solvent, in particular an organic solvent in which said phenolic dimer is soluble or insoluble, as defined above, and is subjected to the heat treatment as above.

In an advantageous embodiment, the present invention relates to a process for the preparation of a mixture of giant p-(R)calixarenes, the water produced during the reaction being removed from said reaction medium during said heating, as defined above,
in which said solid precursor in the form of a hard brittle resin preceded by the formation of a phenolic dimer, is isolated and placed in the presence of heat transfer means in the form of an oven or of a solvent in which said solid precursor in the form of a hard brittle resin is insoluble, then subjected to a heat treatment and to a recrystallization as defined in stages c. and d. above.

Said solid precursor in the form of an isolated hard brittle resin is thus placed in the presence of heat transfer means in the form of an oven or of a solvent in which said phenolic dimer is soluble or insoluble, as defined above, and is subjected to the heat treatment as above.

In an advantageous embodiment, the present invention relates to a process for the preparation of a mixture of giant p-(R)calixarenes, the water produced during the reaction being removed from said reaction medium during said heating, as defined above,
in which said solid precursor in the form of a hard brittle resin preceded by the formation of a phenolic dimer, is isolated and placed in the presence of an organic solvent in which said solid precursor in the form of a hard brittle resin is insoluble, then subjected to a heat treatment and to a recrystallization as defined in stages c. and d. above.

Said solid precursor in the form of an isolated hard brittle resin is then placed in the presence of an organic solvent, in particular an organic solvent in which said phenolic dimer is soluble or insoluble, as defined above, and is subjected to the heat treatment as above.

In an advantageous embodiment, the present invention relates to a process for the preparation of a mixture of giant p-(R)calixarenes the size of which is greater than 20, in particular from 21 to more than 220, in particular from 21 to 220, in particular from 21 to 212, more particularly from 21 to approximately 200, even more particularly from 21 to approximately 100, comprising a stage of bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I), as defined above,
in which the water produced during the reaction is retained in said reaction medium during said heating at a temperature comprised from 100 to 130° C. and a solid precursor in the form of an optionally isolated precipitate is obtained.

In this embodiment, the water formed during the reaction is not removed but retained in the reaction medium.

The consequence of this is that the reaction medium does not solidify completely but on the contrary a precipitate is obtained. The precipitate in the same manner as the hard brittle resin can be isolated by simple filtration.

In an advantageous embodiment, the present invention relates to a process for the preparation of a mixture of giant p-(R)calixarenes the size of which is greater than 20, in particular from 21 to more than 220, in particular from 21 to 220, in particular from 21 to 212, more particularly from 21 to approximately 200, even more particularly from 21 to approximately 100, comprising a stage of bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I), the water produced during the reaction being retained in said reaction medium during said heating, a solid precursor in the form of an optionally isolated precipitate being obtained, as defined above,
in which said solid precursor in the form of a precipitate is preceded by the formation of an optionally isolated phenolic dimer.

In this embodiment, the process leads intermediately to the production of an oligomer of formula (III) and then to a phenolic dimer of formula (II) which can be isolated or not isolated.

The production of said oligomer is carried out at the end of heating at a temperature comprised from 100 to 130° C. for 10 to 25 minutes and the production of the dimer is carried out at the end of heating at a temperature comprised from 100 to 130° C. for a period of time comprised from 30 minutes to 2 h starting from an initial reaction medium.

If heating at a temperature comprised from 100 to 130° C. is continued for a period of time comprised from 1 to 3 h without isolating the dimer obtained, a hard brittle resin is then obtained.

In an advantageous embodiment, the present invention relates to a process for the preparation of a mixture of giant p-(R)calixarenes the size of which is greater than 20, in particular from 21 to more than 220, in particular from 21 to 220, in particular from 21 to 212, more particularly from 21 to approximately 200, even more particularly from 21 to approximately 100, comprising a stage of bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I), the water produced during the reaction being retained in said reaction medium during said heating, a solid precursor in the form of an optionally isolated precipitate being obtained, as defined above,
in which said solid precursor in the form of a precipitate is isolated from the aforesaid reaction medium and not subjected to heat treatment.

In an advantageous embodiment, the present invention relates to a process for the preparation of a mixture of giant p-(R)calixarenes the size of which is greater than 20, in particular from 21 to more than 220, in particular from 21 to 220, in particular from 21 to 212, more particularly from 21 to approximately 200, even more particularly from 21 to approximately 100, comprising a stage of bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I), the water produced during the reaction being retained in said reaction medium during said heating, a solid precursor in the form of an optionally isolated precipitate being obtained, as defined above,
in which said solid precursor in the form of a precipitate is isolated from the aforesaid reaction medium and not subjected to heat treatment in the presence of an organic solvent.

The product obtained in the precipitate is therefore essentially constituted by giant p-(R)calixarenes and does not necessarily require heat treatment in order to complete the formation of the macrocycles (giant p-(R)calixarenes).

The giant p-(R)calixarenes are smaller in size when the water is retained with respect to the embodiment with removal of the water.

The product obtained in this embodiment is 50 to 90% constituted by giant p-(R)calixarenes optionally comprising said residual dimer and/or said residual oligomers.

Depending on R, the product obtained requires purification or does not.

In an advantageous embodiment, the present invention relates to a process for the preparation of a mixture of giant p-(R)calixarenes the size of which is greater than 20, in particular from 21 to more than 220, in particular from 21 to 220, in particular from 21 to 212, more particularly from 21 to approximately 200, even more particularly from 21 to approximately 100, comprising a stage of bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I), the water produced during the reaction being retained in said reaction medium during said heating, a solid precursor in the form of an optionally isolated precipitate being obtained, said solid precursor in the form of a precipitate being isolated from the aforesaid reaction medium and not subjected to heat treatment, as defined above, comprising the following stages:
  a. bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I), in particular 4-octyloxyphenol,
    with aqueous formaldehyde, in order to constitute a reaction medium and heating said reaction medium for a period of time comprised from 30 minutes to 2 hours, in particular 1 hour, without removal of the water formed,
    in order to obtain a dimer of formula (II) as defined above,
  b. optionally continuing the heating of said reaction medium containing said dimer while removing the water formed in order to obtain a reaction medium containing a solid precursor, in the form of a precipitate, for 2 to 3 hours,
  c. optionally, after neutralization of the base, washing the reaction medium containing a solid precursor with a polar solvent, in particular methanol, in order to obtain a mixture of giant calixarenes in which R is as defined above, in neutralized form,
  d. optionally the recrystallization of said washed mixture of giant calixarenes, in a solvent based on DMSO, in order to obtain a purified mixture of giant calixarenes in which R is as defined above, and substantially devoid of p-(R)calix[7]arene and/or p-(R)calix[8]arene.
  e. optionally, the purification of said purified mixture of giant calixarenes devoid of p-(R)calix[7]arene and/or p-(R)calix[8]arene using GPC, by separating different fractions depending on their elution time.

In an advantageous embodiment, the present invention relates to a process for the preparation of a mixture of giant p-(R)calixarenes the size of which is greater than 20, in particular from 21 to more than 220, in particular from 21 to 220, in particular from 21 to 212, more particularly from 21 to approximately 200, even more particularly from 21 to approximately 100, comprising a stage of bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I), the water produced during the reaction being retained in said reaction medium during said heating, a solid precursor in the form of an optionally isolated precipitate being obtained, said solid precursor in the form of a precipitate being isolated from the aforesaid reaction medium and not subjected to heat treatment in the presence of an organic solvent, as defined above, comprising the following stages:
  a. bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I), in particular 4-octyloxyphenol,
    with aqueous formaldehyde, in order to constitute a reaction medium and heating said reaction medium for a period of time comprised from 30 minutes to 2 hours, in particular 1 hour, without removal of the water formed,
    in order to obtain a dimer of formula (II) as defined above,
  b. optionally continuing the heating of said reaction medium containing said dimer while removing the water formed in order to obtain a reaction medium containing a solid precursor, in the form of a precipitate, for 2 to 3 hours,
  c. optionally, after neutralization of the base, washing the reaction medium containing a solid precursor with a polar solvent, in particular methanol, in order to obtain a mixture of giant calixarenes in which R is as defined above, in neutralized form,
  d. optionally the recrystallization of said washed mixture of giant calixarenes, from a solvent based on DMSO, in order to obtain a purified mixture of giant calixarenes in which R is as defined above, and substantially devoid of p-(R)calix[7]arene and/or p-(R)calix[8]arene.
  e. optionally, the purification of said purified mixture of giant calixarenes devoid of p-(R)calix[7]arene and/or p-(R)calix[8]arene using GPC, by separating different fractions depending on their elution time.

In stage a, at the end of 10 to 25 minutes, there is the appearance of the oligomers or polymers of formula (III) which then leads, with more prolonged heating, to the dimer of formula (II).

The heating is carried out at a temperature of approximately 100 to 130° C.

Advantageously, the heating is at approximately 110° C., 120° C. or 130° C.

If the dimer is the desired product, it is then recovered by filtration of the reaction medium.

In stage b., the heating is continued at a temperature of approximately 100 to 130° C., if the dimer is not the desired product, this leads to said precursor in the form of a precipitate. Advantageously, the heating is continued for 1 h, 2 h or 3 h and at a temperature comprised from 100° C. to 130° C., advantageously at 110° C., 120° C. or 130° C.

In stage c, the solid precursor in the form of a precipitate, obtained after neutralization with an acid such as HCl or $H_2SO_4$, in particular dilute or non-dilute HCl, is approximately 50 to 90% constituted by giant calixarenes which can also comprise other by-products such as residual linear oligomers or residual dimer, but also p-(R)calix[7]arene and/or p-(R)calix[8]arene.

Washing with a polar solvent makes it possible to purify said precursor and in particular to remove certain residual linear oligomers or residual dimer.

In stage d., the recrystallization from a mixture based on DMSO makes it possible to remove the p-(R)calix[7]arene and/or p-(R)calix[8]arene.

The solvent mixture based on DMSO is in particular a mixture of DMSO with toluene or acetone, DMSO being in a proportion of 5% to 50% by volume in the solvent mixture, in particular 10%.

The DMSO can be replaced by an aprotic polar solvent, preferably DMF.

Stage e. is carried out in order to separate the purified mixture of giant p-(R)calixarenes devoid of p-(R)calix[7]arene and/or of p-(R)calix[8]arene into fractions of giant p-(R)calixarenes of different sizes.

In an advantageous embodiment, the base used in stage a. is $Ba(OH)_2$ and R represents octyloxy. The mixture of giant p-(R)calixarenes obtained contains p-(octyloxy)calix[21-50]

arenes and the size determined by the centred Gaussian using GPC is approximately 33.

In an advantageous embodiment, the present invention relates to a process for the preparation of a mixture of giant p-(R)calixarenes the size of which is greater than 20, in particular from 21 to more than 220, in particular from 21 to 220, in particular from 21 to 212, more particularly from 21 to approximately 200, even more particularly from 21 to approximately 100, comprising a stage of bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I), the water produced during the reaction being retained in said reaction medium during said heating, a solid precursor in the form of an optionally isolated precipitate being obtained, said solid precursor in the form of a precipitate being preceded by the formation of an optionally isolated phenolic dimer, as defined above,
in which said phenolic dimer or said solid precursor in the form of a precipitate, contained in said reaction medium, is placed in the presence of heat transfer means in the form of an oven or of a solvent in which said solid precursor in the form of a precipitate and said phenolic dimer are insoluble, in particular a linear or branched alkane with a boiling point greater than 50° C., in particular greater than 100° C., in particular octane, and is subjected to a heat treatment.

In an advantageous embodiment, the present invention relates to a process for the preparation of a mixture of giant p-(R)calixarenes the size of which is greater than 20, in particular from 21 to more than 220, in particular from 21 to 220, in particular from 21 to 212, more particularly from 21 to approximately 200, even more particularly from 21 to approximately 100, comprising a stage of bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I), the water produced during the reaction being retained in said reaction medium during said heating, a solid precursor in the form of an optionally isolated precipitate being obtained, said solid precursor in the form of a precipitate being preceded by the formation of an optionally isolated phenolic dimer, as defined above,
in which said phenolic dimer or said solid precursor in the form of a precipitate, contained in said reaction medium, is placed in the presence of an organic solvent in which said solid precursor in the form of a precipitate and said phenolic dimer are insoluble, in particular a linear or branched alkane with a boiling point greater than 50° C., in particular greater than 100° C., in particular octane, and is subjected to a heat treatment.

The organic solvent can be any organic solvent provided that, on the one hand, it does not reacted with the precursor in the form of a resin and that, on the other hand, said precursor in the form of a resin is insoluble.

The boiling point of the organic solvent is in particular greater than or equal to 110° C.

The heat treatment is carried out under reflux of said organic solvent, with or without stirring, preferably without stirring of the reaction medium, for a period of time comprised, depending on R and the base, from 3 to 8 h and in particular has the effect, on the one hand, of completing the formation of the macrocycles, in particular those comprised in the solid precursor in the form of a resin, but also of increasing the size of the macrocycles obtained starting equally well from the solid precursor in the form of a resin as from said dimer.

The giant calixarenes obtained comprise however a proportion of calix[7]arene and/or of calix[8]arene which is variable depending on R.

The more insoluble the solid precursor in the form of a resin or a dimer in the organic solvent, the more the proportion of giant calixarenes increases.

The duration of the heat treatment must also be controlled and must be comprised from 3 to 8 h depending on R and the base used.

Above 8 h, the proportion of small calixarenes obtained increases until only small calixarenes are obtained, the giant calixarenes disappearing by dissociating in favour of said small calixarenes.

Depending on the solvent used for the heat treatment, the size of the macrocycles obtained can be modulated.

The lower the temperature of the reaction mixture, the more the size of the macrocycles decreases.

In an advantageous embodiment, the present invention relates to a process for the preparation of a mixture of giant p-(R)calixarenes the size of which is greater than 20 in particular from 21 to more than 220, in particular from 21 to 220, in particular from 21 to 212, more particularly from 21 to approximately 200, even more particularly from 21 to approximately 100, comprising a stage of bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I), the water produced during the reaction being retained in said reaction medium during said heating, a solid precursor in the form of an optionally isolated precipitate being obtained, said solid precursor in the form of a precipitate being preceded by the formation of an optionally isolated phenolic dimer, said phenolic dimer or said solid precursor in the form of a precipitate, contained in said reaction medium, being placed in the presence of heat transfer means in the form of an oven or of a solvent in which said solid precursor in the form of a precipitate and said phenolic dimer are insoluble, in particular a linear or branched alkane with a boiling point greater than 50° C., in particular greater than 100° C., in particular octane and is subjected to a heat treatment, as defined above, comprising the following stages:

a. bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I),
with aqueous formaldehyde, in order to constitute a reaction medium and heating said reaction medium for a period of time comprised from 30 minutes to 1 hour, in particular 1 hour, without removal of the water formed, in order to obtain a dimer of formula (II) as defined above, b. optionally continuing the heating of said reaction medium containing said dimer without removal of the water formed, for 2 to 3 hours, in order to obtain a reaction medium containing a solid precursor in the form of a precipitate, and optionally filtration of said solid precursor in the form of a precipitate, c. heating said reaction medium using heat transfer means in the form of an oven, or the addition to said reaction medium containing said solid precursor in the form of a precipitate of an organic solvent in which said solid precursor in the form of a precipitate is insoluble, in particular a linear or branched alkane with a boiling point greater than 50° C., in particular greater than 100° C., in particular octane, in order to obtain a reaction medium containing a solid in the form of a precipitate in an oven or a solvent and heating said reaction medium containing a solid in the form of a precipitate, for 3 to 8 hours,
  in order to obtain a mixture of giant calixarenes in which R is as defined above, further comprising, a p-(R)calix[7]arene and/or a p-(R)calix[8]arene,
d. recrystallization, after neutralization of the base, from a solvent based on DMSO, in order to obtain a purified mixture of giant calixarenes in which R is as defined above, substantially devoid of p-(R)calix[7]arene and/or a p-(R)calix[8]arene,
e. optionally, the purification of said purified mixture of giant calixarenes devoid of p-(R)calix[7]arene and/or of p-(R)calix[8]arene using GPC, by separating different fractions depending on their elution time.

In an advantageous embodiment, the present invention relates to a process for the preparation of a mixture of giant p-(R)calixarenes the size of which is greater than 20 in particular from 21 to more than 220, in particular from 21 to 220, in particular from 21 to 212, more particularly from 21 to approximately 200, even more particularly from 21 to approximately 100, comprising a stage of bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I), the water produced during the reaction being retained in said reaction medium during said heating, a solid precursor in the form of an optionally isolated precipitate being obtained, said solid precursor in the form of a precipitate being preceded by the formation of an optionally isolated phenolic dimer, said phenolic dimer or said solid precursor in the form of a precipitate, contained in said reaction medium, being placed in the presence of an organic solvent in which said solid precursor in the form of a precipitate and said phenolic dimer are insoluble, in particular a linear or branched alkane with a boiling point greater than 50° C., in particular greater than 100° C., in particular octane and is subjected to a heat treatment, as defined above, comprising the following stages:
  a. bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I),
    with aqueous formaldehyde, in order to constitute a reaction medium and heating said reaction medium for a period of time comprised from 30 minutes to 1 hour, in particular 1 hour, without removal of the water formed, in order to obtain a dimer of formula (II) as defined above,
  b. optionally continuing the heating of said reaction medium containing said dimer without removal of the water formed, for 2 to 3 hours, in order to obtain a reaction medium containing a solid precursor in the form of a precipitate, and optionally filtration of said solid precursor in the form of a precipitate,
  c. the addition to said reaction medium containing said solid precursor in the form of a precipitate of an organic solvent in which said solid precursor in the form of a precipitate is insoluble, in particular a linear or branched alkane with a boiling point greater than 50° C., in particular greater than 100° C., in particular octane, in order to obtain a reaction medium containing a solid in the form of a precipitate in a solvent and heating said reaction medium containing a solid in the form of a precipitate, for 3 to 8 hours,
    in order to obtain a mixture of giant calixarenes in which R is as defined above, further comprising a p-(R)calix[7]arene and/or a p-(R)calix[8]arene,
  d. recrystallization, after neutralization of the base, from a solvent based on DMSO, in order to obtain a purified mixture of giant calixarenes in which R is as defined above, substantially devoid of p-(R)calix[7]arene and/or a p-(R)calix[8]arene,
  optionally, the purification of said purified mixture of giant calixarenes devoid of p-(R)calix[7]arene and/or of p-(R)calix[8]arene using GPC, by separating different fractions depending on their elution time,
  and the size determined by the centred Gaussian using GPC is approximately 21 to 50.

In stage a., at the end of 10 to 25 minutes, there is the appearance of the oligomers or polymers of formula (III) which then leads, with more prolonged heating, to the dimer of formula (II).

The heating is carried out at a temperature of approximately 100 to 130° C. for 30 minutes to 2 h starting from an initial reaction medium in order to form the dimer of formula (II).

Advantageously, the heating is at approximately 110° C., 120° C. or 130° C.

If the dimer is the desired product, it is then recovered by filtration of the reaction medium.

In stage b., the heating is continued at a temperature of approximately 100 to 130° C., if the dimer is not the desired product, which leads to said precursor in the form of a hard brittle resin. Advantageously, the heating is continued for 1 h, 2 h or 3 h and at a temperature comprised from 100° C. to 130° C., advantageously at 110° C., 120° C. or 130° C.

The mixture obtained in stage b. consists of approximately 50% of giant p-(R)calixarenes and can be isolated by simple filtration.

In stage c, either the solvent is introduced directly into the reaction medium of the preceding stage b., or said solid precursor in the form of a hard brittle resin is introduced into an apparatus for carrying out a reaction and the organic solvent in which said solid precursor in the form of a hard brittle resin is insoluble is introduced, thus constituting the reaction medium.

The heat treatment is carried out under reflux of said organic solvent, with or without stirring, preferably without stirring of the reaction medium.

The heat treatment makes it possible to complete the formation of the macrocycles and to increase the size of the giant p-(R)calixarenes.

Advantageously, the heat treatment is comprised from approximately 3 to 4 h.

Advantageously, when the heat treatment is comprised from 3 to 4 h, the base used is LiOH, KOH, NaOH, CsOH or RbOH.

Advantageously, the heat treatment is comprised from approximately 6 to 8 h, in particular 7 h.

Advantageously, when the heat treatment is comprised from approximately 6 to 8 h, in particular 7 h, the base used is $Ba(OH)_2$.

In stage d., the solvent mixture based on DMSO is in particular a mixture of DMSO with toluene or acetone, DMSO being in a proportion of 5% to 50% by volume in the solvent mixture, in particular 10%.

The DMSO can be replaced by an aprotic polar solvent, preferably DMF.

Stage e. is carried out in order to separate the purified mixture of giant p-(R)calixarenes devoid of p-(R)calix[7]arene and/or of p-(R)calix[8]arene into fractions of giant p-(R)calixarenes of different sizes.

In an advantageous embodiment, the base used in stage a. is Ba(OH)$_2$, LiOH, KOH or RbOH and R represents benzyloxy.

The mixture of giant p-(R)calixarenes obtained is p-(benzyloxy)calix[21-50]arenes and the size is determined by the centred Gaussian using GPC is approximately 30.

In an advantageous embodiment, the present invention relates to a process for the preparation of a mixture of giant p-(R)calixarenes the size of which is greater than 20, in particular from 21 to more than 220, in particular from 21 to 220, in particular from 21 to 212, more particularly from 21 to approximately 200, even more particularly from 21 to approximately 100, comprising a stage of bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I), the water produced during the reaction being retained in said reaction medium during said heating, a solid precursor in the form of an optionally isolated precipitate being obtained, said solid precursor in the form of a precipitate being preceded by the formation of an optionally isolated phenolic dimer, as defined above, in which said phenolic dimer or said solid precursor in the form of a precipitate, contained in said reaction medium, is placed in the presence of an organic solvent in which said solid precursor in the form of a precipitate and said phenolic dimer are at least partially soluble, in particular in xylene, toluene, DMSO or DMF, and is subjected to a heat treatment.

When the solid precursor in the form of a precipitate or the dimer are dissolved for the heat treatment stage, the macrocycles obtained are of greater purity with respect to the process consisting of no dissolution of the solid precursor in the form of a precipitate or of the dimer in the organic solvent, however, the proportion of small calixarenes present and in particular of calix[7]arene and/or of calix[8]arene is greater.

The heat treatment is carried out under reflux of said organic solvent, with or without stirring, preferably without stirring of the reaction medium.

The duration of the heat treatment must also be controlled and must be comprised from 3 to 8 h depending on R and the base used, the concentration of the base, and the temperature.

Above 8 h, the proportion of small calixarenes obtained increases until only small calixarenes are obtained, the giant calixarenes disappearing by dissociating in favour of said small calixarenes.

Depending on the solvent used for the heat treatment with dissolution, the size of the macrocycles obtained can be modulated.

The more temperature is low the more the size of the macrocycles obtained decreases.

The mixture of giant p-(R)calixarenes obtained consists of p-(benzyloxy)calix[n]arenes and the size determined using GPC (centred Gaussian) is approximately 22 repeat units.

In an advantageous embodiment, the present invention relates to a process for the preparation of a mixture of giant p-(R)calixarenes the size of which is greater than 20, in particular from 21 to more than 220, in particular from 21 to 220, in particular from 21 to 212, more particularly from 21 to approximately 200, even more particularly from 21 to approximately 100, comprising a stage of bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I), the water produced during the reaction being retained in said reaction medium during said heating, a solid precursor in the form of an optionally isolated precipitate being obtained, said solid precursor in the form of a precipitate being preceded by the formation of an optionally isolated phenolic dimer, said phenolic dimer or said solid precursor in the form of a precipitate, contained in said reaction medium, being placed in the presence of an organic solvent in which said solid precursor in the form of a precipitate and said phenolic dimer are at least partially soluble, in particular in xylene, toluene, DMSO or DMF, and being subjected to a heat treatment, as defined above, comprising the following stages:

a. bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I),
   with aqueous formaldehyde, in order to constitute a reaction medium and heating said reaction medium for a period of time comprised from 30 minutes to 2 hours, in particular 1 hour, without removal of the water formed,
   in order to obtain a dimer of formula (II) as defined above, b. optionally continuing the heating of said reaction medium containing said dimer without removal of the water formed, for 2 to 3 hours, in order to obtain a reaction medium containing a solid precursor in the form of a precipitate, and optionally filtration of said solid precursor in the form of a precipitate, c. the addition to said reaction medium containing said solid precursor in the form of a precipitate of an organic solvent in which said solid precursor in the form of a precipitate is at least partially soluble, in particular xylene, toluene, DMSO or DMF, in order to obtain a reaction medium containing a solid in the form of a precipitate in suspension in an organic solvent, and heating said reaction medium containing a solid in the form of a dissolved precipitate, for 3 to 8 hours,
   in order to obtain a mixture of giant calixarenes in which R is as defined above, further comprising, a p-(R)calix[7]arene and/or a p-(R)calix[8]arene, d. the recrystallization of said mixture of giant calixarenes, after neutralization of the base, from a solvent based on DMSO, in order to obtain a purified mixture of giant calixarenes in which R is as defined above, substantially devoid of p-(R)calix[7]arene and/or a p-(R)calix[8]arene, e. optionally purification using GPC, by separating different fractions depending on their elution time.

In stage a., at the end of 10 to 25 minutes, there is the appearance of the oligomers or polymers of formula (III) which then leads, with more prolonged heating, to the dimer of formula (II).

The heating is carried out at a temperature of approximately 100 to 130° C. for 30 minutes to 2 hours starting from the initial reaction medium in order to form the dimer of formula (II)

Advantageously, the heating is at approximately 110° C., 120° C. or 130° C.

If the dimer is the desired product, it is then recovered by filtration of the reaction medium.

In stage b., the heating is continued at a temperature of approximately 100 to 130° C., if the dimer is not the desired product, which leads to said precursor in the form of a hard brittle resin. Advantageously, the heating is continued for 1 h, 2 h or 3 h and at a temperature comprised from 100° C. to 130° C., advantageously at 110° C., 120° C. or 130° C.

The mixture obtained in stage b. is constituted by approximately 50 to 90% of giant p-(R)calixarenes and can be isolated by simple filtration.

In stage c., the heat treatment makes it possible to complete the formation of the macrocycles and to increase the size of the giant p-(R)calixarenes.

The heat treatment is carried out under reflux of said organic solvent, with or without stirring, preferably without stirring of the reaction medium.

Advantageously, the heat treatment is comprised from approximately 3 to 4 h.

Advantageously, when the heat treatment is comprised from 3 to 4 h, the base used is LiOH, KOH, NaOH, CsOH or RbOH.

Advantageously, the heat treatment is comprised from approximately 6 to 8 h, in particular 7 h.

Advantageously, when the heat treatment is comprised from approximately 6 to 8 h, in particular 7 h, the base used is $Ba(OH)_2$.

In stage d., the solvent mixture based on DMSO is in particular a mixture of DMSO with toluene or acetone, DMSO being in a proportion of 5% to 50% by volume in the solvent mixture, in particular 10%.

The DMSO can be replaced by an aprotic polar solvent, preferably DMF.

Stage e. is carried out in order to separate the purified mixture of giant p-(R)calixarenes devoid of p-(R)calix[7]arene and/or of p-(R)calix[8]arene into fractions of giant p-(R)calixarenes of different sizes.

In an advantageous embodiment, the base used in stage a. is $Ba(OH)_2$, LiOH, KOH, NaOH, CsOH or RbOH and R represents benzyloxy.

The mixture of giant p-(R)calixarenes obtained is p-(benzyloxy)calix[21-30]arenes and the size determined by the centred Gaussian using GPC is approximately 22.

In an advantageous embodiment, the present invention relates to a process for the preparation of a mixture of giant p-(R)calixarenes the size of which is greater than 20, in particular from 21 to more than 220, in particular from 21 to 220, in particular from 21 to 212, more particularly from 21 to approximately 200, even more particularly from 21 to approximately 100, comprising a stage of bringing at least one base, in particular selected from barium hydroxide, rubidium hydroxide, lithium hydroxide, caesium hydroxide, potassium hydroxide or sodium hydroxide, into contact with at least one phenol substituted in position 4 of formula (I), the water produced during the reaction being retained in said reaction medium during said heating, a solid precursor in the form of an optionally isolated precipitate being obtained, as defined above, in which said phenolic dimer is isolated then subjected to a heat treatment as described above, and to a recrystallization as defined in stages c. and d. above.

When the dimer is isolated in the neutral form, a base, in particular the base having been used in order to obtain said dimer, more particularly at a concentration used in order to obtain said dimer, is added prior to the heat treatment.

When the dimer is isolated in the form of a salt, the addition of a base is not necessary.

Said isolated dimer is then placed in the presence of an organic solvent, in particular an organic solvent in which said phenolic dimer is soluble or insoluble, as defined above, and is subjected to the heat treatment as above.

In an advantageous embodiment, the present invention relates to a process for the preparation of a mixture of giant p-(R)calixarenes, the water produced during the reaction being retained in said reaction medium during said heating, as defined above, in which said solid precursor in the form of a precipitate, preceded by the formation of a phenolic dimer, is isolated and placed in the presence of an organic solvent in which said solid precursor in the form of a precipitate is insoluble, then subjected to a heat treatment and to a recrystallization as defined in stages c. and d. above.

When the solid precursor is isolated in the neutral form, a base, in particular the base having been used in order to obtain said dimer, more particularly at a concentration used in order to obtain said dimer, is added prior to the heat treatment.

When the precursor is isolated in the form of a salt, the addition of a base is not necessary.

Said solid precursor in the form of an isolated precipitate is then placed in the presence of an organic solvent, in particular an organic solvent in which said solid precursor in the form of an isolated precipitate is soluble or insoluble, as defined above, and is subjected to the heat treatment as above.

It should be noted that the dimer of general formula (II) or the solid precursors in the form of a precipitate or of a hard brittle resin of general formula (III) can also be prepared by processes other than those of the invention and well known to a person skilled in the art and be used for the preparation of a mixture of giant p-(R)calixarenes according to the invention.

According to another aspect, the present invention relates to the use of a mixture of giant p-(R)calixarenes the size of which is greater than 20, in particular from 21 to more than 220, in particular from 21 to 220, in particular from 21 to 212, more particularly from 21 to approximately 200, even more particularly from 21 to approximately 100, R being as defined above, for the constitution of a material or in the context of reinforcement of materials.

The calixarenes of the invention can also be used for trapping particles, the "template" synthesis of nanoparticles, nanofiltration, gas filtration, the complexing of ions, the encapsulation of molecules and the administration of medicinal products ("drug delivery") owing to the presence of the large cavity present inside the giant calixarenes.

The large cavity present inside the giant calixarenes also makes it possible to envisage the formation of porous cross-linked materials having applications in gels or foams.

They can also serve as a perforation agent of the lipid layer because of the possibility offered, of concentrating certain types of functions by grafting onto the macrocyclic crown and their cyclic configuration.

The grafting of hydrophilic agents onto the available hydroxyls can lead to the formation of micelles, taking into account the marked amphiphilic character of the units obtained in this way and the structure of the giant calixarenes.

The amphiphilic giant calixarenes containing in particular cationic counter-ions of significant size can be used for vectorization i.e. for inserting active ingredients into a cell.

It is also possible to graft one or more types of polymerization initiators onto each crown of the calixarenes, selectively, in order to constitute polymers with a complex architecture allowing an increase in their amphiphilic character, to improve the encapsulation of active ingredient and their dispersion in a physiological medium, to generate novel properties at the level of related materials, for example.

In an advantageous embodiment, the present invention relates to the use of a mixture of giant p-(R)calixarenes the size of which is greater than 20, in particular from 21 to more than 220, in particular from 21 to 220, in particular from 21 to 212, more particularly from 21 to approximately 200, R being as defined above, for the constitution of a material or in the context of reinforcement of materials, in which said mixture further comprises, a p-(R)calix[7]arene and/or a p-(R)calix[8]arene.

According to another aspect, the present invention relates to the use of a mixture of calixarenes as defined above, capable of being obtained by one of the processes defined above, for the constitution of a material or in the context of reinforcement of materials.

In an advantageous embodiment, the present invention relates to the use of a mixture of calixarenes as defined above, capable of being obtained by one of the processes defined above, for the constitution of a material or in the context of reinforcement of materials, in which said mixture further comprises, a p-(R)calix[7]arene and/or a p-(R)calix[8]arene.

Y-axis: ln(D) where D represents the self diffusion coefficient of the molecules which depends among other things on their hydrodynamic volume determined by diffusional NMR PGSE (Pulse Gradient Spin Echo) diffusion NMR.

This curve makes it possible to link the self diffusion coefficient to the average molar mass of a mixture of calixarenes.

Figure 1:
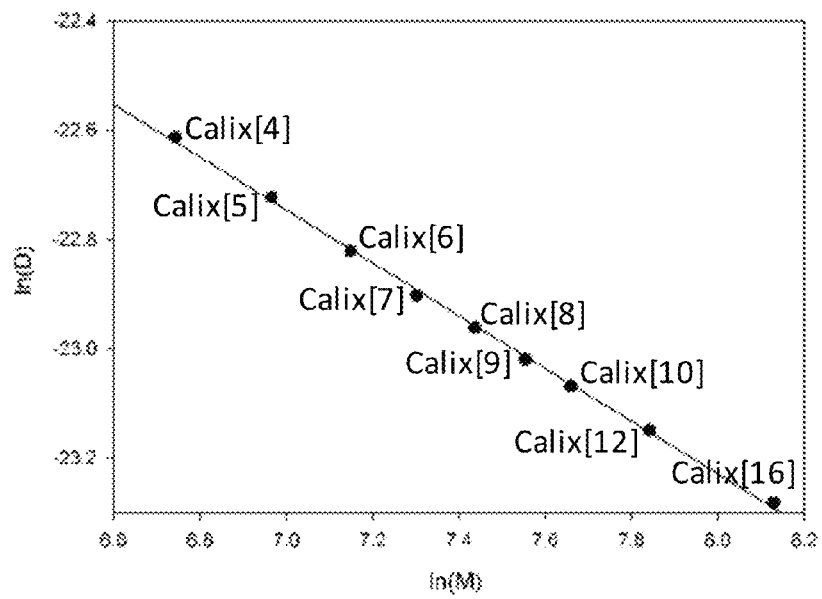
FIG. 1 shows the calibration curve obtained with the pure samples of p-(benzyloxy)calix[4-16]arenes using diffusional NMR synthesized according to Example 5. It makes it possible to validate the molar mass of the pure p-(benzyloxy)calix[4-16]arenes determined by size exclusion chromatography. X-axis: ln(M) where M represents the molecular weight of the p-(benzyloxy)calix[4-16]arenes.
Figure 2:
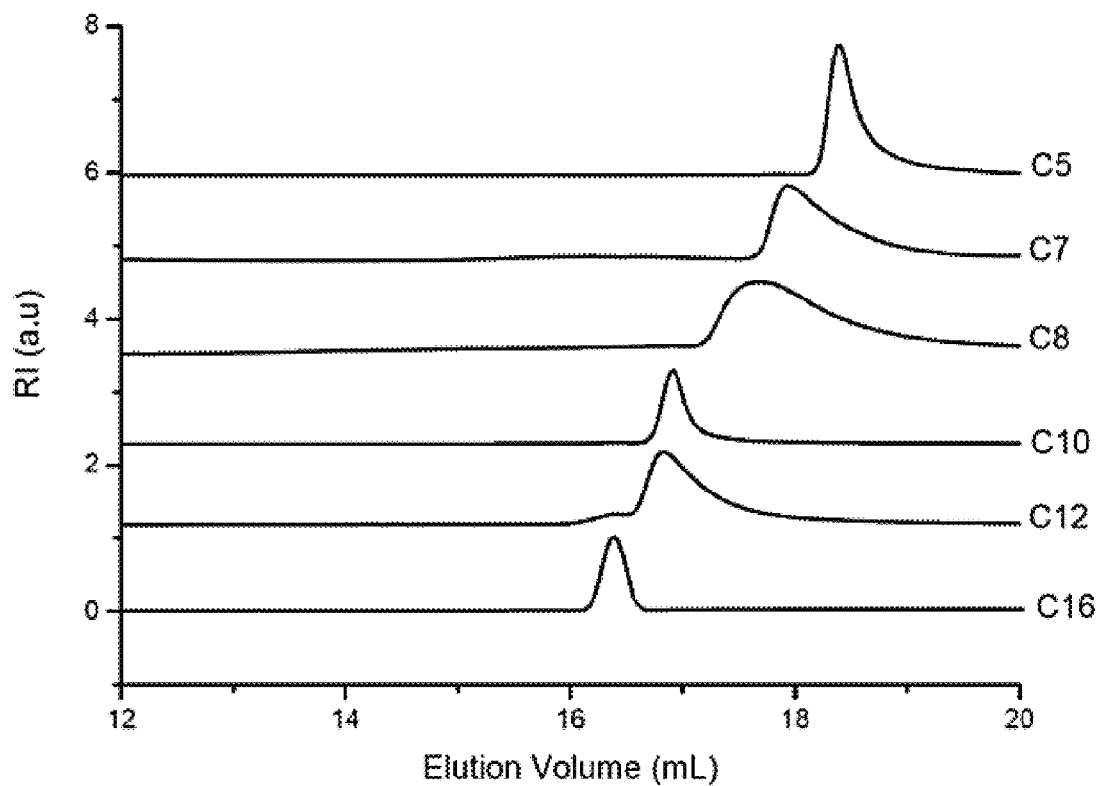

FIG. 2 shows the size exclusion chromatography of the pure reference samples of p-(benzyloxy)calix[6]arene, p-(benzyloxy)calix[7]arene, p-(benzyloxy)calix[8]arene, p-(benzyloxy)calix[10]arene, p-(benzyloxy)calix[12]arene and p-(benzyloxy)calix[16]arene, This technique makes it possible to separate the molecules depending on their hydrodynamic volume and to estimate the molar mass of pure or mixed samples starting from a range of pure standards. The molar masses representative of a pure calixarene or of a mixture of calixarenes are expressed by "peak molar masses" (Mp) and "average molar masses", giving information respectively on the majority population and on the average of the populations.
On the x-axis: Elution volume: Ve(ml)
On the y-axis: RI SIGNAL, corresponding to the refractive index of samples or standards in solution leaving the chromatography column.

Figure 3:
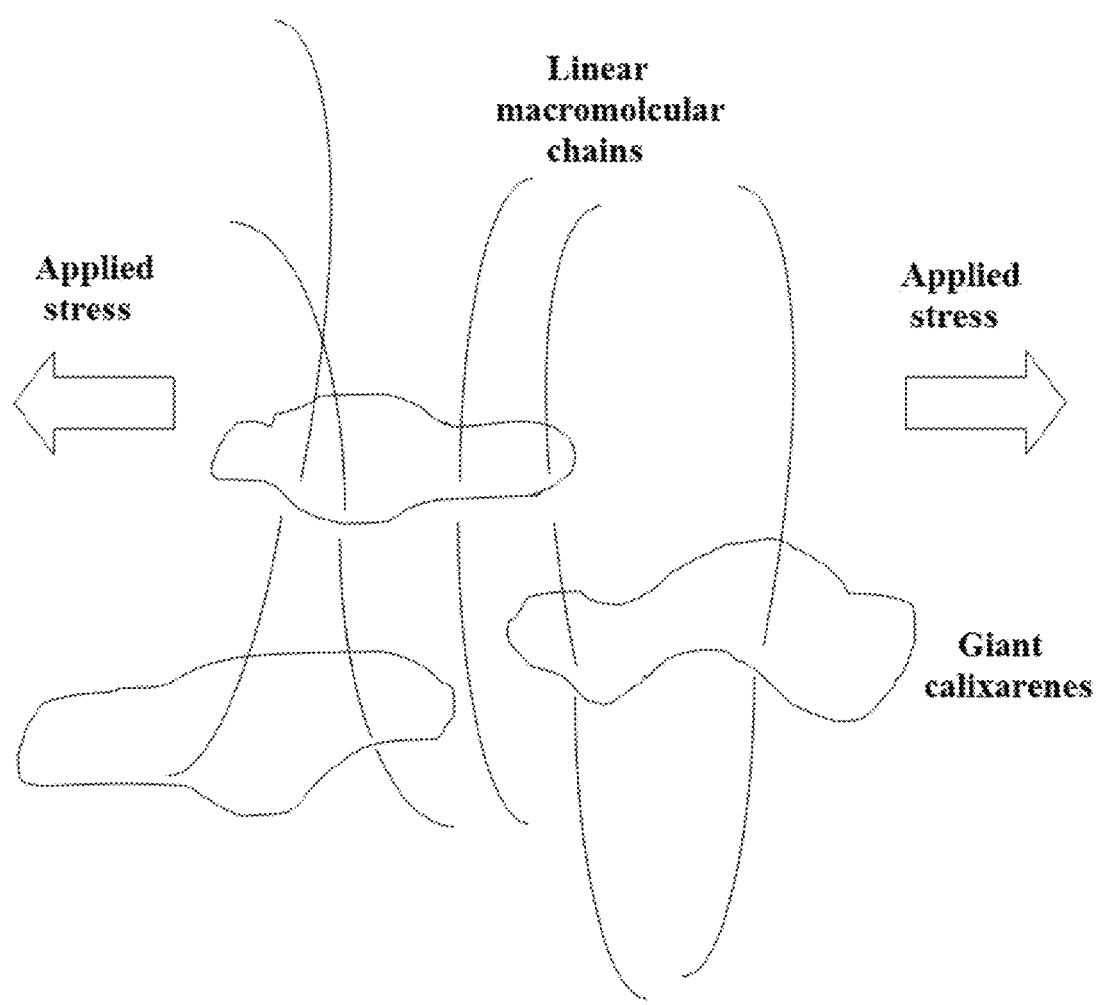

FIG. 3 shows the use of the giant calixarenes as reinforcement of materials by the insertion of polymers into the cavity thereof, which allows better distribution of stress inside, as well as slowing the propagation of cracks (fracture initiation).

Figure 4:
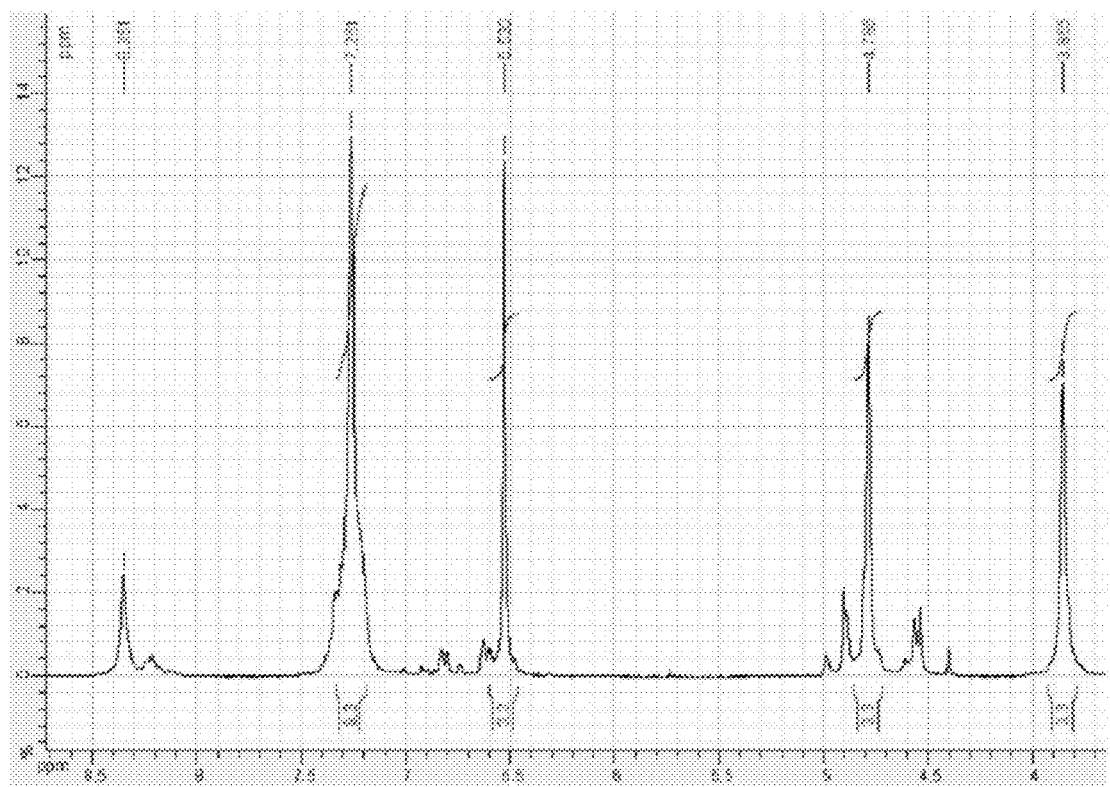

FIG. 4 shows an NMR analysis of the microcrystalline solid obtained at the end of the recrystallization presented in Example 1a).

Figure 5A:
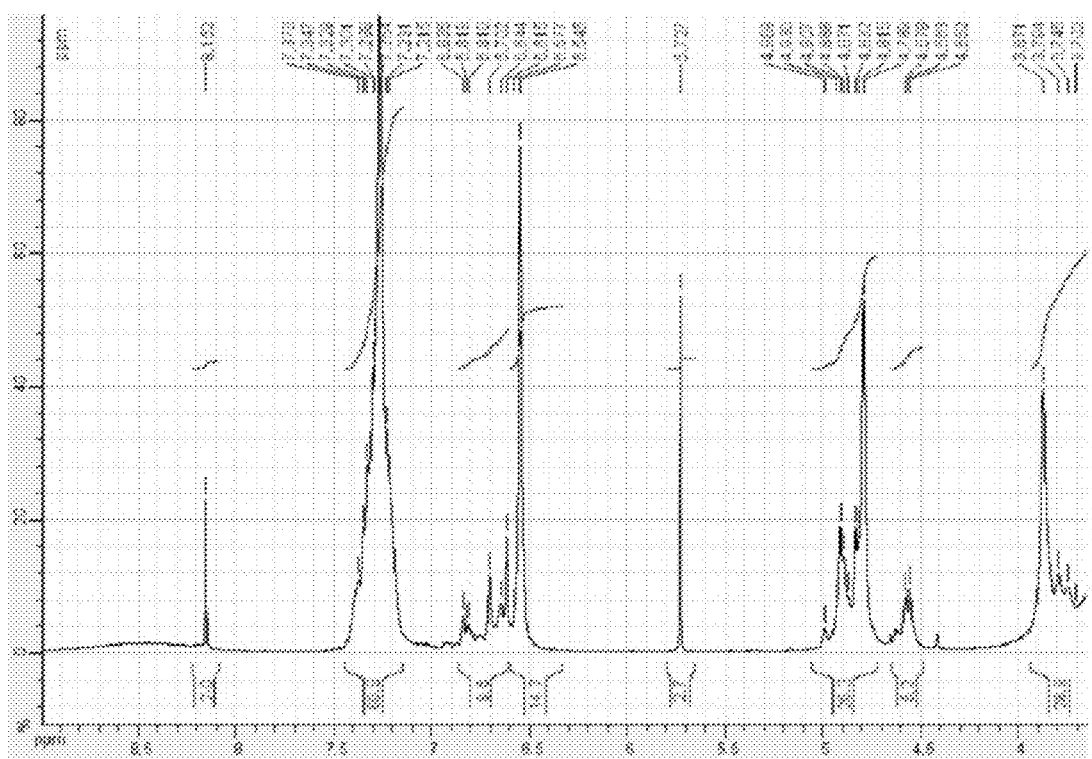

FIG. 5a shows an NMR analysis of the solid obtained after the reflux process without stirring presented in Example 1b).

Figure 5B:
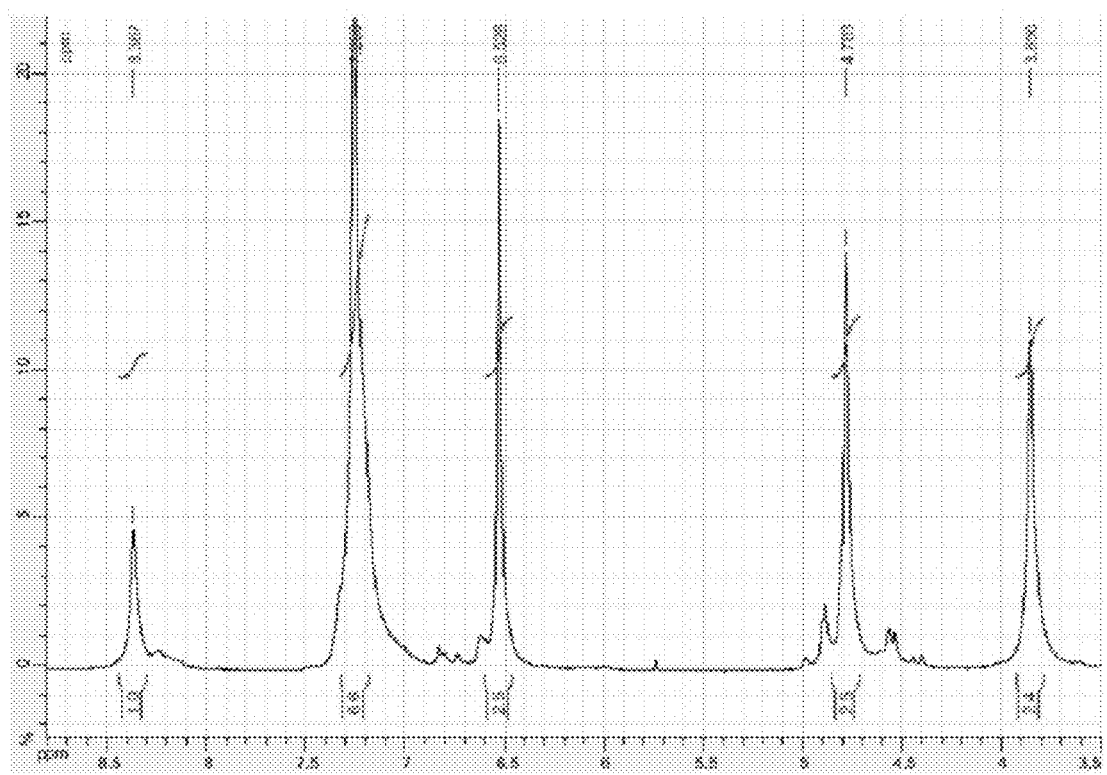

FIG. 5b shows an NMR analysis of the solid obtained after the recrystallization presented in Example 1b).

Figure 6:
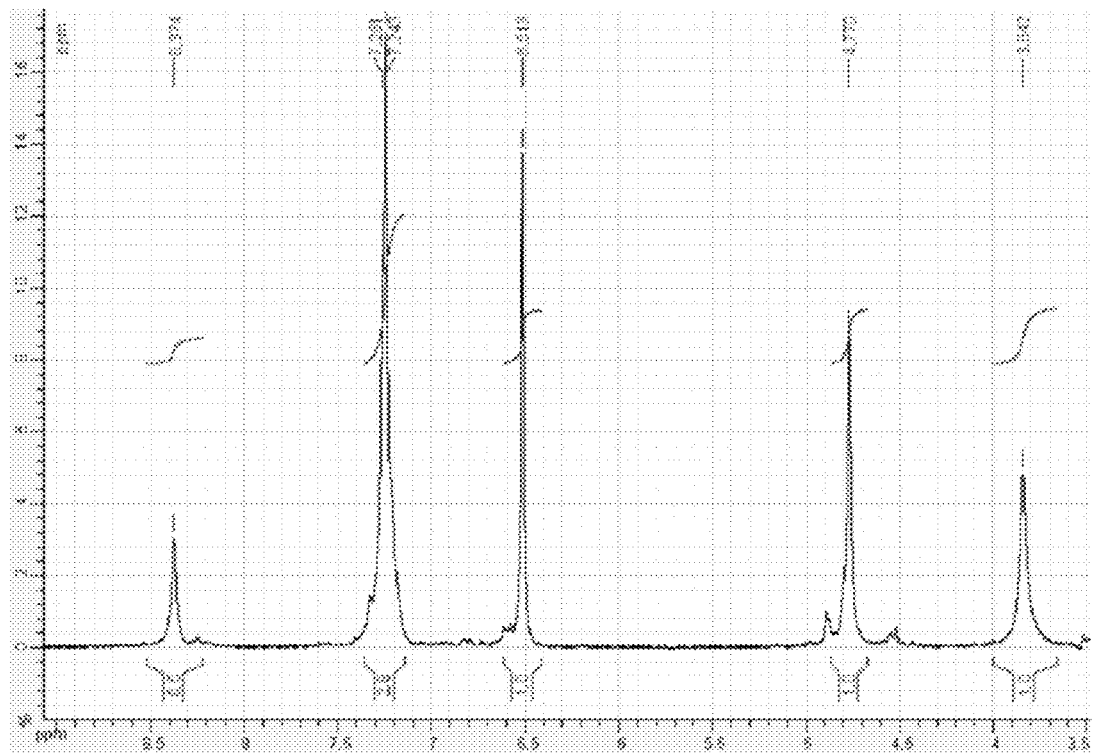

FIG. 6 shows an NMR analysis of the microcrystalline solid obtained at the end of the recrystallization presented in Example 1 d)A.

Figure 7:
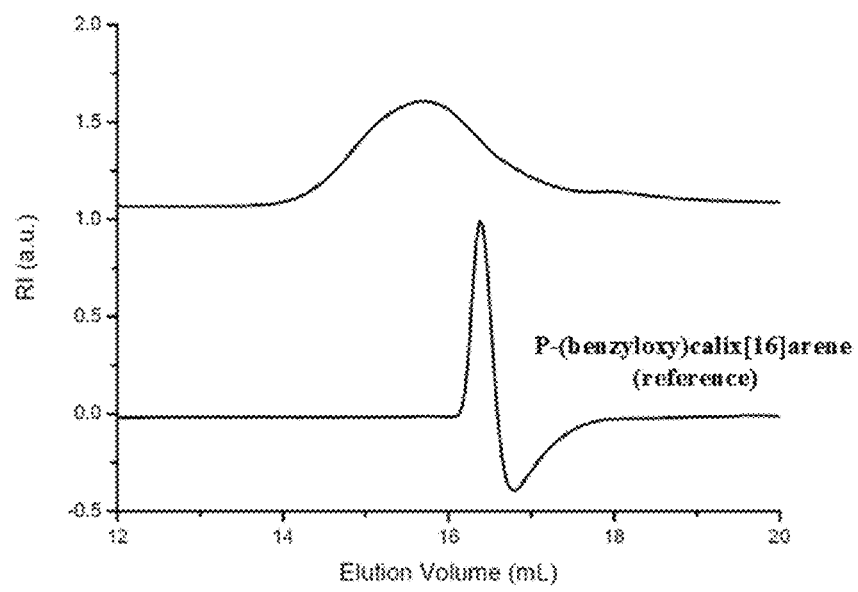

FIG. 7 shows a measurement of the molar mass using gel permeation chromatography (GPC) of the microcrystalline solid obtained at the end of the recrystallization presented in Example 1d)A.

Figure 8:
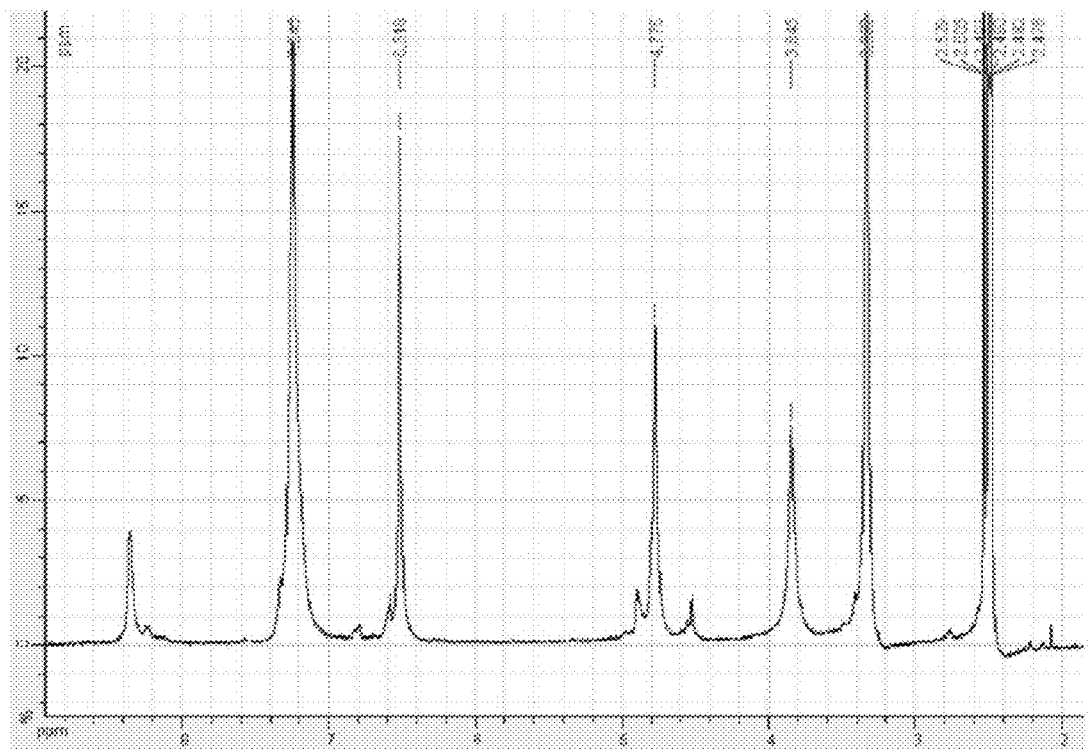

FIG. 8 shows an NMR analysis of the microcrystalline precipitate obtained at the end of the recrystallization presented in Example 1d)B.

Figure 9:
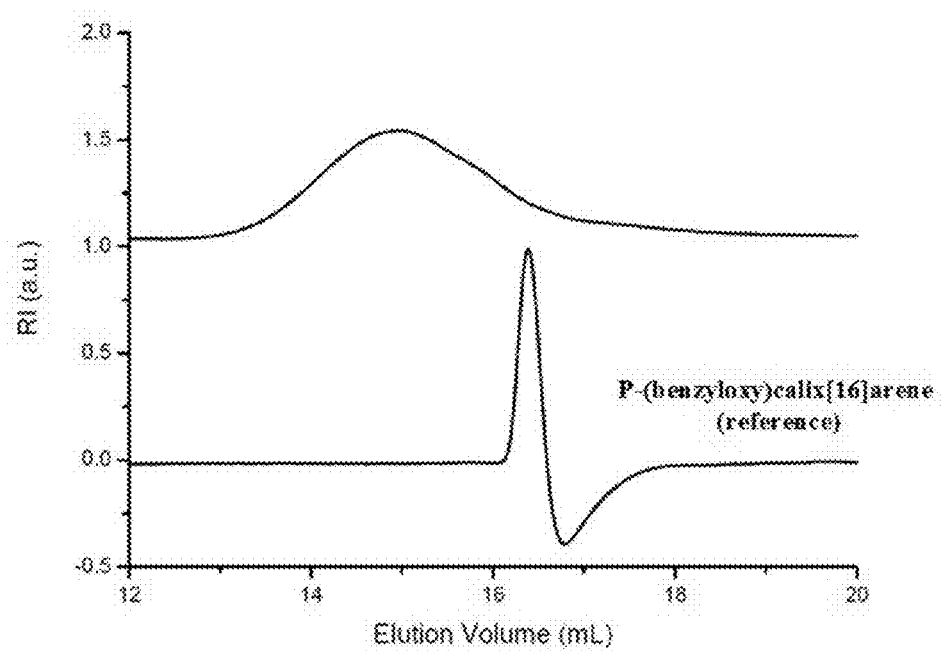

FIG. 9 shows a measurement of the molar mass using GPC of the microcrystalline precipitate obtained at the end of the recrystallization presented in Example 1 d)B.

Figure 10A:
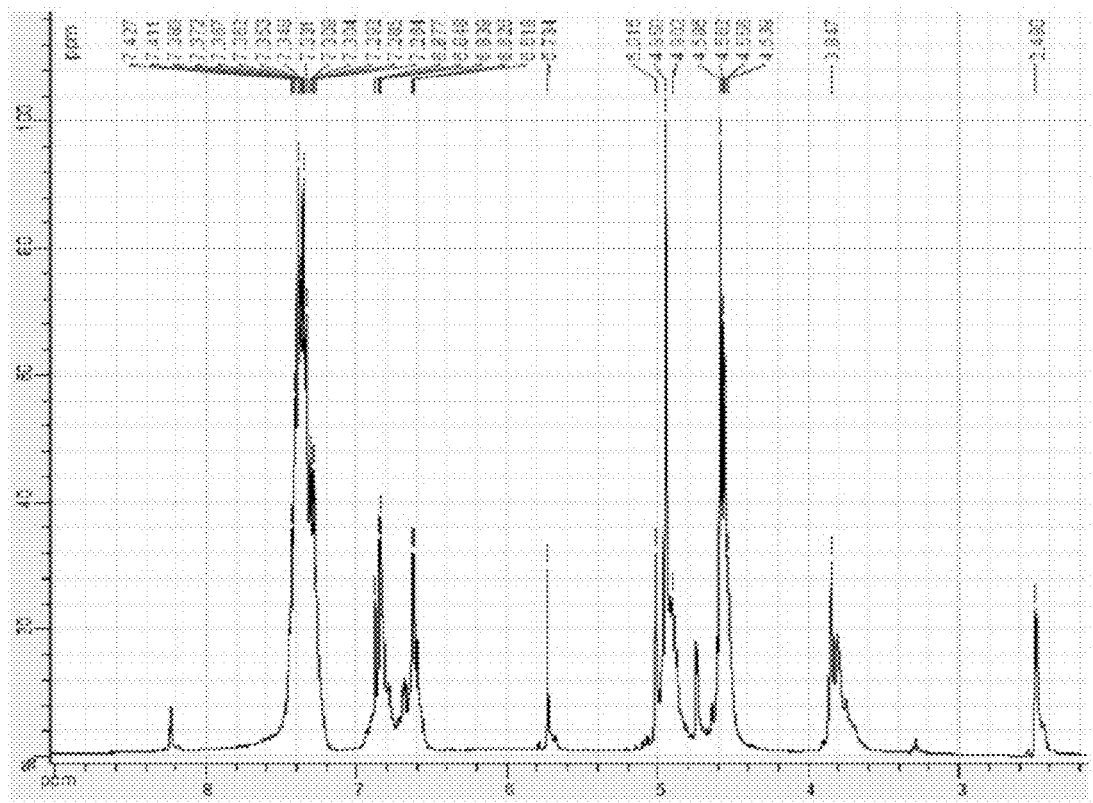

FIG. 10a shows an NMR analysis of the solid mainly constituted by the dimer, obtained as reaction intermediate in Example 1d)C.

Figure 10B:
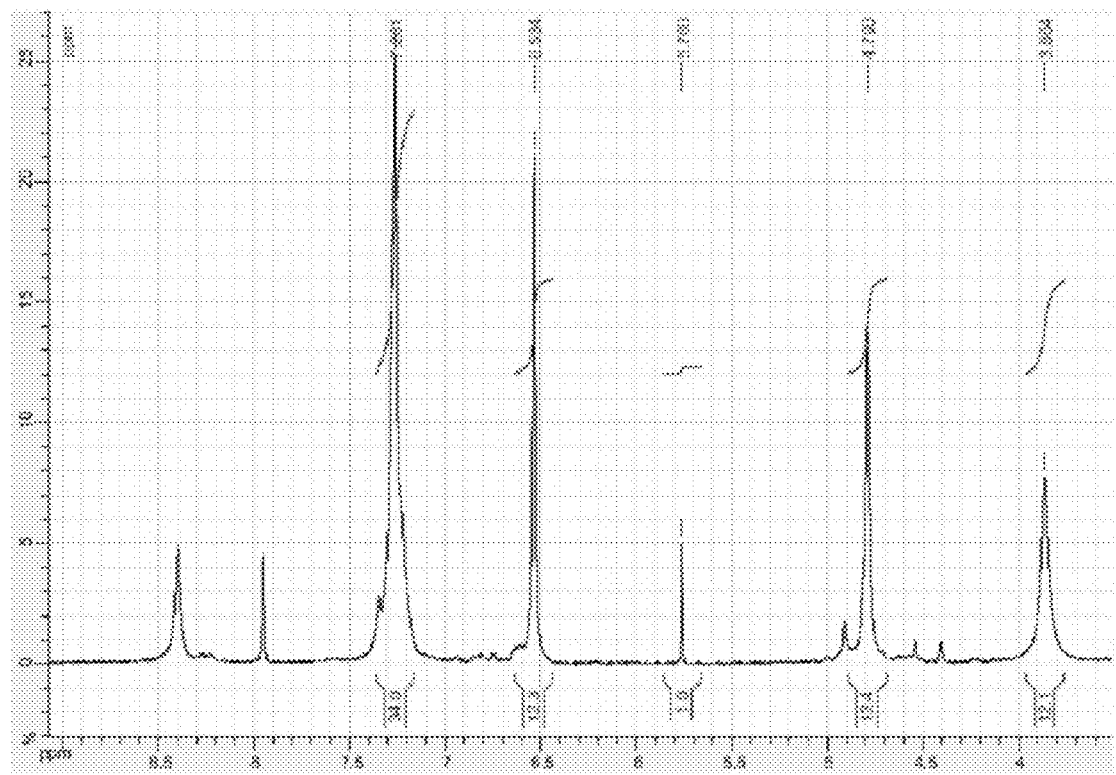

FIG. 10b shows an NMR analysis of the solid obtained after reflux, in Example 1d)C.

Figure 10C:
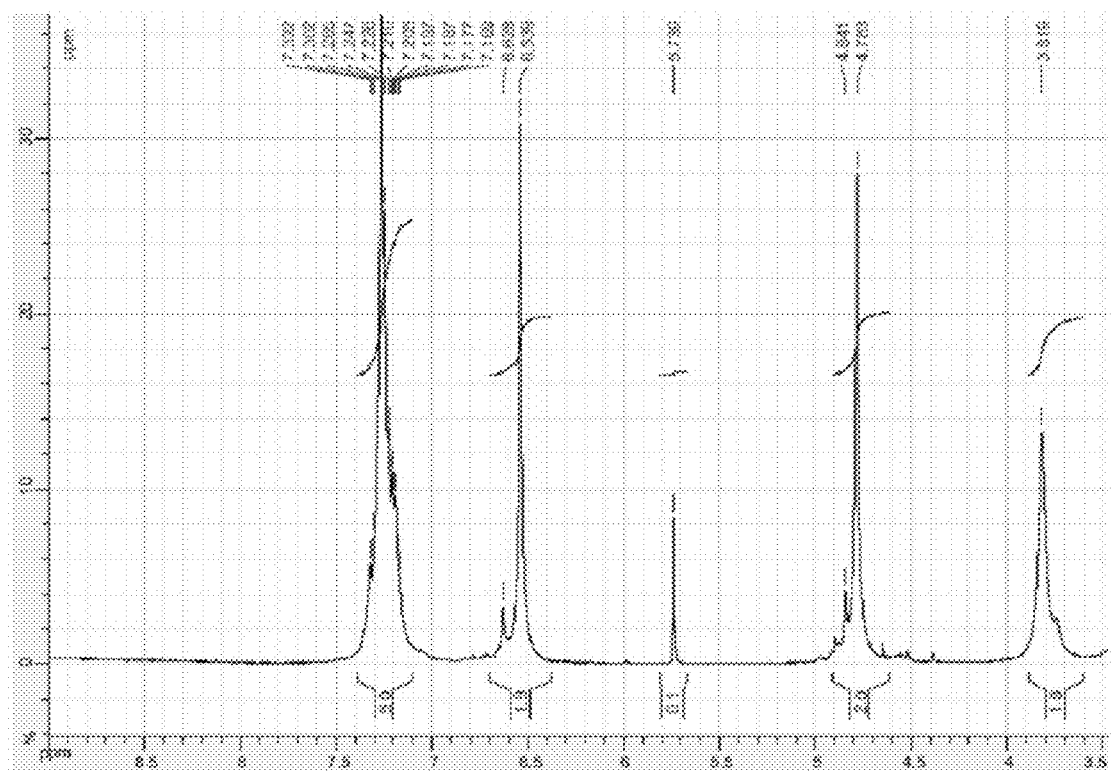

FIG. 10c shows a $^1$H NMR analysis of calix[80]arene described in Example 1d)C-2.

Figure 11:
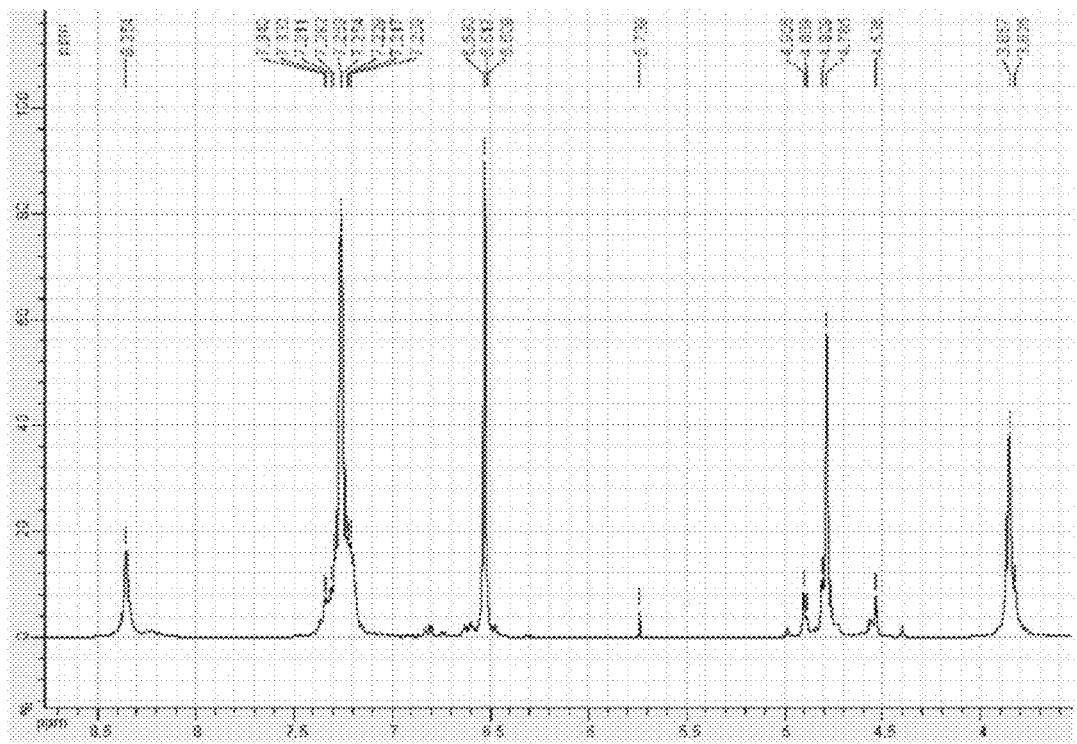

FIG. 11 shows an NMR analysis of the microcrystalline solid obtained at the end of the recrystallization presented in Example 1e)A.

Figure 12:
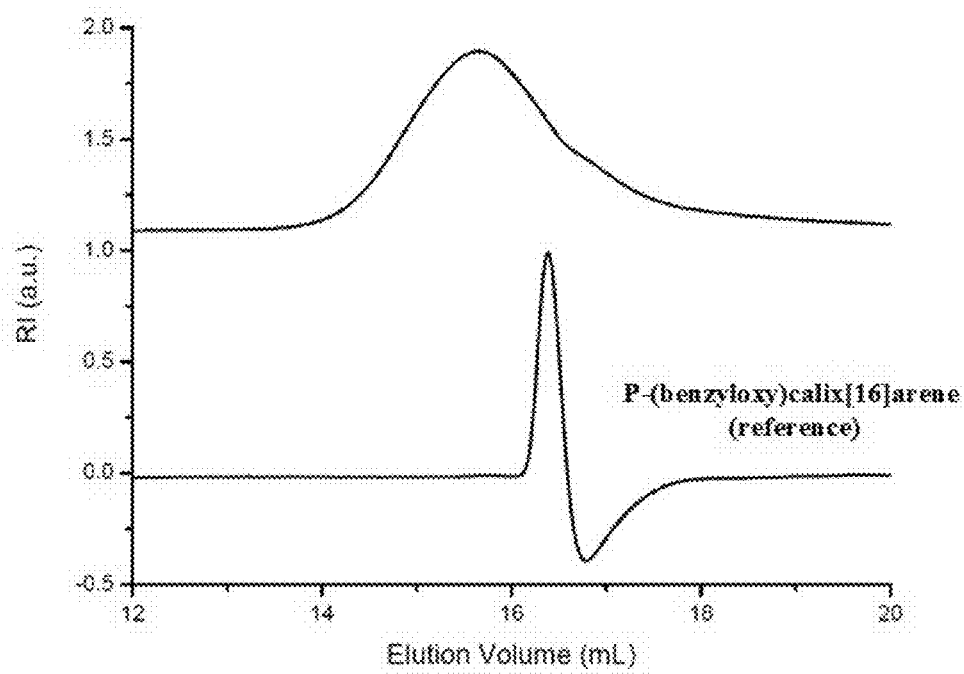

FIG. 12 shows a measurement of the molar mass using GPC of the microcrystalline solid obtained at the end of the recrystallization presented in Example 1e)A.

Figure 13:
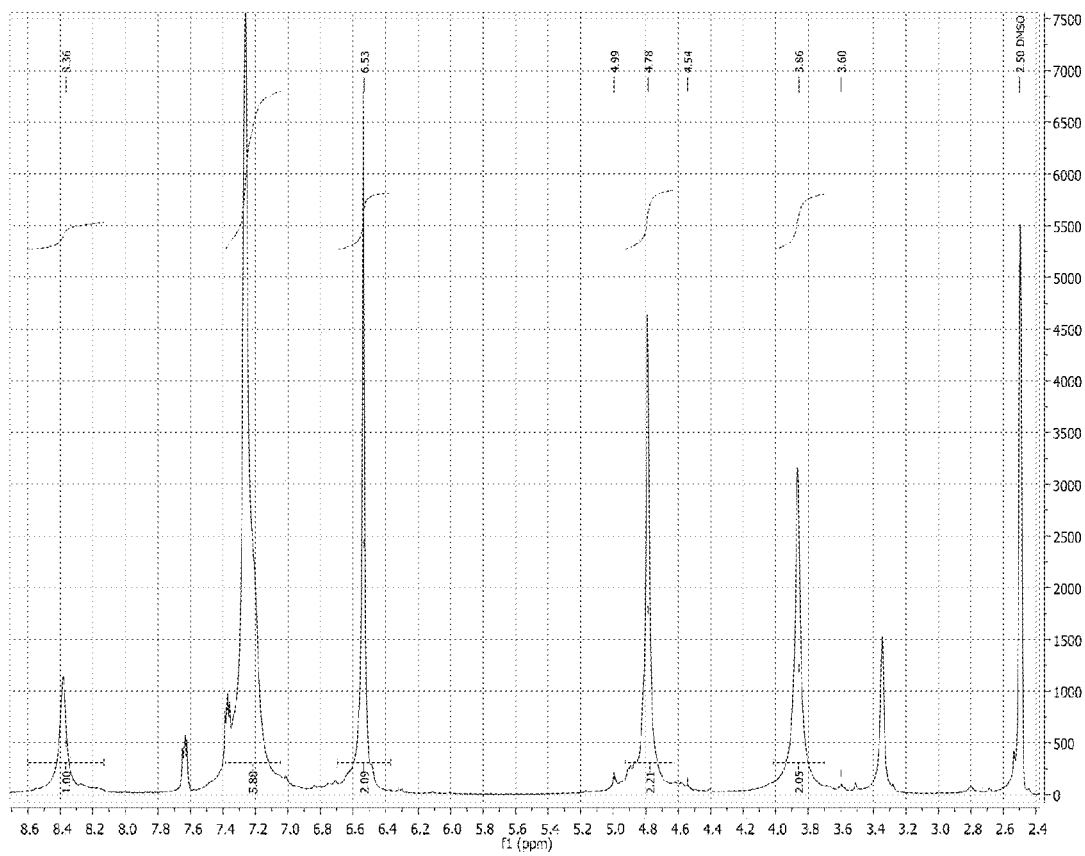

FIG. 13 shows an NMR analysis of the solid obtained at the end of the recrystallization presented in Example 1e)B.

Figure 14:
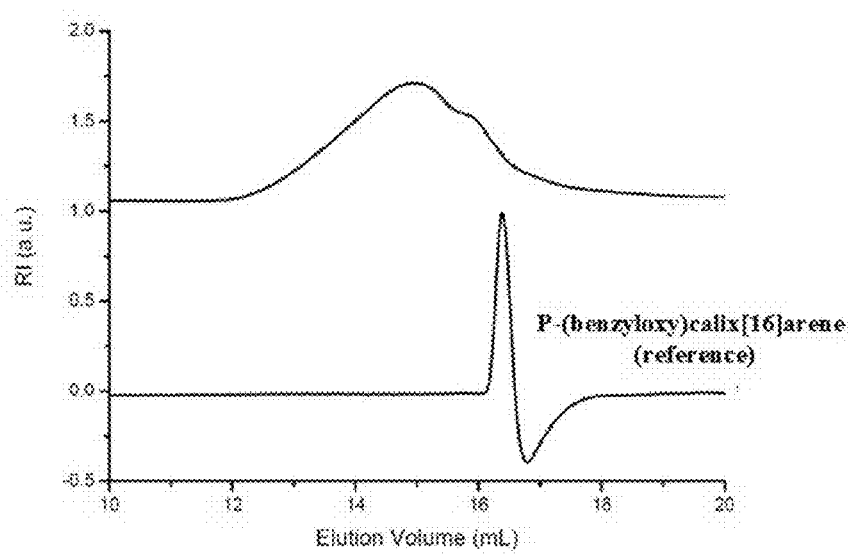

FIG. 14 shows a measurement of the molar mass using GPC of the solid obtained at the end of the recrystallization presented in Example 1e)B.

Figure 15:
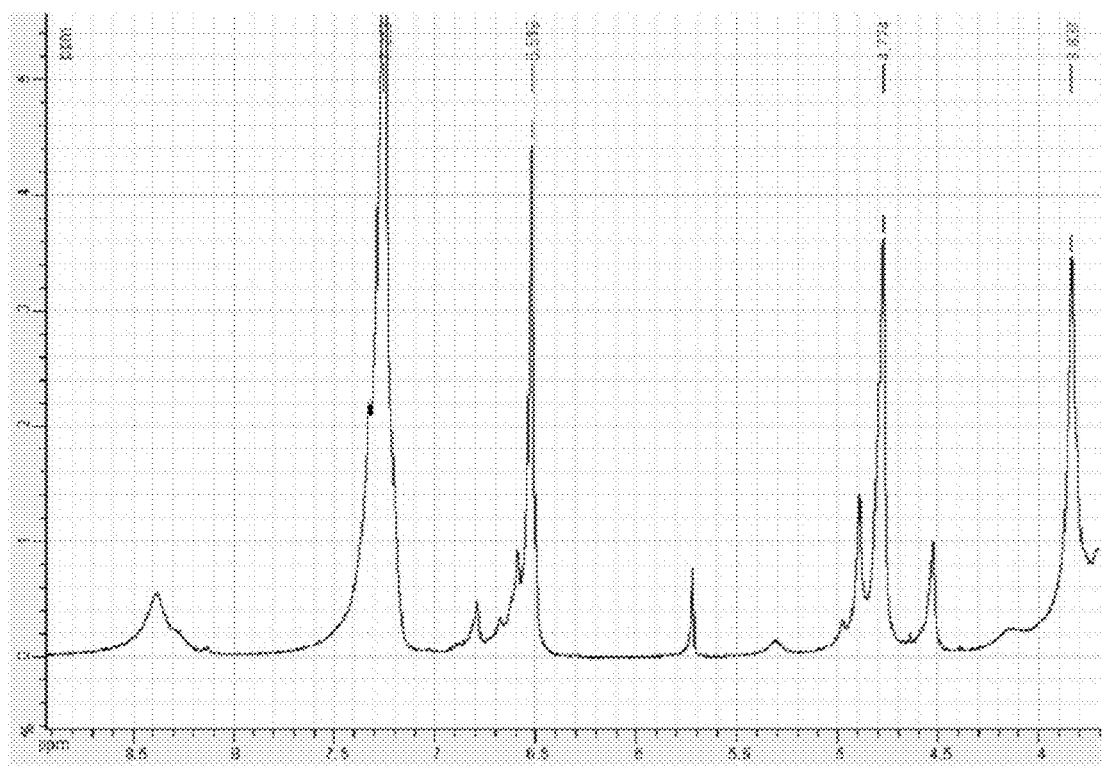

FIG. 15 shows an NMR analysis of the white solid obtained at the end of the reaction presented in Example 1 g).

Figure 16:
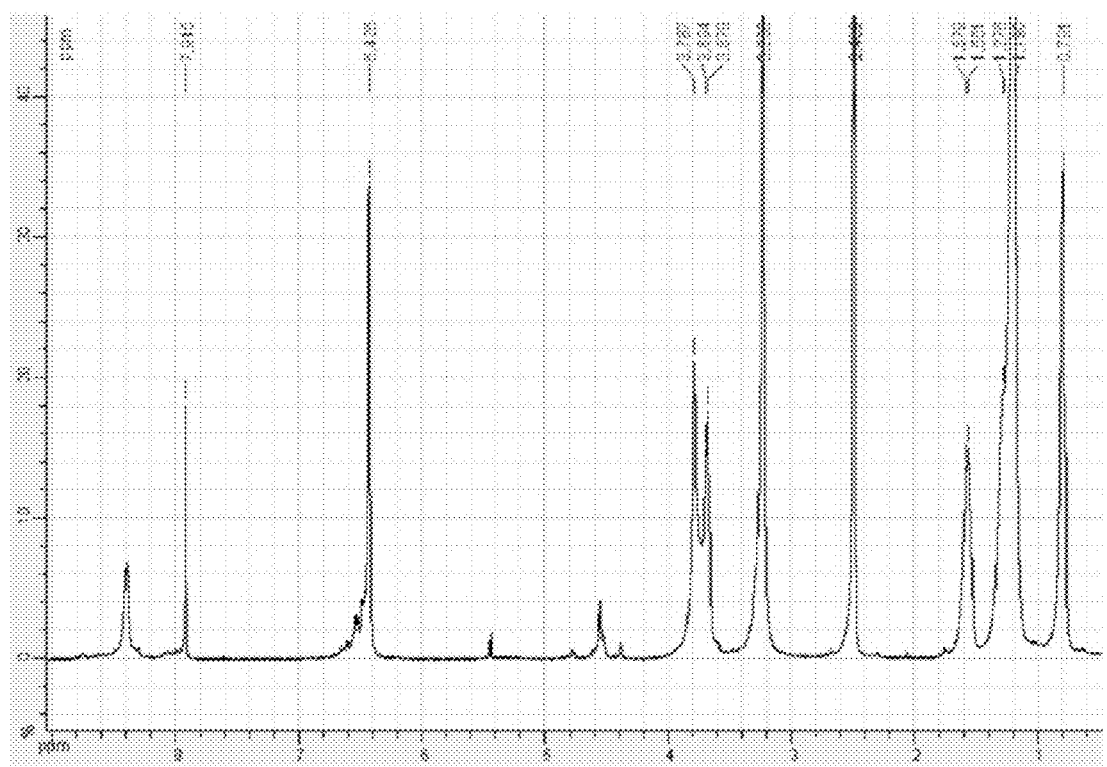

FIG. 16 shows an NMR analysis of the white solid obtained at the end of the reaction presented in Example 2a).

Figure 17:
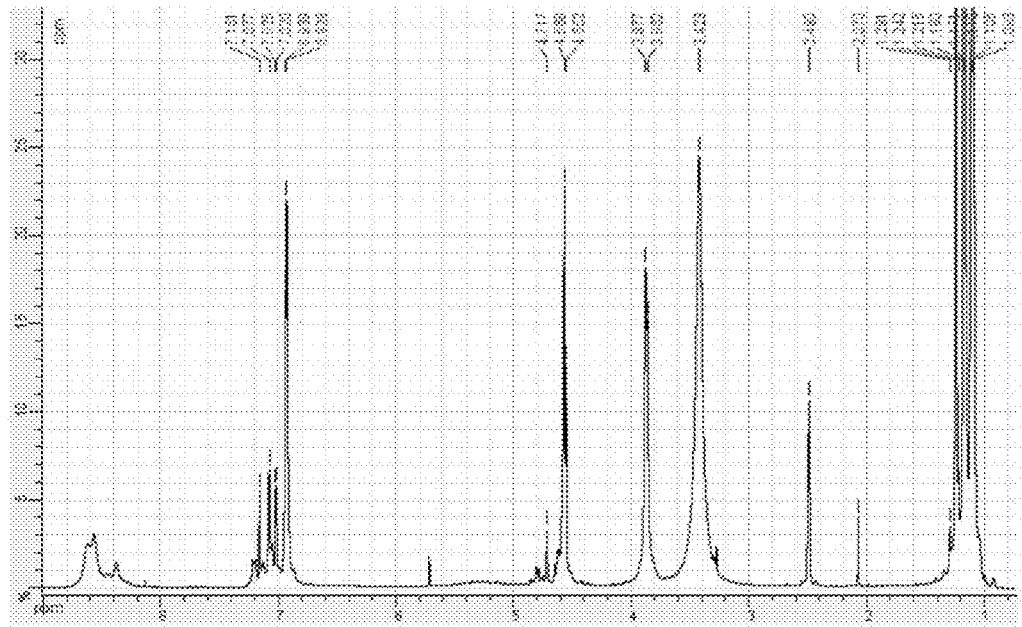
Figure 17:
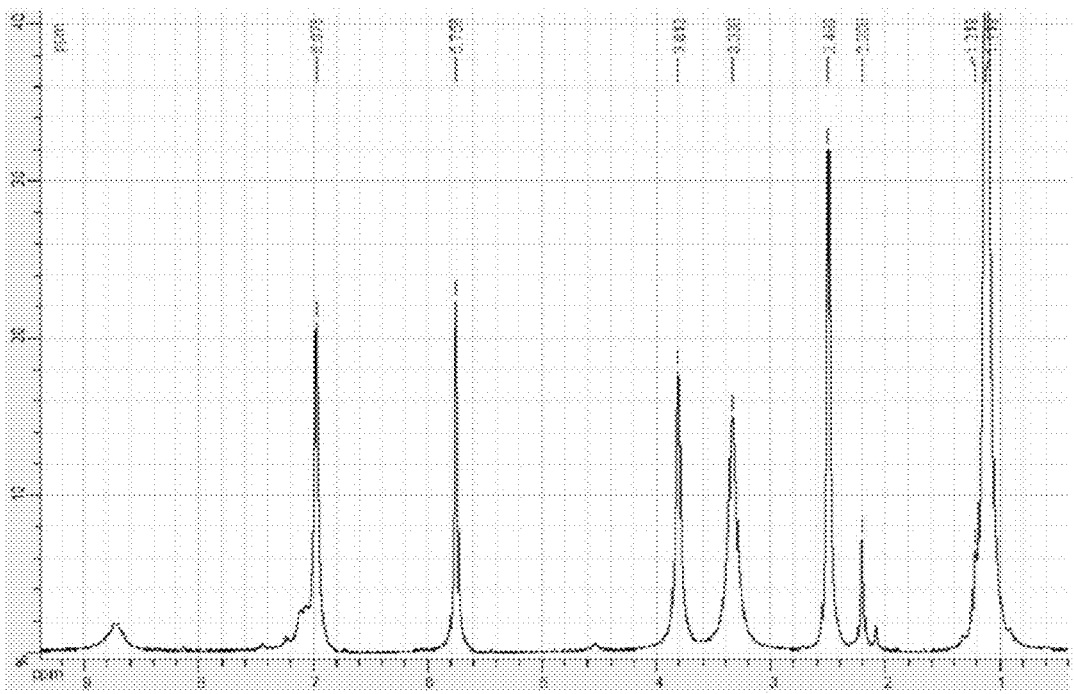

FIG. 17 shows an NMR analysis of the solid obtained, before the addition of toluene, in Example 4 (FIG. 17.1) as well as the reference NMR spectrum of p-(tBu)calix[8]arene (FIG. 17.2).

Figure 18:
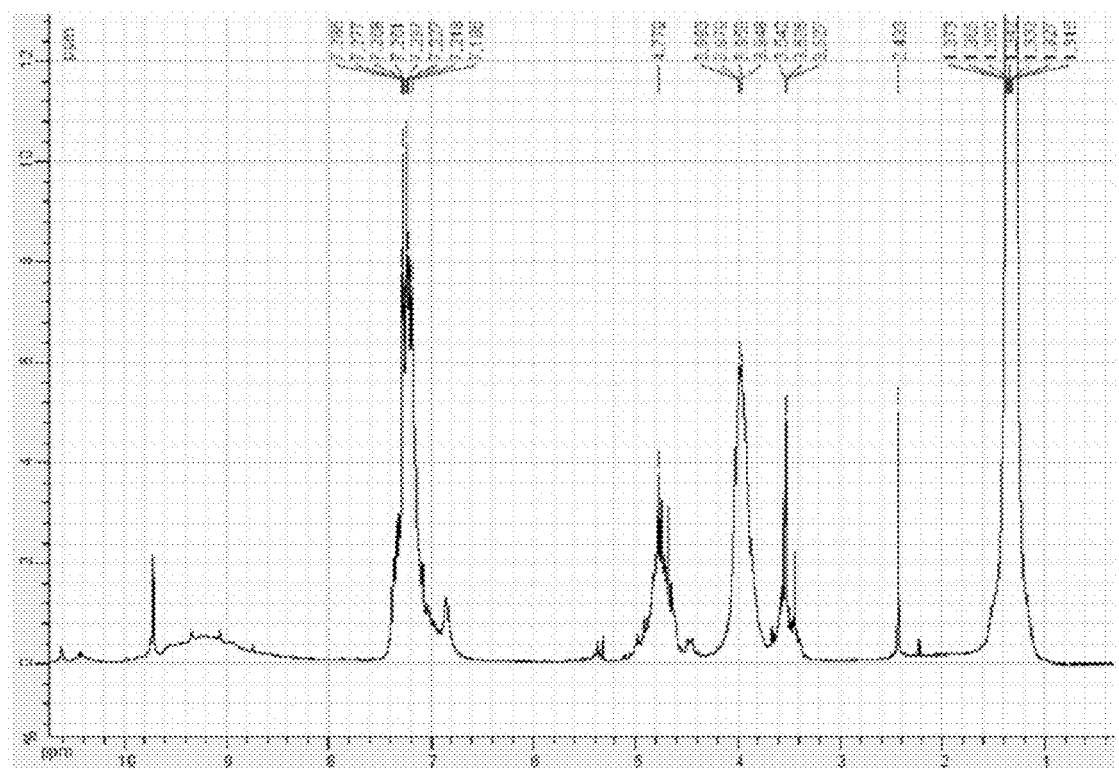

FIG. 18 shows an NMR analysis of the solid obtained after reflux and neutralization, in Example 4.

Figure 19:
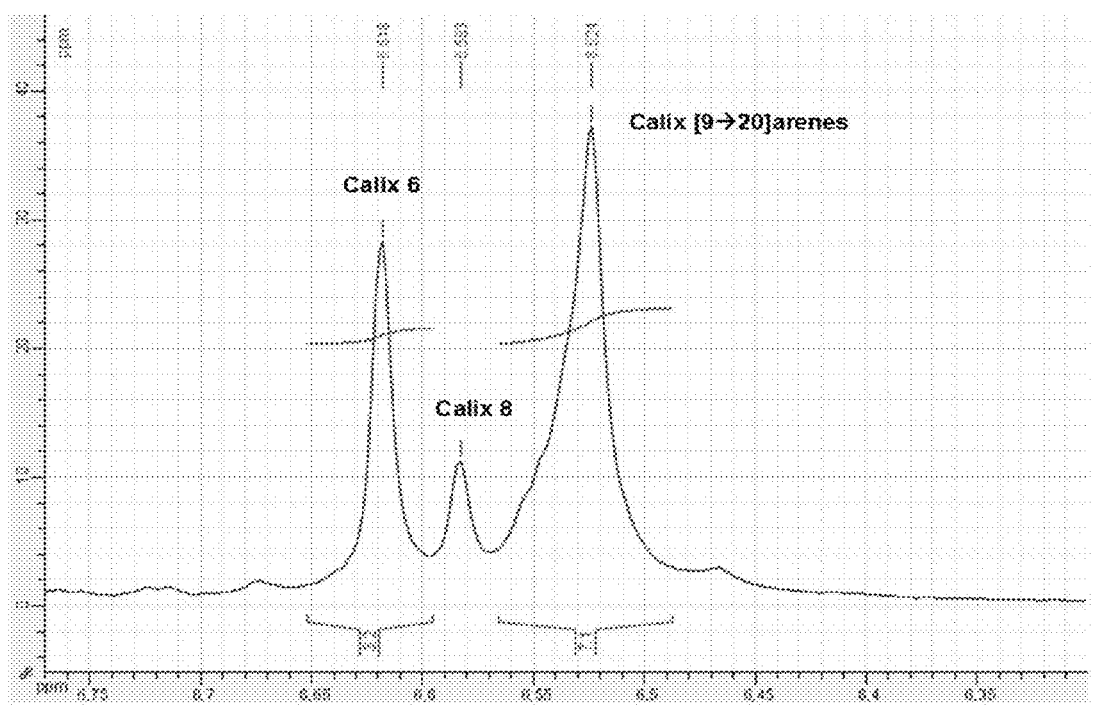

FIG. 19 shows an NMR analysis of the clear orange-coloured solution obtained in Example 5.

Figure 20:
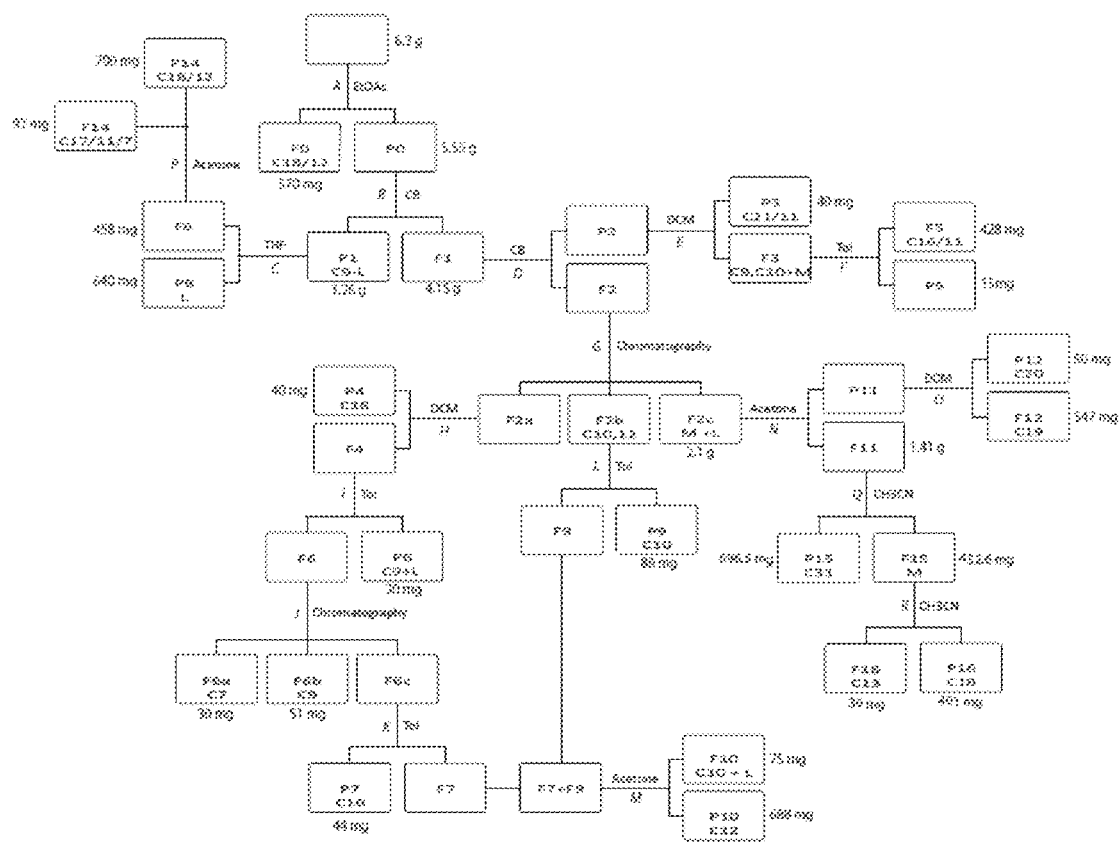

FIG. 20 shows a diagram of the purification of a mixture of large calixarenes obtained in Example 5, after a stage of crystallization from the acetone-DMSO mixture (10% by volume of DMSO). The abbreviations PX and FX correspond respectively to the precipitate of the fraction X and the filtrate of the fraction X. The fractions in bold correspond to isolated pure calixarenes.

Each letter in italics corresponds to a purification stage, carried out in chronological order under the following conditions:

A: the crude product containing the mixture of calixarenes is stirred in ethyl acetate then filtered in order to obtain the fractions P0 and F0.

B: the precipitate P0 is heated under reflux for 1 h under argon and with stirring in 450 mL of chlorobenzene then filtered in order to obtain the fractions P1 and F1.

C: the precipitate P1 is placed under vigorous stirring in 40 mL of THF overnight, filtered and copiously rinsed with THF in order to obtain the fractions P8 (640 mg, Mp corresponds to 20 units) and F8.

D: F1 is heated under reflux under argon and with stirring in 75 mL of chlorobenzene then cooled down and stirred for 1 h at ambient temperature. The solution is placed overnight at −20° C. and filtered in order to obtain the fractions P2 and F2.

E: P2 is placed under stirring in 20 mL of dichloromethane at ambient temperature overnight in order to obtain the fractions F3 and P3 (40 mg, mixture of calixarenes the Mps of which correspond to 22, 11 and 8 units).

F: F3 is dissolved in 40 mL of toluene under reflux then cooled down to ambient temperature. After stirring for 4 h at ambient temperature, the suspension is filtered in order to obtain F5 (428 mg, a mixture of calixarenes the Mps of which correspond to 11 and 17 units) and P5 (15 mg).

G: F2 is dissolved hot in toluene and deposited on a silica column. The calixarene mixture is firstly eluted with dichloromethane in order to obtain the fractions F2a and F2b, then with tetrahydrofuran in order to obtain the fraction Fc.

H: 15 mL of DCM is added to the fraction F2a and a white precipitate immediately appears. After leaving to rest for 1 h without stirring, the suspension is filtered in order to obtain P4 (40 mg, pure calix[16]arene) and F4.

I: F4 is heated briefly under reflux of toluene (20 mL) until totally dissolved then placed at ambient temperature for 24 h without stirring. A suspension is obtained which is filtered in order to obtain the fractions F6 and P6 (30 mg, mixture of large calixarenes).

J: F6 is dissolved in toluene then deposited on a silica column. Chromatography is carried out with an eluent gradient 70/30 to 100/0 of dichloromethane/toluene. The following are isolated, in order of elution: calix[7]arene (30 mg), calix[9]arene and a mixture of calix[10+12]arenes (fraction F6c).

K: F6c is heated briefly under reflux of toluene (6 mL) until totally dissolved then placed at ambient temperature for 48 h without stirring. A suspension is obtained that is diluted in 20 mL of toluene. The suspension is filtered in order to obtain P7 (44 mg, pure calix[10]arene) and F7.

L: F2b is dissolved in 10 mL of toluene. A white precipitate rapidly appears and the suspension is stored for 5 days without stirring. 25 mL of toluene is added and, after 2 weeks without stirring, the suspension is filtered in order to obtain P9 (88 mg, pure calix[10]arene) and F9.

M: F7 and F9 are collected, dispersed in 150 mL of acetone then heated for 1 h under reflux of the solvent. The suspension is filtered in order to obtain P10 (688 mg, pure calix[12]arene) and F5 (75 mg, mixture of calix[10]arene and other large calixarenes).

N: F2c is placed under stirring in acetone at ambient temperature for 24 h then filtered in order to obtain a precipitate. This precipitate is subjected to three cycles of washings/filtrations in acetone. P11 (512 mg) and, after assembly of the filtrates, F11 (1.43 g) are obtained.

O: P11 is placed under stirring in 25 mL of dichloromethane at ambient temperature over a weekend. P12 (50 mg, mixture of calixarenes the Mp of which corresponds to 21 units) and F12 (547 mg, two populations the Mps of which correspond to 19 and 30 units) are obtained.

P: F8 and P13 are assembled and placed with stirring in acetone for 24 h in order to obtain P14 (790 mg, two populations the Mps of which correspond to 19 and 12 units) and F14 (92 mg, two populations the Mps of which correspond to 17 and 11 units).

Q: F11 is mixed with 50 mL of acetonitrile. After heating for 15 min under reflux of the solvent, a type of viscous black oil is deposited on the walls of the flask and the supernatant is separated immediately. This operation is repeated and P15 (696.5 mg, mixture of calixarenes the Mp of which corresponds to 34 units) and, after assembly of the filtrates, F15 (425.6 mg) are obtained.

R: F15 is placed under stirring in 50 mL of acetonitrile at ambient temperature for 24 h. F16 (30 mg, pure calix[13] arene) and P16 (401 mg, two populations the Mps of which correspond to 18 and 12 units) are obtained.

Figure 21:
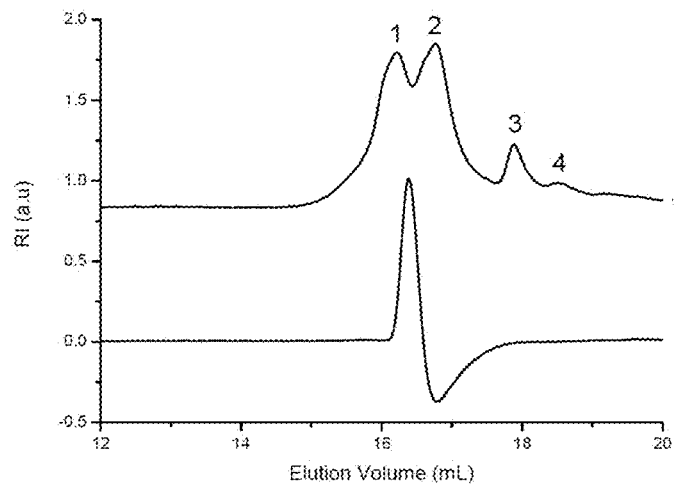
Figure 21:
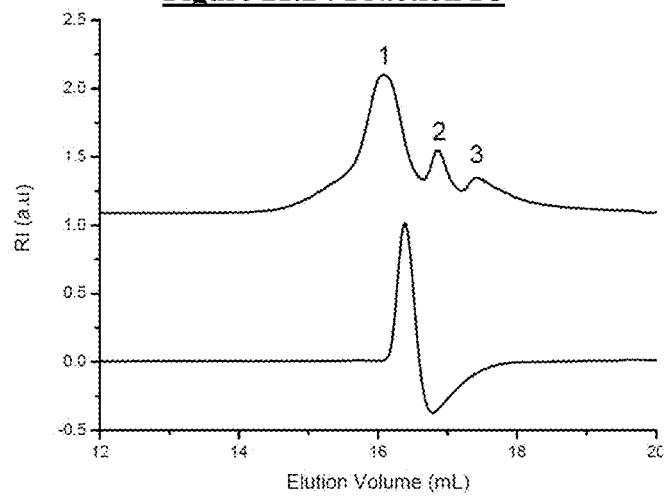
Figure 21:
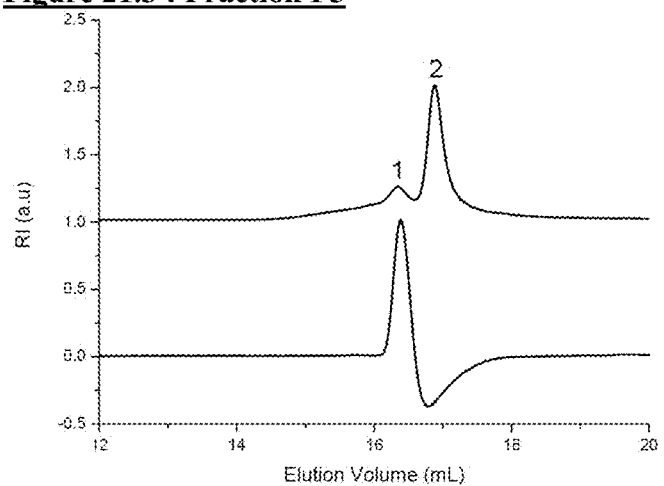

FIG. 21 shows the set of size exclusion chromatographies carried out on the mixtures of large calixarenes originating from the purification diagram shown in FIG. 3. Each chromatogram includes the reference calix[16]arene.

Figure 22:
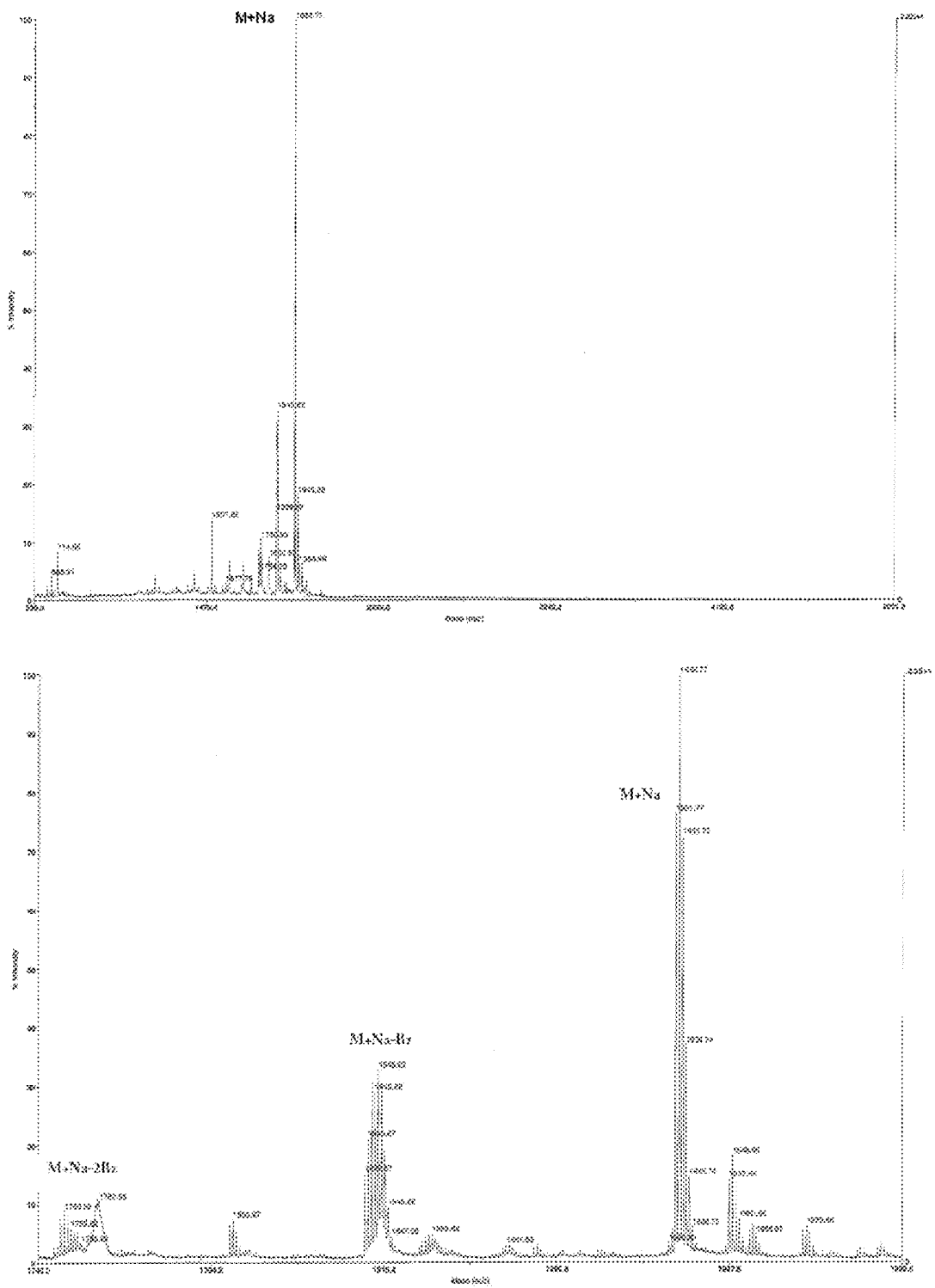

FIG. 22 shows the Maldi-Tof mass spectra of the pure samples of p-(benzyloxy)calix[9]arene, p-(benzyloxy)calix[10]arene, p-(benzyloxy)calix[12]arene and p-(benzyloxy)calix[16]arene. This technique makes it possible to accurately determine the molar mass of a compound in order to arrive at its chemical composition.

Figure 23:
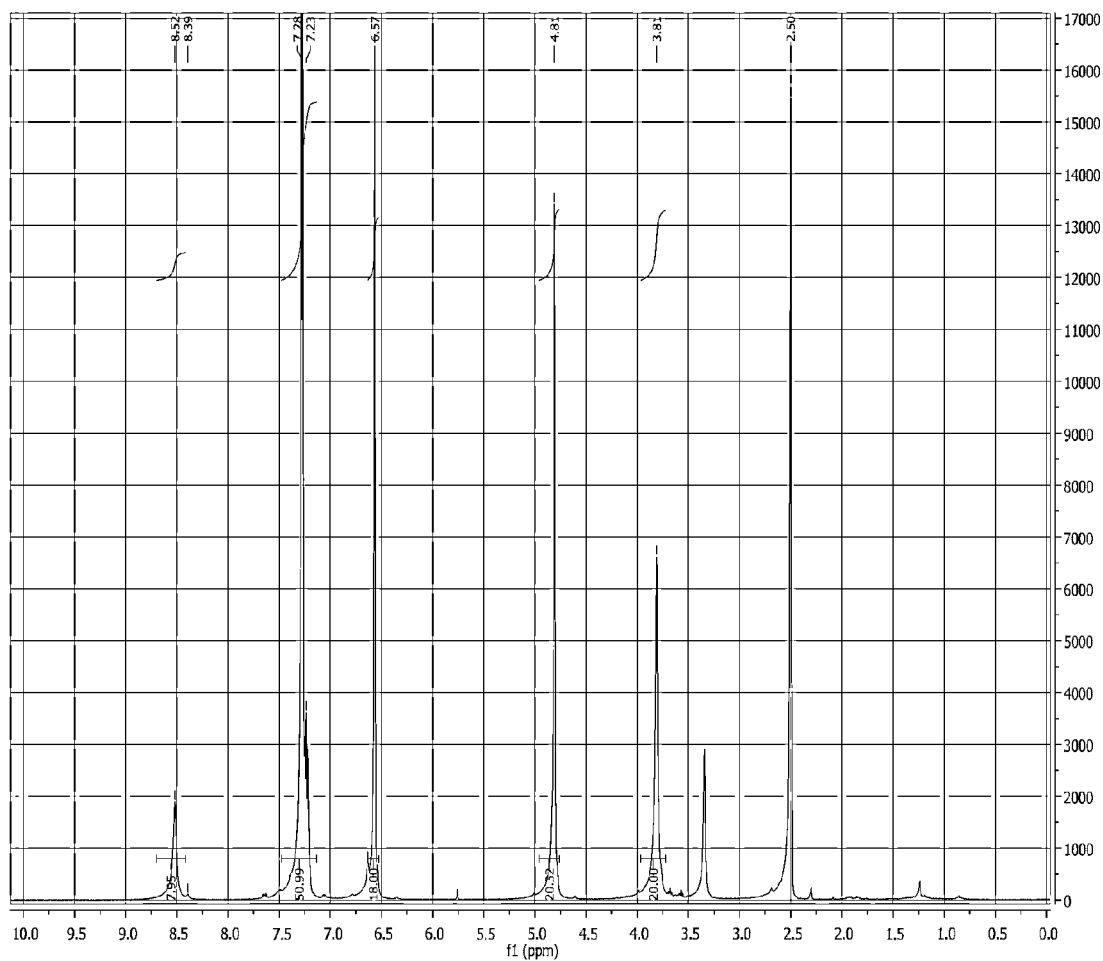

FIG. 23 shows the NMR spectra of the pure samples of p-(benzyloxy)calix[9]arene, p-(benzyloxy)calix[10]arene, p-(benzyloxy)calix[12]arene, p-(benzyloxy)calix[13]arene and p-(benzyloxy)calix[16]arene.

Figure 24:
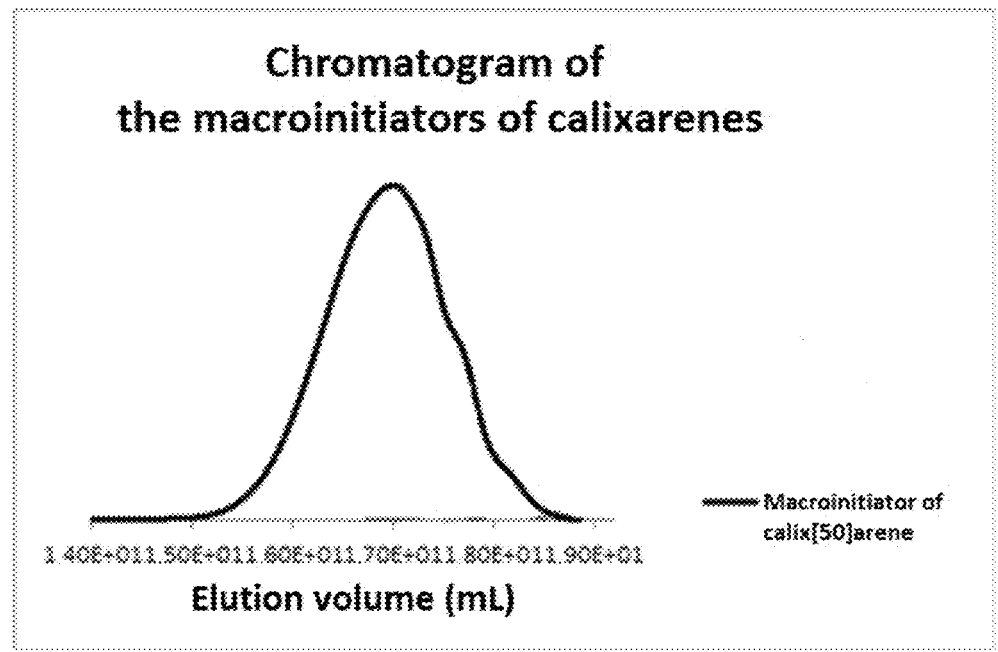

FIG. 24 shows the GPC chromatogram of the macroinitiator obtained from calix[50]arene (Example C).

Figure 25:
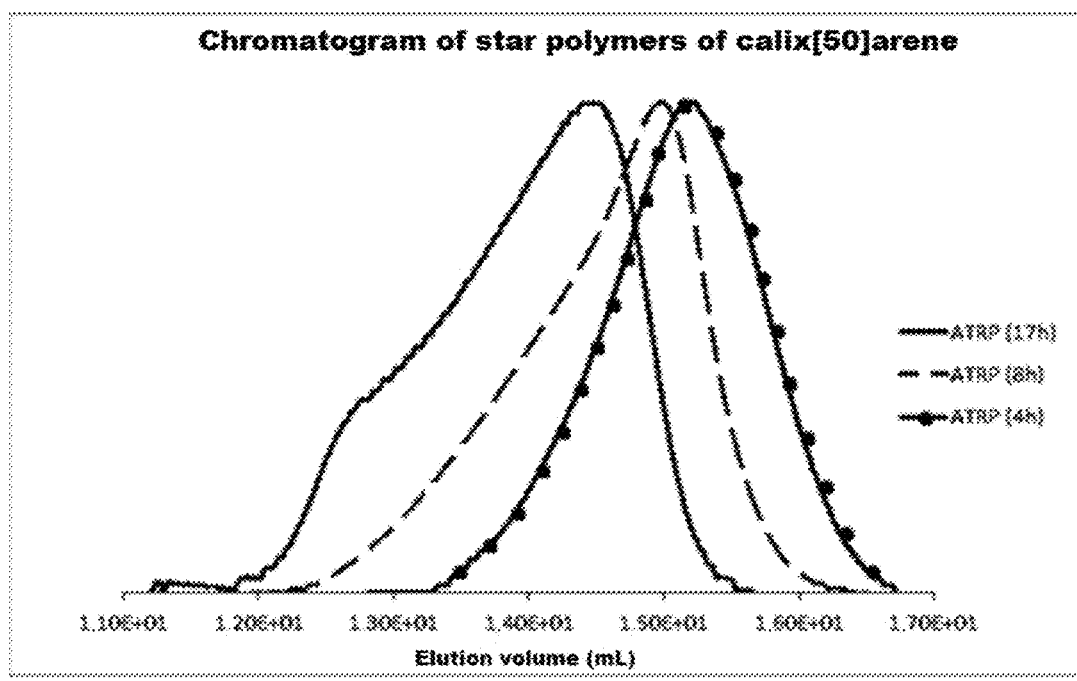

FIG. 25 shows the GPC chromatogram of the star polymers obtained from calix[50]arene, said polymers differing by the duration of the ATRP process.

Figure 26:
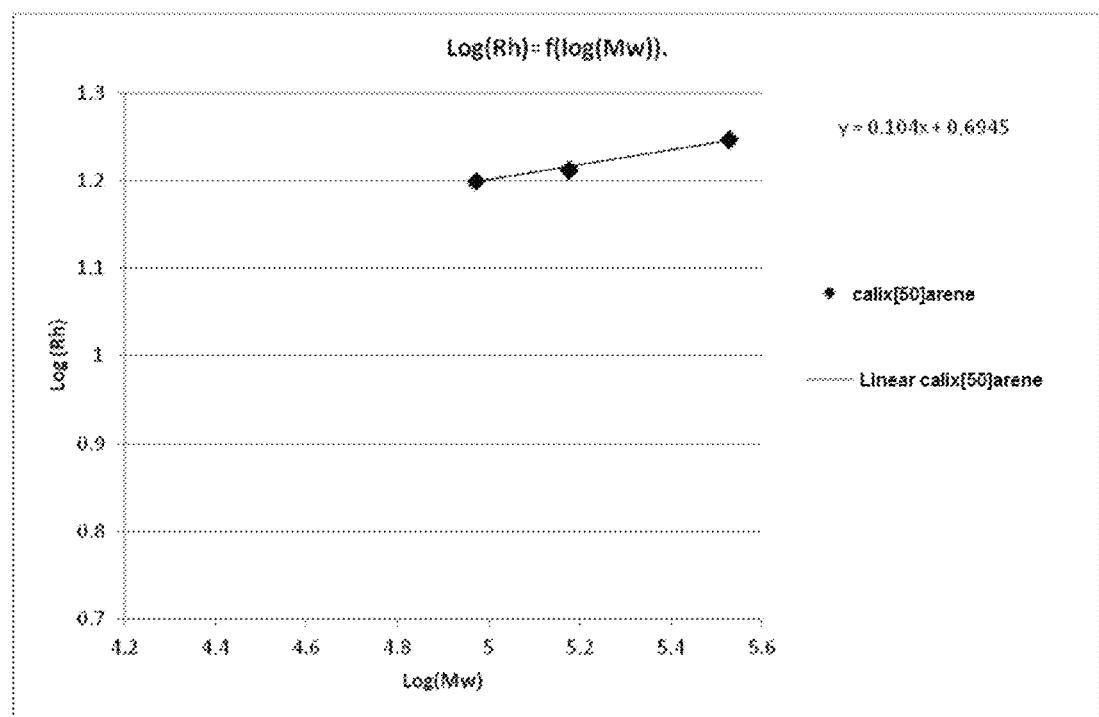

FIG. 26 shows the characterization of the structures of the star polymers, by expressing log Rh where Rh corresponds to the hydrodynamic radius of the polymer studied, as a function of log Mw where Mw is the molar mass of polymer.

Figure 27:
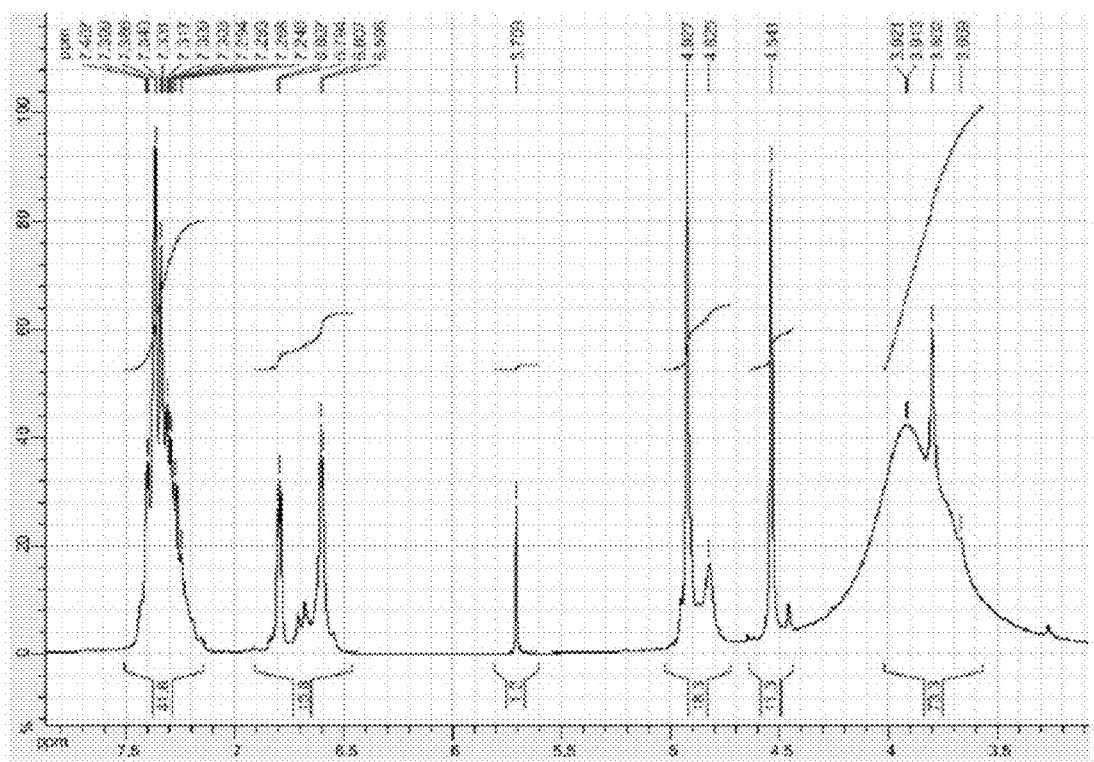

FIG. 27 shows a $^1$H NMR analysis of the solid obtained in Example 1d)D.

Figure 28:
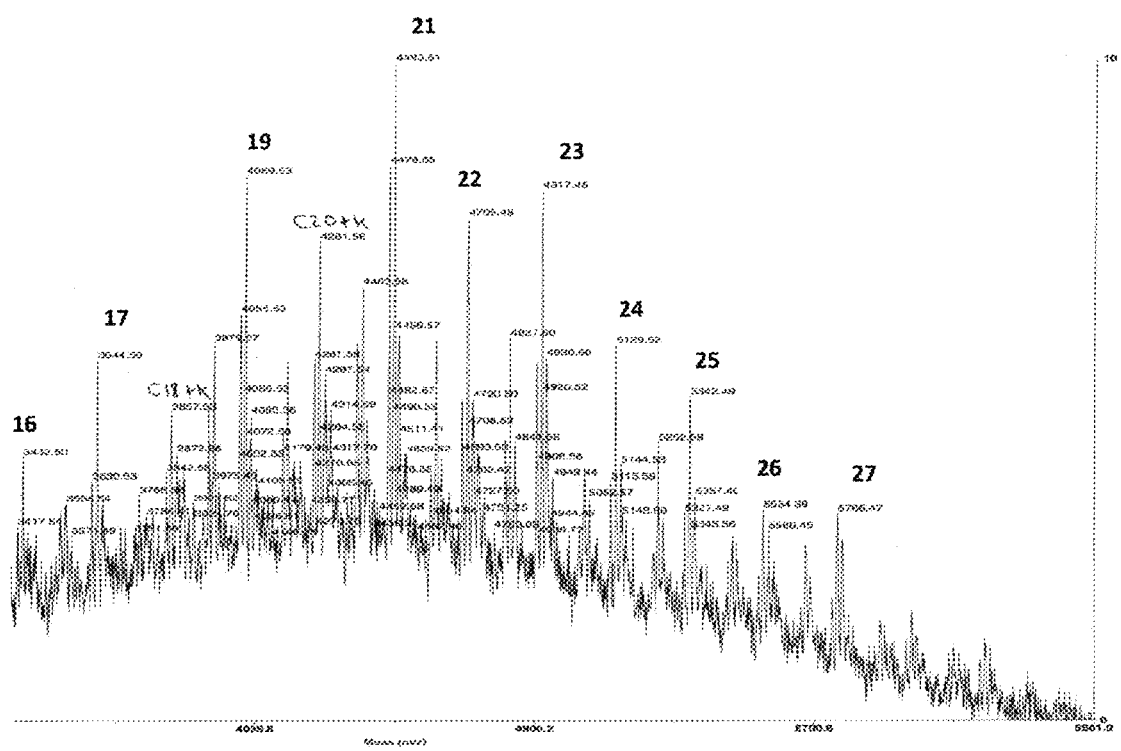

FIG. 28 shows a "MALDI" mass spectrometry analysis of the giant calixarenes obtained using 0.4 equivalents of LiOH with respect to the phenol (Example 1d)D). The values indicated correspond to the number of phenolic units. The calixarenes appear mainly potassium-cationized (sodium cationization observed in the minority). The peaks at M-91 correspond to debenzylation reactions of the calixarenes induced by the laser beam (during the analysis).

Figure 29A:
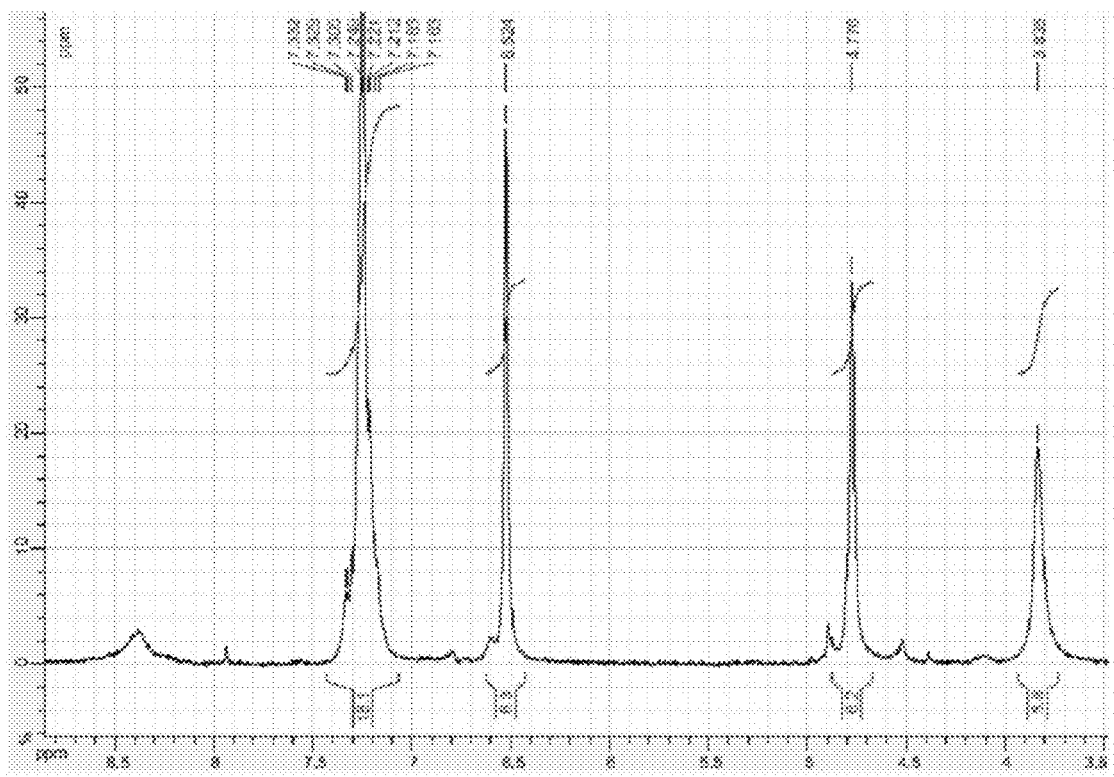

FIG. 29a shows a $^1$H NMR analysis of the purified mixture of giant calixarenes obtained using 0.4 equivalents of CsOH (Example 1d)E).

Figure 29B:
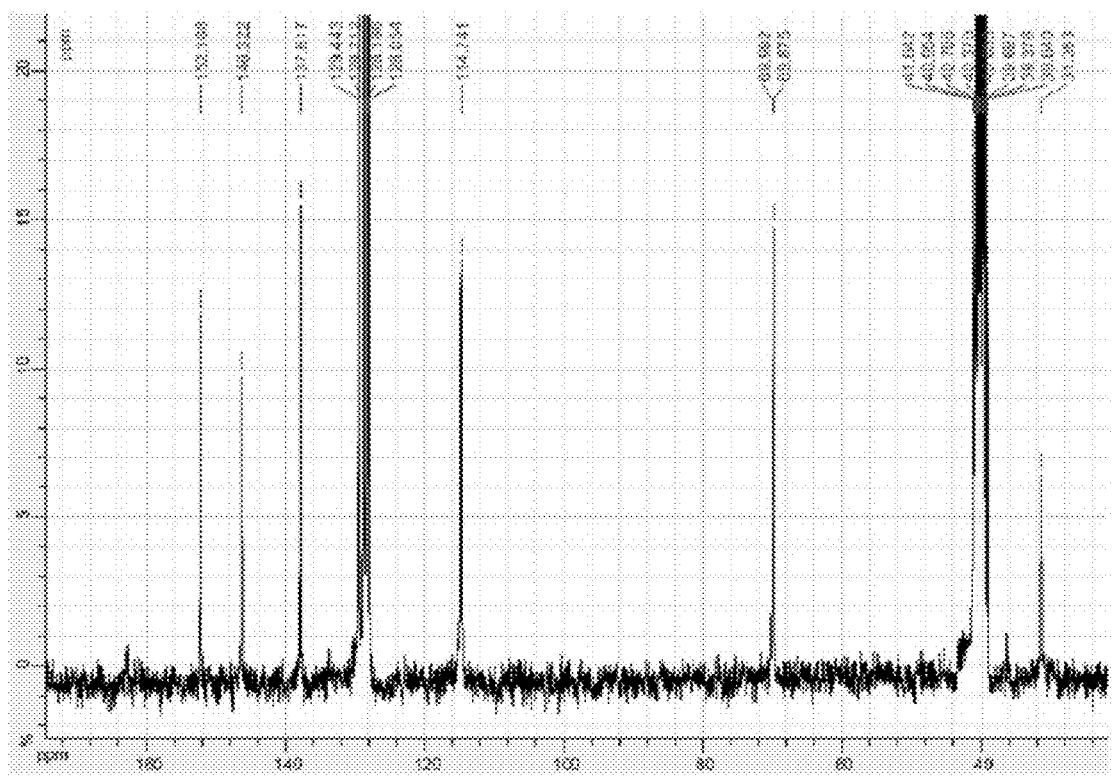

FIG. 29b shows a $^{13}$C NMR (63 MHz) analysis of the purified mixture of giant calixarenes obtained using 0.4 equivalents of CsOH (Example 1d)E).

EXAMPLES

A) Synthesis of Giant Calixarenes

Example 1: Preparation of Giant p-(benzyloxy)calixarenes a) By Reaction of Benzyloxyphenol with a Base and Formaldehyde in Water and Removal of the Water. Solid Precursor in the Form of an Isolated Brittle Resin.

A 2-liter three-necked flask equipped with a mechanical stirrer, a Dean-Stark trap and a condenser as well as heating using an oil bath, is loaded with 104 g of 4-(benzyloxy) phenol (0.519 mol) and 135 ml of formaldehyde in an aqueous solution at 30%.

The resulting suspension is heated at 140° C. under the protection of argon.

A solution of 12 g of KOH (0.214 mol; 0.41 equivalent) in 10 ml of water is rapidly injected at 90° C., while continuing heating. The white suspension transforms into a bright yellow clear solution. This solution is maintained under reflux for 1 h.

One of the ground glass necks of the flask is then equipped with a swan-neck connected to a bubbler, and the solution is then subjected to vigorous flushing with argon (≈20 bubbles/s), the argon inlet being via the top of the condenser.

At the end of approximately 40 min of flushing, the initially clear and fluid solution becomes more and more viscous, and finally solidifies at the end of 1 h.

The hard and brittle solid resin obtained is washed with a mixture of 750 ml of methanol, acidified with 50 ml of 37% HCl in an aqueous solution. The precursor is dispersed under vigorous mechanical stirring.

The resulting suspension is filtered.

An NMR analysis shows that this precursor isolated in this way appears to be 50% constituted by giant calixarenes. The main impurity is the dimer, plus a small percentage of linear oligomers.

This precursor is dissolved in 1 liter of an acetone/DMSO mixture (90:10 by volume) and is placed in a refrigerator to crystallize (1° C./4 days). 20 g of a microcrystalline solid is recovered, the NMR analysis of which is shown in FIG. 4. This solid comprises approximately 80% of giant calixarenes.

Measurement of the molar mass using GPC: 4600 g/mol, number of repeat units=22.

Measurement of the hydrodynamic radius of the calixarenes formed using dynamic light scattering (DLS): 4 nm.

b) By Reaction of Benzyloxyphenol with a Base and Formaldehyde in Water and Removal of the Water then Heat Treatment of the Solid Precursor in the Form of a Brittle Resin, not Isolated, in Octane Under Reflux A 2-liter three-necked flask equipped with a mechanical stirrer, a Dean-Stark trap and a condenser as well as heating using an oil bath, is loaded with 104 g of 4-(benzyloxy) phenol (0.519 mol) and 135 ml of formaldehyde in an aqueous solution at 30%.

The resulting suspension is heated at 140° C. under the protection of argon.

A solution of 12 g of KOH (0.214 mol; 0.41 equivalent) in 10 ml of water is rapidly injected at 90° C., while continuing heating. The white suspension transforms into a bright yellow clear solution. This solution is maintained under reflux for 1 h.

One of the ground glass necks of the flask is then equipped with a swan-neck connected to a bubbler, and the solution is then subjected to vigorous flushing with argon (20 bubbles/s), the argon inlet being via the top of the condenser.

At the end of approximately 40 min of flushing, the initially clear and fluid solution becomes more and more viscous, and finally solidifies at the end of 1 h.

This solid resin then has 300 ml of octane added to it and the system is placed under reflux without stirring for 3 h30. NMR analysis of the solid obtained is shown in FIG. 5a.

This solid appears to be 60% constituted by giant calixarenes.

This solid is dissolved in 2 liters of an acetone/DMSO mixture (90:10 by volume) and is placed in a refrigerator to crystallize (1° C./4 days). 32 g of giant calixarenes is recovered. The NMR (DMSO)-d6 of this the product is shown in FIG. 5b. Yield: 30%

Measurement of the hydrodynamic radius of the calixarenes formed by DLS scattering: 4.5 nm. Estimation of number of repeat units is n=30.

c) By Reaction of Benzyloxyphenol with a Base and Formaldehyde in Water and Removal of the Water then Heat Treatment of the Solid Precursor in the Form of a Brittle Resin, not Isolated, in a Silicone Oil (140° C.).

A sample of 10 g of solid precursor (not neutralized) obtained in Example 1b (KOH 0.4 equivalent) is immersed in 100 ml of silicone oil in a 250 ml Schlenk flask, and heated at 140° C. for 8 h. A proton NMR analysis shows that the resulting solid is 68% constituted by giant calixarenes.

c-2) by Reaction of Benzyloxyphenol with a Base and Formaldehyde in Water and Removal of the Water then Heat Treatment of the Solid Precursor in the Form of a Brittle Resin, not Isolated, in an Oven (140° C.).

A sample of 10 g of solid precursor (not neutralized) obtained in Example 1.d)C (KOH 1 equivalent) is placed in a Schlenk tube and degassed under primary vacuum for 3 h, in order to remove the volatile residues (water, residual formaldehyde).

This product is then placed in an oven at 140° C. for 22 h. A proton NMR analysis shows that the resulting solid is 60% constituted by giant calixarenes.

d) By Reaction of Benzyloxyphenol with a Base and Formaldehyde in Water and Removal of the Water then Heat Treatment of the Solid Precursor in the Form of a Brittle Resin, not Isolated, in Xylene or Toluene Under Reflux with Stirring.

Example A: KOH (0.4 Equivalent with Respect to the Phenol)

A 2-liter three-necked flask equipped with a mechanical stirrer, a Dean-Stark trap and a condenser as well as heating using an oil bath, is loaded with 104 g of 4-(benzyloxy) phenol (0.519 mol) and 135 ml of formaldehyde in an aqueous solution at 30%.

The resulting suspension is heated at 140° C. under the protection of argon.

A solution of 12 g of KOH (0.214 mol; 0.41 equivalent) in 10 ml of water is rapidly injected at 90° C., while continuing heating. The white suspension transforms into a bright yellow clear solution. This solution is maintained under reflux for 1 h.

One of the ground glass necks of the flask is then equipped with a swan-neck connected to a bubbler, and the solution is then subjected to vigorous flushing with argon (20 bubbles/s), the argon inlet being via the top of the condenser.

At the end of approximately 40 min of flushing, the initially clear and fluid solution becomes more and more viscous, and finally solidifies at the end of 1 h.

Then 600 ml of xylene is added to this solid, and the resulting suspension is taken to reflux under vigorous mechanical stirring, so as to thoroughly redisperse the solid precursor during this period of time.

After neutralization with a mixture of 500 ml of THF/50 ml of 37% HCl under vigorous stirring, filtration of the suspension obtained makes it possible to recover 40 g of p-(benzyloxy)calix[8]arene.

The filtrate is evaporated to dryness. The solid obtained is dissolved in 1 liter of an acetone/DMSO mixture (90:10 by volume) and crystallized in a refrigerator (1° C./4 days). 17 g of a microcrystalline solid is recovered, the NMR analysis of which (DMSO-d6) is shown in FIG. 6.

This solid appears to be 95% constituted by giant calixarenes.

The measurement of the molar mass using GPC is shown in FIG. 7: M=6000 g/mol, number of phenolic units (n)=28.

Measurement of the hydrodynamic radius of the calixarenes formed using DLS: D (diameter)=4.5 nm.

Example B: Ba(OH)$_2$ (0.4 Equivalent with Respect to the Phenol)

A) A solution of 60 g of Ba(OH)$_2$.8H$_2$O (0.19 mol; 0.4 equivalent) in 135 ml of aqueous formaldehyde at 30% is prepared in a 250 ml Erlenmeyer flask, under vigorous magnetic stirring. A white suspension is obtained, hereafter called "solution A".

B) A 2-liter three-necked flask equipped with a mechanical stirrer, a Dean-Stark trap and a condenser as well as heating using an oil bath, is loaded with 104 g of 4-(benzyloxy)phenol (0.519 mol). Solution A is added thereto. Then heating of the resulting suspension is started (140° C.), under the protection of argon.

At a measured temperature of 50° C. 40 ml of ethanol is then added, while continuing heating. The white suspension then instantaneously transforms into a bright yellow clear solution. This solution is maintained under reflux for 1 h.

One of the ground glass necks of the flask is then equipped with a swan-neck connected to a bubbler, and the bright yellow clear solution is then subjected to vigorous flushing with argon (20 bubbles/s), the argon inlet being via the top of the condenser.

At the end of approximately 40 min of flushing, the initially clear and fluid solution becomes more and more viscous, and finally solidifies at the end of 1 h of flushing of argon.

Then 300 ml of xylene is added to this solid, and the resulting suspension is taken to reflux under stirring for 8 h.

After returning to ambient temperature, the suspension is filtered, then the precipitate is neutralized by being placed in suspension in a mixture of 500 ml of methanol/50 ml of 37% HCl, under vigorous stirring.

After filtration, a brown solid is recovered, which is dissolved in 1 liter of an acetone/DMSO mixture (90:10 by volume). This solution is immediately filtered in order to isolate p-(benzyloxy)calix[8]arene.

After storage in a refrigerator (1° C.) for 4 days, 63 g of a microcrystalline precipitate is recovered, the NMR analysis of which (DMSO-d6) is shown in FIG. 8.

The solid obtained in this way appears to be 90% constituted by giant calixarenes.

The measurement of the molar mass using GPC is shown in FIG. 9: the peak molar mass (centred Gaussian)=10400, i.e. n=50.

Measurement of the hydrodynamic radius of the calixarenes formed using DLS: D (diameter)=7 nm.

Example C: KOH (1 Equivalent with Respect to the Phenol)

A 2-liter three-necked flask equipped with a mechanical stirrer, a Dean-Stark trap and a condenser as well as heating using an oil bath, is loaded with 104 g of 4-(benzyloxy)phenol (0.519 mol) and 135 ml of formaldehyde in an aqueous solution at 30%.

The resulting suspension is heated at 140° C. under the protection of argon.

A solution of 28 g of KOH (0.519 mol; 1 equivalent) in 20 ml of water is rapidly injected at 90° C., while continuing heating. The white suspension transforms into a bright yellow clear solution. This solution is maintained under reflux for 1 h.

One of the ground glass necks of the flask is then equipped with a swan-neck connected to a bubbler, and the solution is then subjected to vigorous flushing with argon (20 bubbles/s), the argon inlet being via the top of the condenser.

At the end of approximately 40 min of flushing, the initially clear and fluid solution becomes more and more viscous, and finally solidifies at the end of 1 h.

NMR analysis (DMSO-d6) of this solid obtained in this way is shown in FIG. 10*a*.

This solid appears to be constituted mainly by the dimer, accompanied by a lower proportion of linear oligomers.

Then 400 ml of xylene is added to this solid, and the resulting suspension is taken to reflux under stirring for 3 h.

After neutralization with a mixture of 500 ml of THF/50 ml of 37% HCl under vigorous stirring, filtration of the suspension obtained makes it possible to recover 15 g of p-(benzyloxy)calix[8]arene.

The filtrate is evaporated to dryness. The solid obtained is dissolved in 1 liter of an acetone/DMSO mixture (90:10 by volume) and crystallized in a refrigerator (1° C./4 days). A microcrystalline solid is recovered.

Measurement of the hydrodynamic radius of the calixarenes formed using DLS: D (diameter)=6 nm, for a number of phenolic units estimated at 50 (centred Gaussian using GPC).

NMR analysis of this solid is shown in FIG. 10*b*.

Example C-2: KOH (1 Equivalent with Respect to the Phenol), Production of Calix[80]Arenes A 2-liter three-necked flask equipped with a mechanical stirrer and "Dean-Stark"-type water trap is loaded with a suspension of 104 g of 4-(benzyloxy)phenol (0.52 mol), 28 g of KOH (0.5 mol) and 100 ml of a 37% formaldehyde solution (1.34 mol). After 20 minutes of reflux, a bright yellow clear solution is obtained.

While still maintaining reflux, a strong stream of argon is then established inside the flask, with the aim of removing the water. The initially very fluid reaction medium becomes more and more viscous, until it completely solidifies into a brittle solid with a yellow colour.

After returning to ambient temperature, 400 ml of xylene is then added. The suspension obtained in this way is then taken to reflux under stirring. Monitoring the reaction then shows an evolution of the composition towards the formation of giant calixarenes.

At the end of 4 h of reflux, 50 ml of 37% hydrochloric acid is added, as well as one liter of methanol, under vigorous mechanical stirring. The resulting suspension is filtered. After drying, a white solid obtained in this way is dissolved in a mixture of 100 ml of DMSO and 1000 ml of acetone, then filtered. The white solid obtained in this way is dried in air, then placed in suspension in 300 ml of THF. The filtrate recovered after filtration is evaporated to dryness, then washed with 50 ml of acetone. After removal of the supernatant, 2 g of giant calixarenes is obtained (size estimated using GPC (centred Gaussian):80 phenolic units).

The $^1$H NMR analysis of this product is shown in FIG. 10*c*.

Example D: LiOH (0.4 Equivalent with Respect to the Phenol)

A 2-liter three-necked flask equipped with a mechanical stirrer and "Dean-Stark"-type water trap is loaded with a suspension of 100 g of 4-(benzyloxy)phenol (0.5 mol), 8.4 g of LiOH.H$_2$O (0.2 mol) and 100 ml of a 37% formaldehyde solution (1.34 mol). After refluxing for 20 minutes, a bright yellow clear solution is obtained.

While still maintaining reflux, a strong stream of argon is then established inside the flask, with the aim of removing the water. The initially very fluid reaction medium becomes more and more viscous, until it completely solidifies into a brittle solid with a yellow colour.

$^1$H NMR analysis of this solid shows that it is constituted almost exclusively by the phenolic dimer (FIG. 27).

After returning to ambient temperature, 400 ml of xylene is then added. The suspension obtained in this way is then taken to reflux under vigorous stirring. Monitoring the reaction shows an evolution of the composition towards the formation of giant calixarenes.

At the end of 2 h of reflux, 50 ml of 37% hydrochloric acid is added, as well as one liter of methanol, under vigorous mechanical stirring. The resulting suspension is filtered, and the precipitate obtained in this way is dried in air. An NMR analysis shows that the reaction medium contains 40% of giant calixarenes.

An analysis by "MALDI" mass spectrometry confirms the presence of these calixarenes (FIG. 28).

Example E: CsOH (0.4 Equivalent with Respect to the Phenol)

A 2-liter three-necked flask equipped with a mechanical stirrer and "Dean-Stark"-type water trap is loaded with a suspension of 104 g of 4-(benzyloxy)phenol (0.52 mol), 36 ml of a solution of CsOH at 50% (0.208 mol) and 100 ml of a 37% formaldehyde solution (1.34 mol). After 20 minutes of reflux, a bright yellow clear solution is obtained.

While still maintaining reflux, a strong stream of argon is then established inside the flask, with the aim of removing the water. The initially very fluid reaction medium becomes more and more viscous, until it completely solidifies into a brittle solid with a yellow colour.

After returning to ambient temperature, 200 ml of xylene is then added. The suspension obtained in this way is then taken to reflux under stirring. Monitoring the reaction then shows an evolution of the composition towards the formation of giant calixarenes.

At the end of 2 h of reflux, 50 ml of 37% hydrochloric acid is added, as well as 500 ml of tetrahydrofuran, under vigorous mechanical stirring. The resulting suspension is evaporated to dryness. The resulting solid is washed with 2 liters of methanol, then filtered. After drying, the white solid obtained in this way is recrystallized from a mixture of 100 ml of DMSO and 1000 ml of acetone.

After filtration, the filtrate is left in a refrigerator (1° C.) for 3 days.

After filtration of the solid which has spontaneously precipitated, 30 g of giant calixarenes is obtained (size estimated using GPC: 20 phenolic units). Yield: 28%.

An NMR analysis of this product is shown in FIG. 29a.
A $^{13}$C analysis of this same product is shown in FIG. 29b.

e) By Reaction of Benzyloxyphenol with a Base and Formaldehyde in Water and Removal of the Water then Heat Treatment of the Solid Precursor in the Form of a Brittle Resin, not Isolated, in Xylene or Toluene Under Reflux without Stirring.

Example A: RbOH (0.4 Equivalent with Respect to the Phenol)

A 2-liter three-necked flask equipped with a mechanical stirrer, a Dean-Stark trap and a condenser as well as heating using an oil bath, is loaded with 104 g of 4-(benzyloxy) phenol (0.519 mol) and 135 ml of formaldehyde in an aqueous solution at 30%.

The resulting suspension is heated at 140° C. under the protection of argon.

25.2 ml of a solution of RbOH at 50% by weight in water (0.4 equivalent) is rapidly injected at 90° C. The white suspension transforms into a bright yellow clear solution. This solution is maintained under reflux for 1 h.

One of the ground glass necks of the flask is then equipped with a swan-neck connected to a bubbler, and the solution is then subjected to vigorous flushing with argon (20 bubbles/s), the argon inlet being via the top of the condenser.

At the end of approximately 40 min of flushing, the initially clear and fluid solution becomes more and more viscous, and finally solidifies at the end of 1 h.

170 ml of xylene is then added to this solid, and the resulting suspension is taken to reflux without stirring for 2 h.

The reaction medium is then neutralized by the addition of a mixture of 500 ml of methanol and 70 ml of 37% HCl in water under vigorous stirring.

After filtration of the solid and drying under vacuum, the solid is dissolved in 2 liters of an acetone/DMSO mixture (90:10 by volume).

Filtration of the suspension obtained makes it possible to recover 10 g of p-(benzyloxy)calix[8]arene.

The filtrate is then placed in a refrigerator (1° C./4 days).

25 g of a microcrystalline solid is recovered, the NMR analysis of which is shown in FIG. 11. This solid appears to be 90% constituted by giant calixarenes.

Measurement of the molar mass of this solid using GPC is shown in FIG. 12: M=6000 g/mol, number of phenolic units (n)=29 (centred Gaussian).

Measurement of the hydrodynamic radius of the calixarenes formed using DLS: D (diameter)=4.6 nm.

Example B: KOH (0.4 Equivalent with Respect to the Phenol)

A 2-liter three-necked flask equipped with a mechanical stirrer, a Dean-Stark trap and a condenser as well as heating using an oil bath, is loaded with 104 g of 4-(benzyloxy) phenol (0.519 mol) and 135 ml of formaldehyde in an aqueous solution at 30%.

The resulting suspension is heated at 140° C. under the protection of argon.

12 g of KOH in 10 ml of water (0.4 equivalent) is rapidly injected at 90° C. The white suspension transforms into a bright yellow clear solution. This solution is maintained under reflux for 1 h.

One of the ground glass necks of the flask is then equipped with a swan-neck connected to a bubbler, and the solution is then subjected to vigorous flushing with argon (20 bubbles/s), the argon inlet being via the top of the condenser.

At the end of approximately 40 min of flushing, the initially clear and fluid solution becomes more and more viscous, and finally solidifies at the end of 1 h.

170 ml of xylene is then added to this solid, and the resulting suspension is taken to reflux without stirring for 2 h.

The reaction medium is then neutralized by the addition of a mixture of 500 ml of methanol and 70 ml of 37% HCl in water under vigorous stirring.

After filtration and drying under vacuum, the solid is dissolved in 2 liters of an acetone/DMSO mixture (90:10 by volume).

Filtration of the suspension obtained makes it possible to recover 10 g of p-(benzyloxy)calix[8]arene.

The filtrate is then placed in a refrigerator (1° C./4 days).

35 g of a microcrystalline solid is recovered, the NMR analysis of which (DMSO-d6) shows that it appears to be 90% constituted by giant p-(benzyloxy) calixarenes.

Recrystallization of this solid from dichlorobenzene makes it possible to recover 10 g of a brown solid of improved purity, the NMR analysis of which (DMSO-d6) is shown in FIG. 13.

This solid appears to be more than 95% constituted by giant calixarenes.

Measurement of the molar mass using GPC is shown in FIG. 14: M=12700 g/mol, number of phenolic units (n)=60 (centred Gaussian).

Measurements of the hydrodynamic radius of the calixarenes formed using DLS: D (diameter)=8 nm.

Example C: KOH (0.13 Equivalent with Respect to the Phenol)

A 2-liter three-necked flask equipped with a mechanical stirrer, a Dean-Stark trap and a condenser as well as heating using an oil bath, is loaded with 104 g of 4-(benzyloxy) phenol (0.519 mol) and 135 ml of formaldehyde in an aqueous solution at 30%.

The resulting suspension is heated at 140° C. under the protection of argon.

A solution of 3.7 g of KOH (0.066 mol; 0.13 equivalent) in 5 ml of water is rapidly injected at 90° C., while continuing heating. The white suspension transforms into a bright yellow clear solution. This solution is maintained under reflux for 1 h.

One of the ground glass necks of the flask is then equipped with a swan-neck connected to a bubbler, and the solution is then subjected to vigorous flushing with argon (20 bubbles/s), the argon inlet being via the top of the condenser.

At the end of approximately 40 min of flushing, the initially clear and fluid solution becomes more and more viscous, and finally solidifies at the end of 3 h.

200 ml of xylene is then added to this solid, and the resulting suspension is taken to reflux without stirring for 2 h.

After neutralization with a mixture of 500 ml of THF/50 ml of 37% HCl under vigorous stirring, filtration of the suspension obtained makes it possible to recover 15 g of p-(benzyloxy)calix[8]arene.

The filtrate is evaporated to dryness. The solid obtained is dissolved in 1 liter of an acetone/DMSO mixture (90:10 by volume) and crystallized in a refrigerator (1° C./4 days). 50 g of a microcrystalline solid is recovered, 90% constituted by giant calixarenes.

DLS: average diameter measured=4.7 nm, which corresponds to a number of phenolic units estimated at 35.

f) By Reaction of Benzyloxyphenol with a Base and Formaldehyde in Water and Retention of the Water then Heat Treatment of the Solid Precursor in the Form of a Brittle Resin, not Isolated, in Octane Under Reflux.

A 250 ml three-necked flask equipped with a mechanical stirrer is loaded with 22.6 g (double space) (0.113 mol) of 4-(benzyloxy)phenol, 30 ml of 37% formaldehyde in an aqueous solution and 2.53 g (0.045 mol, 0.4 equivalent with respect to the phenol) of KOH in pellets.

The bright yellow clear solution obtained in this way is placed under reflux with mechanical stirring and under argon. At the end of approximately 1 h, the formation of a precipitate within the aqueous phase is observed.

40 ml of octane is then added, and the solution is taken to reflux. At the end of 1 h, the reaction medium solidifies. The heating and the stirring are stopped.

The solid obtained in this way is washed with a mixture of 200 ml of methanol and 10 ml of 37% HCl, under vigorous stirring.

After filtration, a white solid is recovered quantitatively, the NMR analysis of which shows that it is 60% constituted by giant calixarenes.

g) By Reaction of Benzyloxyphenol with a Base and Formaldehyde in Water and Retention of the Water then Heat Treatment of the Solid Precursor in the Form of a Brittle Resin, not Isolated, in Xylene or Toluene Under Reflux.

A 250 ml three-necked flask equipped with a mechanical stirrer is loaded with 22.6 g (0.113 mol) of 4-(benzyloxy) phenol, 30 ml of 37% formaldehyde in an aqueous solution and 2.53 g (0.045 mol, 0.4 equivalent with respect to the phenol) of KOH in pellets.

The bright yellow clear solution obtained in this way is placed under reflux with mechanical stirring and under argon. At the end of approximately 1 h, the formation of a precipitate within the aqueous phase is observed.

40 ml of xylene is then added, and the solution is taken to reflux. At the end of 2 h, the reaction medium solidifies. The heating and the stirring are stopped.

The solid obtained in this way is washed with a mixture of 200 ml of methanol and of 10 ml of HCl at 37%, under vigorous stirring.

After filtration, a white solid is recovered quantitatively, the NMR analysis of which is shown in FIG. 15.

This solid appears to be 80% constituted by giant calixarenes.

Measurement of the molar mass using GPC: M=4600 g/mol, number of phenolic units (n)=22.

Measurement of the hydrodynamic radius of the calixarenes formed using DLS: D (diameter)=3.2 nm.

h) By Heat Treatment of the Dimer of Benzyloxyphenol, Isolated, in Octane Under Reflux.

A 2-liter three-necked flask equipped with a mechanical stirrer and "Dean-Stark"-type water trap is loaded with a suspension of 100 g of 4-(benzyloxy)phenol (0.5 mol), 8.4 g of LiOH.H$_2$O (0.2 mol) and 100 ml of a 37% formaldehyde solution (1.34 mol). After 20 minutes of reflux, a bright yellow clear solution is obtained.

While still maintaining reflux, a strong stream of argon is then established inside the flask, with the aim of removing the water. The initially very fluid reaction medium becomes more and more viscous, until it completely solidifies into a brittle solid with a yellow colour.

A $^1$H NMR analysis of this solid shows that it is almost exclusively constituted by the phenolic dimer (FIG. 27).

The reaction medium is then neutralized with an HCl/methanol mixture, under vigorous stirring.

After filtration and washing with water, a white solid is recovered quantitatively.

All of the solid thus recovered is placed in a 1 L two-necked flask. A solution of KOH (11 g) in 150 ml of methanol is added with mechanical stirring, under argon. At the end of 8 h, the methanol is evaporated off using a vane pump. 400 ml of octane is then added to the yellow solid obtained in this way. After fixing a water trap of the "Dean-Stark" type onto one of the ground glass necks, the medium is taken to reflux for 8 h. NMR monitoring of the reaction shows the evolution of the composition of the reaction medium towards the formation of giant calixarenes. Final proportion: 60%.

i) By Heat Treatment of the Dimer of Benzyloxyphenol, Isolated, in Xylene or Toluene Under Reflux.

A 2-liter three-necked flask equipped with a mechanical stirrer and "Dean-Stark"-type water trap is loaded with a suspension of 100 g of 4-(benzyloxy)phenol (0.5 mol), 8.4 g of $LiOH.H_2O$ (0.2 mol) and 100 ml of a 37% formaldehyde solution (1.34 mol). After 20 minutes of reflux, a bright yellow clear solution is obtained.

While still maintaining reflux, a strong stream of argon is then established inside the flask, with the aim of removing the water. The initially very fluid reaction medium becomes more and more viscous, until it completely solidifies into a brittle solid with a yellow colour.

A $^1H$ NMR analysis of this solid shows that it is constituted almost exclusively by phenolic dimer (FIG. 27).

The reaction medium is then neutralized with a HCl/methanol mixture, under vigorous stirring.

After filtration and washing with water, a white solid is recovered quantitatively.

All of the solid thus recovered is placed in a 1-liter two-necked flask. A solution of KOH (11 g) in 150 ml of methanol is added with mechanical stirring, under argon. At the end of 8 h, the methanol is evaporated off using a vane pump. 400 ml of xylene is then added to the yellow solid obtained in this way. After fixing a water trap of the "Dean-Stark" type onto one of the ground glass necks, the medium is taken to reflux for 4 h. NMR monitoring of the reaction shows the evolution of the composition of the reaction medium towards the formation of giant calixarenes. Final proportion: 40%.

j) By Reaction of Benzyloxyphenol with a Base and Formaldehyde in Water, and an Organic Solvent (without Removal of Water)

A 2-liter three-necked flask equipped with a mechanical stirrer and "Dean-Stark"-type water trap is loaded with a suspension of 100 g of 4-(benzyloxy)phenol (0.5 mol), 13 g of KOH (0.214 mol), 100 ml of a 37% formaldehyde solution (1.34 mol) and 800 ml of xylene. The yellow emulsion thus obtained is taken to reflux for 5 h.

NMR analysis shows that the reaction medium contains 60% giant calixarenes.

Example 2: Preparation of p-(Octyloxy)Calixarenes a) By Reaction of Octyloxyphenol with a Base and Formaldehyde in Water and Removal of the Water. Solid Precursor in the Form of an Isolated Brittle Resin.

In a 250 ml two-necked flask, a suspension of 25 g of 4-(octyloxy)phenol (0.113 mol), 30 ml of formaldehyde at 37% and 2.60 g of KOH (0.046 mol, 0.41 equivalent) is prepared under the protection of argon. At the end of 1 h of reflux, a bright yellow clear solution is obtained.

One of the ground glass necks of the flask is then equipped with a swan-neck connected to a bubbler, and the solution is then subjected to vigorous flushing with argon (20 bubbles/s), the argon inlet being via the top of the condenser.

At the end of approximately 40 min of flushing, the initially clear and fluid solution becomes more and more viscous, and finally solidifies at the end of two hours.

A bright yellow solid is obtained quantitatively.

NMR analysis ($CDCl_3$/DMSO) shows that this crude product appears to be 85% constituted by giant calixarenes.

The hard and brittle yellow solid obtained previously is dispersed under vigorous stirring in a solution of 10 ml of 37% HCl in 200 ml of methanol.

After filtration, a white solid is recovered quantitatively, the NMR analysis of which ($CDCl_3$/DMSO) is shown in FIG. 16.

This solid appears to be 95% constituted by giant calixarenes.

Measurement of the molar mass by gel permeation chromatography (GPC):

M=7700 g/mol, number of phenolic units (n)=35; average molar mass corresponding to 57 phenolic units.

Measurement of the hydrodynamic radius of the calixarenes formed using DLS: D (diameter)=4.2 nm.

b) By Reaction of Octyloxyphenol with a Base and Formaldehyde in Water and Removal of the Water then Heat Treatment of the Solid Precursor in the Form of a Brittle Resin, not Isolated, in Octane Under Reflux.

A suspension of 25 g of 4-(octyloxy)phenol (0.113 mol), 30 ml of formaldehyde at 37% and 2.60 g of KOH (0.046 mol, 0.41 equivalent) is prepared in a 250 ml two-necked flask, under the protection of argon. At the end of 1 h of reflux, a bright yellow clear solution is obtained.

One of the ground glass necks of the flask is then equipped with a swan-neck connected to a bubbler, and the solution is then subjected to vigorous flushing with argon (20 bubbles/s), the argon inlet being via the top of the condenser.

At the end of approximately 40 min of flushing, the initially clear and fluid solution becomes more and more viscous, and finally solidifies at the end of two hours.

A bright yellow solid is obtained quantitatively.

This solid then has 100 ml of octane added to it, and is taken to reflux for 8 h. After neutralization with a HCl/methanol mixture, a pale yellow solid is obtained quantitatively. A GPC analysis shows an increase in the size of the macrocycles obtained with respect to the preceding case (40 phenolic units, centred Gaussian).

c) By Reaction of Octyloxyphenol with a Base and Formaldehyde in Water and Removal of the Water then Heat Treatment of the Solid Precursor in the Form of a Brittle Resin, not Isolated, in Xylene or Toluene Under Reflux.

A suspension of 25 g of 4-(octyloxy)phenol (0.113 mol), 30 ml of formaldehyde at 37% and 2.60 g of KOH (0.046 mol, 0.41 equivalent) is prepared in a 250 ml two-necked flask, under the protection of argon. At the end of 1 h of reflux, a bright yellow clear solution is obtained.

One of the ground glass necks of the flask is then equipped with a swan-neck connected to a bubbler, and the solution is then subjected to vigorous flushing with argon (20 bubbles/s), the argon inlet being via the top of the condenser.

At the end of approximately 40 min of flushing, the initially clear and fluid solution becomes more and more viscous, and finally solidifies at the end of two hours.

A bright yellow solid is obtained quantitatively.

This solid then has 100 ml of xylene added to it, and is taken to reflux for 4 h. An NMR analysis shows a decrease in the proportion of giant calixarenes (60%). A GPC study shows that the size of the macrocycles obtained is 40 phenolic units (centred Gaussian).

d) By Reaction of Octyloxyphenol with a Base and Formaldehyde in Water and Retention of the Water then Heat Treatment of the Solid Precursor in the Form of a Brittle Resin, not Isolated, in Octane Under Reflux.

A suspension of 25 g of 4-(octyloxy)phenol (0.113 mol), 30 ml of formaldehyde at 37% and 2.60 g of KOH (0.046 mol, 0.41 equivalent) is prepared in a 250 ml two-necked flask, under the protection of argon. At the end of 1 h of reflux, a bright yellow clear solution is obtained. At the end of another 1 h of reflux, a clear brown precipitate appears in the reaction medium. After the addition of 50 ml of octane, the fluid and homogeneous suspension obtained in this way is placed under reflux for 2 h, at the end of which period of time a voluminous precipitate appears.

After neutralization with a solution of HCl in methanol and filtration, a pale yellow solid is obtained.

An NMR analysis shows a decrease in the proportion of giant calixarenes (60%). A GPC study shows that the size of the macrocycles obtained is 40 phenolic units (centred Gaussian).

e) By Reaction of Octyloxyphenol with a Base and Formaldehyde in Water and Retention of the Water then Heat Treatment of the Solid Precursor in the Form of a Brittle Resin, not Isolated, in Xylene or Toluene Under Reflux.

A suspension of 25 g of 4-(octyloxy)phenol (0.113 mol), 30 ml of formaldehyde at 37% and 2.60 g of KOH (0.046 mol, 0.41 equivalent) is prepared in a 250 ml two-necked flask, under the protection of argon. At the end of 1 h of reflux, a bright yellow clear solution is obtained. At the end of another 1 h of reflux, a clear brown precipitate appears in the reaction medium. After the addition of 50 ml of xylene, the fluid and homogeneous suspension obtained in this way is placed under reflux for 2 h, at the end of which period of time a voluminous precipitate appears. An NMR analysis shows a decrease in the proportion of giant calixarenes (50%). A GPC study shows that the size of the macrocycles obtained is 45 phenolic units (centred Gaussian).

f) By Heat Treatment of the Dimer of Octyloxyphenol, Isolated, in Octane Under Reflux.

A suspension of 25 g of 4-(octyloxy)phenol (0.113 mol), 30 ml of formaldehyde at 37% and 1.93 g of LiOH.H$_2$O (0.046 mol, 0.41 equivalent) is prepared in a 250 ml two-necked flask, under the protection of argon. At the end of 1 h of reflux, a bright yellow clear solution is obtained.

One of the ground glass necks of the flask is then equipped with a swan-neck connected to a bubbler, and the solution is then subjected to vigorous flushing with argon (20 bubbles/s), the argon inlet being via the top of the condenser.

At the end of approximately 20 min of flushing, the initially clear and fluid solution becomes more and more viscous, and finally solidifies at the end of one hour.

A bright yellow solid is obtained quantitatively, essentially constituted by the dimer of octyloxyphenol.

This solid is neutralized under vigorous stirring with HCl in methanol, then filtered. 2.60 g of KOH (0.046 mol, 0.41 equivalent) in solution in 50 ml of methanol is then added under argon, with mechanical stirring. At the end of 4 hours, the methanol is evaporated off using a vane pump.

100 ml of octane is then added and the reaction medium is put back under reflux for 4 h.

An NMR analysis of the yellow solid obtained shows that it is constituted by an 80% proportion of giant calixarenes. A GPC study shows that the size of the macrocycles obtained is 35 phenolic units (centred Gaussian).

g) By Heat Treatment of the Dimer of Octyloxyphenol, Isolated, in Xylene or Toluene Under Reflux.

A suspension of 25 g of 4-(octyloxy)phenol (0.113 mol), 30 ml of formaldehyde at 37% and 1.93 g of LiOH.H$_2$O (0.046 mol, 0.41 equivalent) is prepared in a 250 ml two-necked flask, under the protection of argon. At the end of 1 h of reflux, a bright yellow clear solution is obtained.

One of the ground glass necks of the flask is then equipped with a swan-neck connected to a bubbler, and the solution is then subjected to vigorous flushing with argon (20 bubbles/s), the argon inlet being via the top of the condenser.

At the end of approximately 20 min of flushing, the initially clear and fluid solution becomes more and more viscous, and finally solidifies at the end of one hour.

A bright yellow solid is obtained quantitatively, essentially constituted by the dimer of octyloxyphenol.

This solid is neutralized under vigorous stirring by HCl in methanol, then filtered.

2.60 g of KOH (0.046 mol, 0.41 equivalent) in solution in 50 ml of methanol is then added under argon, with mechanical stirring. At the end of 4 hours, the methanol is evaporated off using a vane pump.

100 ml of xylene is then added and the reaction medium is put back under reflux for 4 h.

An NMR analysis of the yellow solid obtained shows that it is constituted by an 80% proportion of giant calixarenes. A GPC study shows that the size of the macrocycles obtained is 33 phenolic units (centred Gaussian).

h) By Reaction of Octyloxyphenol with a Base and Formaldehyde in Water and an Organic Solvent (without Removal of the Water)

A suspension of 25 g of 4-(octyloxy)phenol (0.113 mol), 30 ml of formaldehyde at 37% and 2.60 g of KOH (0.046 mol, 0.41 equivalent) and 200 ml of xylene is prepared in a 250 ml two-necked flask, under the protection of argon.

The yellow emulsion obtained in this way is taken to reflux for 5 h.

An NMR analysis shows that the reaction medium contains 80% of giant calixarenes.

Example 2.1: Preparation of p-(methoxy)calixarenes a) By Reaction of 4-(Methoxy)Phenol with a Base and Formaldehyde in Water and then Removal of the Water. Solid Precursor in the Form of an Isolated Brittle Resin.

A 2-liter three-necked flask equipped with a mechanical stirrer and "Dean-Stark"-type water trap is loaded with a suspension of 65 g of 4-(methoxy)phenol (0.523 mol), 12 g of KOH (0.214 mol) and 100 ml of a 37% formaldehyde solution (1.34 mol). After 20 minutes of reflux, a bright yellow clear solution is obtained.

While still maintaining reflux, a strong stream of argon is then established inside the flask, with the aim of removing the water. The initially very fluid reaction medium becomes more and more viscous, until it completely solidifies into a brittle solid with a yellow colour. A $^1$H NMR analysis of this solid shows that it is 40% constituted by giant calixarenes.

b) By Reaction of 4-(Methoxy)Phenol with a Base and Formaldehyde in Water and Removal of the Water then Heat Treatment of the Solid Precursor in the Form of a Brittle Resin, not Isolated, in Octane Under Reflux.

A 2-liter three-necked flask equipped with a mechanical stirrer and "Dean-Stark"-type water trap is loaded with a suspension of 65 g of 4-(methoxy)phenol (0.523 mol), 12 g of KOH (0.214 mol) and 100 ml of a 37% formaldehyde solution (1.34 mol). After 20 minutes of reflux, a bright yellow clear solution is obtained.

While still maintaining reflux, a strong stream of argon is then established inside the flask, with the aim of removing the water. The initially very fluid reaction medium becomes more and more viscous, until it completely solidifies into a brittle solid with a yellow colour.

After returning to ambient temperature, 400 ml of octane is then added. The heterogeneous reaction medium obtained in this way is then taken to reflux without stirring. Monitoring the reaction then shows an evolution of the composition towards the formation of giant calixarenes.

At the end of 6 h of reflux, 50 ml of 37% hydrochloric acid is added, as well as one liter of methanol, under vigorous mechanical stirring. The resulting suspension is filtered, and the precipitate obtained in this way is dried in air. 60 g of a powdery solid is recovered. Yield: 92%. A GPC analysis shows that this solid is constituted by giant calixarenes (size estimated using GPC: 50 phenolic units).

c) By Reaction of 4-(Methoxy)Phenol with a Base and Formaldehyde in Water and Removal of the Water then Heat Treatment of the Solid Precursor in the Form of a Brittle Resin, not Isolated, in Xylene or Toluene Under Reflux.

A 2-liter three-necked flask equipped with a mechanical stirrer and "Dean-Stark"-type water trap is loaded with a suspension of 65 g of 4-(methoxy)phenol (0.523 mol), 12 g of KOH (0.214 mol) and 100 ml of a 37% formaldehyde solution (1.34 mol). After 20 minutes of reflux, a bright yellow clear solution is obtained.

While still maintaining reflux, a strong stream of argon is then established inside the flask, with the aim of removing the water. The initially very fluid reaction medium becomes more and more viscous, until it completely solidifies into a brittle solid with a yellow colour.

After returning to ambient temperature, 400 ml of xylene is then added. The suspension obtained in this way is then taken to reflux without stirring for 4 h. The reaction medium is neutralized with 50 ml of 37% hydrochloric acid in solution in 1 liter of methanol, under vigorous mechanical stirring. The resulting suspension is filtered, and the precipitate obtained in this way is dried in air. 60 g of a brown solid is recovered. Yield: 92%. A $^1$H NMR analysis of this solid shows that it is 60% constituted by giant calixarenes.

d) By Reaction of 4-(Methoxy)Phenol with a Base and Formaldehyde in Water and Retention of the Water then Heat Treatment of the Solid Precursor in the Form of a Brittle Resin, not Isolated, in Octane Under Reflux.

A 2-liter three-necked flask equipped with a mechanical stirrer and "Dean-Stark"-type water trap is loaded with a suspension of 65 g of 4-(methoxy)phenol (0.523 mol), 12 g of KOH (0.214 mol) and 100 ml of a 37% formaldehyde solution (1.34 mol). After 20 minutes of reflux, a bright yellow clear solution is obtained. Reflux is continued for 2 h, at the end of which period of time a yellow precipitate appears. 400 ml of octane is then added, and reflux is continued with stirring for 1 h, at the end of which period of time the reaction medium solidifies. The reaction medium is neutralized with 50 ml of 37% hydrochloric acid in solution in 1 liter of methanol, under vigorous mechanical stirring. The resulting suspension is filtered, and the precipitate obtained in this way is dried in air. 60 g of a brown solid is recovered. Yield: 92%. A $^1$H NMR analysis of this solid shows that it is 80% constituted by giant calixarenes.

e) By Reaction of 4-(Methoxy)Phenol with a Base and Formaldehyde in Water and Retention of the Water then Heat Treatment of the Solid Precursor in the Form of a Brittle Resin, not Isolated, in Xylene or Toluene Under Reflux.

A 2-liter three-necked flask equipped with a mechanical stirrer and "Dean-Stark"-type water trap is loaded with a suspension of 65 g of 4-(methoxy)phenol (0.523 mol), 12 g of KOH (0.214 mol) and 100 ml of a 37% formaldehyde solution (1.34 mol). After 20 minutes of reflux, a bright yellow clear solution is obtained. Reflux is continued for 2 h, at the end of which period of time a yellow precipitate appears. 400 ml of xylene is then added, and reflux is continued with stirring for 1 h, at the end of which period of time the reaction medium solidifies. The reaction medium is neutralized with 50 ml of 37% hydrochloric acid in solution in 1 liter of methanol, under vigorous mechanical stirring. The resulting suspension is filtered, and the precipitate obtained in this way is dried in air. 60 g of a brown solid is recovered. Yield: 92%. A $^1$H NMR analysis of this solid shows that it is 80% constituted by giant calixarenes.

f) By Heat Treatment of the Dimer of 4-(methoxy)phenol, Isolated, in Octane Under Reflux.

A 2-liter three-necked flask equipped with a mechanical stirrer and "Dean-Stark"-type water trap is loaded with a suspension of 65 g of 4-(methoxy)phenol (0.523 mol), 10.08 g of LiOH.H$_2$O (0.214 mol) and 100 ml of a 37% formaldehyde solution (1.34 mol). After 20 minutes of reflux, a bright yellow clear solution is obtained.

While still maintaining reflux, a strong stream of argon is then established inside the flask, with the aim of removing the water. The initially very fluid reaction medium becomes more and more viscous, until it completely solidifies into a brittle solid with a yellow colour.

A $^1$H NMR analysis of this solid shows that it is constituted almost exclusively by the phenolic dimer.

The reaction medium is then neutralized with an HCl/methanol mixture, under vigorous stirring.

After filtration and washing with water, a white solid is recovered quantitatively.

All of the solid thus recovered is placed in a 1-liter two-necked flask. A solution of KOH (13.2 g) in 150 ml of methanol is added with mechanical stirring, under argon. At the end of 8 h, the methanol is evaporated off using a vane pump. 400 ml of octane is then added to the yellow solid obtained in this way. After fixing a water trap of the "Dean-Stark" type onto one of the ground glass necks, the medium is taken to reflux for 4 h. NMR monitoring of the reaction shows the evolution of the composition of the reaction medium towards the formation of giant calixarenes. Final proportion: 80%.

g) By Heat Treatment of the Dimer of 4-(methoxy)phenol, Isolated, in Xylene or Toluene Under Reflux.

A 2-liter three-necked flask equipped with a mechanical stirrer and "Dean-Stark"-type water trap is loaded with a suspension of 65 g of 4-(methoxy)phenol (0.523 mol), 10.08 g of LiOH.H$_2$O (0.214 mol) and 100 ml of a 37% formaldehyde solution (1.34 mol). After 20 minutes of reflux, a bright yellow clear solution is obtained.

While still maintaining reflux, a strong stream of argon is then established inside the flask, with the aim of removing the water. The initially very fluid reaction medium becomes more and more viscous, until it completely solidifies into a brittle solid with a yellow colour.

A $^1$H NMR analysis of this solid shows that it is constituted almost exclusively by the phenolic dimer.

The reaction medium is then neutralized with a HCl/methanol mixture, under vigorous stirring.

After filtration and washing with water, a white solid is recovered quantitatively.

All of the solid thus recovered is placed in a 1-liter two-necked flask. A solution of KOH (13.2 g) in 150 ml of methanol is added with mechanical stirring, under argon. At the end of 8 h, the methanol is evaporated off using a vane pump. 400 ml of xylene is then added to the yellow solid obtained in this way. After fixing a water trap of the "Dean-Stark" type onto one of the ground glass necks, the medium is taken to reflux for 4 h. NMR monitoring of the reaction shows the evolution of the composition of the reaction medium towards the formation of giant calixarenes. Final proportion: 50%.

h) By Reaction of 4-(Methoxy)Phenol with a Base and Formaldehyde in Water and an Organic Solvent (without Removal of the Water).

A 2-liter three-necked flask equipped with a mechanical stirrer and "Dean-Stark"-type water trap is loaded with a suspension of 65 g of 4-(methoxy)phenol (0.523 mol), 12 g of KOH (0.214 mol), 100 ml of a 37% formaldehyde solution (1.34 mol) and 800 ml of xylene. The yellow emulsion obtained in this way is taken to reflux for 5 h.

An NMR analysis shows that the reaction medium contains 70% of giant calixarenes.

Example 2.2: Preparation of p-(methyl)calixarenes a) By Reaction of 4-(methyl)phenol with a Base and Formaldehyde in Water and Removal. Solid Precursor in the Form of a Brittle Resin, Isolated.

A 2-liter three-necked flask equipped with a mechanical stirrer and "Dean-Stark"-type water trap is loaded with a solution of 55 g of p-cresol (0.5 mol), 12 g of KOH (0.214 mol) and 100 ml of a 37% formaldehyde solution (1.34 mol). After 20 minutes of reflux, a clear pale yellow solution is obtained.

While still maintaining reflux, a strong stream of argon is then established inside the flask, with the aim of removing the water. (double space) The initially very fluid reaction medium becomes more and more viscous, until it completely solidifies into a brittle solid with a pale yellow colour. A proton NMR analysis shows that this solid is 30% constituted by giant calixarenes b) By Reaction of 4-(methyl)phenol with a Base and Formaldehyde in Water and Removal of the Water then Heat Treatment of the Solid Precursor in the Form of a Brittle Resin, not Isolated, in Octane Under Reflux.

A 2-liter three-necked flask equipped with a mechanical stirrer and "Dean-Stark"-type water trap is loaded with a solution of 55 g of p-cresol (0.5 mol), 12 g of KOH (0.214 mol) and 100 ml of a 37% formaldehyde solution (1.34 mol). After 20 minutes of reflux, a clear pale yellow solution is obtained.

While still maintaining reflux, a strong stream of argon is then established inside the flask, with the aim of removing the water. The initially very fluid reaction medium becomes more and more viscous, until it completely solidifies into a brittle solid with a pale yellow colour.

After returning to ambient temperature, 400 ml of octane is then added. The heterogeneous reaction medium obtained in this way is then taken to reflux without stirring. Monitoring the reaction then shows an evolution of the composition towards the formation of giant calixarenes.

At the end of 6 h of reflux, 50 ml of 37% hydrochloric acid is added, as well as one liter of methanol, under vigorous mechanical stirring. The resulting suspension is filtered, and the precipitate obtained in this way is dried in air. 40 g of a powdery solid is recovered. Yield: 72%.

c) By Reaction of 4-(methyl)phenol with a Base and Formaldehyde in Water and Removal of the Water then Heat Treatment of the Solid Precursor in the Form of a Brittle Resin, is not Isolated, in Xylene or Toluene Under Reflux.

A 2-liter three-necked flask equipped with a mechanical stirrer and "Dean-Stark"-type water trap is loaded with a solution of 55 g of p-cresol (0.51 mol), 12 g of KOH (0.214 mol) and 100 ml of a 37% formaldehyde solution (1.34 mol). After 20 minutes of reflux, a clear pale yellow solution is obtained.

While still maintaining reflux, a strong stream of argon is then established inside the flask, with the aim of removing the water. The initially very fluid reaction medium becomes more and more viscous, until it completely solidifies into a brittle solid with a pale yellow colour.

After returning to ambient temperature, 400 ml of xylene is then added. The reaction medium is then taken to reflux under stirring.

At the end of 6 h of reflux, 50 ml of 37% hydrochloric acid is added, as well as one liter of methanol, under vigorous mechanical stirring. The resulting suspension is filtered, and the precipitate obtained in this way is dried in air. An analysis of the reaction medium by proton NMR shows that it is 30% constituted by giant calixarenes.

d) By Reaction of 4-(methyl)phenol with a Base and Formaldehyde in Water and Retention of the Water then Heat Treatment of the Solid Precursor in the Form of a Brittle Resin, not Isolated, in Octane Under Reflux.

A 2-liter three-necked flask equipped with a mechanical stirrer and "Dean-Stark"-type water trap is loaded with a suspension of 55 g of p-cresol (0.5 mol) (0.51 mol), 12 g of KOH (0.214 mol) and 100 ml of a 37% formaldehyde solution (1.34 mol). After 20 minutes of reflux, a bright yellow clear solution is obtained. Reflux is continued for 2 h, at the end of which period of time a yellow precipitate appears. 400 ml of octane is then added, and reflux is continued with stirring for 1 h, at the end of which period of time the reaction medium solidifies. The reaction medium is neutralized with 50 ml of 37% hydrochloric acid in solution in 1 liter of methanol, under vigorous mechanical stirring. The resulting suspension is filtered, the precipitate is washed with water, and dried in air. A $^1$H NMR analysis of this solid shows that it is 80% constituted by giant calixarenes.

e) By Reaction of 4-(methyl)phenol with a Base and Formaldehyde in Water and Retention of the Water then Heat Treatment of the Solid Precursor in the Form of a Brittle Resin, not Isolated, in Xylene or Toluene Under Reflux.

A 2-liter three-necked flask equipped with a mechanical stirrer and "Dean-Stark"-type water trap is loaded with a suspension of 55 g of p-cresol (0.5 mol), 12 g of KOH (0.214 mol) and 100 ml of a 37% formaldehyde solution (1.34 mol). After 20 minutes of reflux, a bright yellow clear solution is obtained. Reflux is continued for 2 h, at the end of which period of time a yellow precipitate appears. 400 ml of xylene is then added, and reflux is continued with stirring for 1 h, at the end of which period of time the reaction medium solidifies. The reaction medium is neutralized with 50 ml of 37% hydrochloric acid in solution in 1 liter of methanol, under vigorous mechanical stirring. The resulting suspension is filtered, the precipitate is washed with water, and dried in air. An analysis by $^1$H NMR of this solid shows that it is 80% constituted by giant calixarenes.

f) By Heat Treatment of the Dimer of 4-(methyl)phenol, Isolated, in Octane Under Reflux.

A 2-liter three-necked flask equipped with a mechanical stirrer and "Dean-Stark"-type water trap is loaded with a suspension of 55 g of 4-(methyl)phenol (0.5 mol), 10.08 g of LiOH.H$_2$O (0.214 mol) and 100 ml of a 37% formaldehyde solution (1.34 mol). After 20 minutes of reflux, a bright yellow clear solution is obtained.

While still maintaining reflux, a strong stream of argon is then established inside the flask, with the aim of removing the water. The initially very fluid reaction medium becomes more and more viscous, until it completely solidifies into a brittle solid with a yellow colour.

A $^1$H NMR analysis of this solid shows that it is constituted almost exclusively by the phenolic dimer.

The reaction medium is then neutralized with a HCl/methanol mixture, under vigorous stirring.

After filtration and washing with water, a white solid is recovered quantitatively.

All of the solid thus recovered is placed in a 1-liter two-necked flask. A solution of KOH (12 g) in 150 ml of methanol is added with mechanical stirring, under argon. At the end of 8 h, the methanol is evaporated off using a vane pump. 400 ml of octane is then added to the yellow solid obtained in this way. After fixing a water trap of the "Dean-Stark" type onto one of the ground glass necks, the medium is taken to reflux for 4 h. NMR monitoring of the reaction shows the evolution of the composition of the reaction medium towards the formation of giant calixarenes. Final proportion: 50%.

g) By Heat Treatment of the Dimer of 4-(methyl)phenol, Isolated, in Xylene or Toluene Under Reflux.

A 2-liter three-necked flask equipped with a mechanical stirrer and "Dean-Stark"-type water trap is loaded with a suspension of 55 g of 4-(methyl)phenol (0.5 mol), 10.08 g of LiOH.H$_2$O (0.214 mol) and 100 ml of a 37% formaldehyde solution (1.34 mol). After 20 minutes of reflux, a bright yellow clear solution is obtained.

While still maintaining reflux, a strong stream of argon is then established inside the flask, with the aim of removing the water. The initially very fluid reaction medium becomes more and more viscous, until it completely solidifies into a brittle solid with a yellow colour.

A $^1$H NMR analysis of this solid shows that it is constituted almost exclusively by the phenolic dimer.

The reaction medium is then neutralized with a HCl/methanol mixture, under vigorous stirring. After filtration and washing with water, a white solid is recovered quantitatively.

All of the solid thus recovered is placed in a 1-liter two-necked flask. A solution of KOH (12 g) in 150 ml of methanol is added with mechanical stirring, under argon. At the end of 8 h, the methanol is evaporated off using a vane pump. 400 ml of xylene is then added to the yellow solid obtained in this way. After fixing a water trap of the "Dean-Stark" type onto one of the ground glass necks, the medium is taken to reflux for 4 h. NMR monitoring of the reaction shows the evolution of the composition of the reaction medium towards the formation of giant calixarenes. Final proportion: 50%.

h) By Reaction of 4-(methyl)phenol with a Base and Formaldehyde in Water and an Organic Solvent (without Removal of Water).

A 2-liter three-necked flask equipped with a mechanical stirrer and "Dean-Stark"-type water trap is loaded with a suspension of 55 g of p-cresol (0.5 mol), 12 g of KOH (0.214 mol), 100 ml of a 37% formaldehyde solution (1.34 mol) and 800 ml of xylene. The yellow emulsion obtained in this way is taken to reflux for 5 h.

An NMR analysis shows that the reaction medium contains 70% of giant calixarenes.

Example 2.3: Preparation of p-(ethyl)calixarenes

A 2-liter three-necked flask equipped with a mechanical stirrer, a Dean-Stark trap and a condenser as well as heating using an oil bath, is loaded with 61.04 g of 4-(ethyl)phenol (0.5 mol) and 135 ml of formaldehyde in an aqueous solution at 30%.

The resulting suspension is heated at 140° C. under the protection of argon.

A solution of 12 g of KOH (0.214 mol; 0.43 equivalent) in 10 ml of water is rapidly injected at 90° C., while continuing heating. The white suspension transforms into a bright yellow clear solution. This solution is maintained under reflux for 1 h.

One of the ground glass necks of the flask is then equipped with a swan-neck connected to a bubbler, and the solution is then subjected to vigorous flushing with argon (20 bubbles/s), the argon inlet being via the top of the condenser.

At the end of approximately 40 min of flushing, the initially clear and fluid solution becomes more and more viscous, and finally solidifies at the end of 1 h.

600 ml of xylene is then added to this solid, and the resulting suspension is taken to reflux under vigorous mechanical stirring, so as to thoroughly redisperse the solid precursor during this period of time.

After neutralization with a mixture of 500 ml of THF/50 ml of 37% HCl under vigorous stirring and filtration, a white solid is recovered 60% constituted by giant calixarenes ($^1$H NMR analysis).

Example 2.4: Preparation of p-(benzyl)calixarenes

A 2-liter three-necked flask equipped with a mechanical stirrer, a Dean-Stark trap and a condenser as well as heating using an oil bath, is loaded with 92.12 g of 4-(benzyl)phenol (0.5 mol) and 135 ml of formaldehyde in an aqueous solution at 30%.

The resulting suspension is heated at 140° C. under the protection of argon.

A solution of 12 g of KOH (0.214 mol; 0.43 equivalent) in 10 ml of water is rapidly injected at 90° C., while continuing heating. The white suspension transforms into a bright yellow clear solution. This solution is maintained under reflux for 1 h.

One of the ground glass necks of the flask is then equipped with a swan-neck connected to a bubbler, and the solution is then subjected to vigorous flushing with argon (20 bubbles/s), the argon inlet being via the top of the condenser.

At the end of approximately 40 min of flushing, the initially clear and fluid solution becomes more and more viscous, and finally solidifies at the end of 1 h.

600 ml of xylene is then added to this solid, and the resulting suspension is taken to reflux under vigorous mechanical stirring, so as to thoroughly redisperse the solid precursor during this time. After neutralization with a mixture of 500 ml of THF/50 ml of 37% HCl under vigorous stirring and filtration, a white solid is recovered 65% constituted by giant calixarenes ($^1$H NMR analysis).

Example 2.5: Preparation of p-(dibenzylamino)calixarenes

A 2-liter three-necked flask equipped with a mechanical stirrer, a Dean-Stark trap and a condenser as well as heating using an oil bath, is loaded with 150.66 g of 4-(dibenzylamino)phenol (0.5 mol) and 135 ml of formaldehyde in an aqueous solution at 30%.

The resulting suspension is heated at 140° C. under the protection of argon.

A solution of 12 g of KOH (0.214 mol; 0.43 equivalent) in 10 ml of water is rapidly injected at 90° C., while continuing heating. The white suspension transforms into a bright yellow clear solution. This solution is maintained under reflux for 1 h.

One of the ground glass necks of the flask is then equipped with a swan-neck connected to a bubbler, and the solution is then subjected to vigorous flushing with argon (20 bubbles/s), the argon inlet being via the top of the condenser.

At the end of approximately 40 min of flushing, the initially clear and fluid solution becomes more and more viscous, and finally solidifies at the end of 1 h.

600 ml of xylene is then added to this solid, and the resulting suspension is taken to reflux under vigorous mechanical stirring, so as to thoroughly redisperse the solid precursor during this time. After neutralization with a mixture of 500 ml of THF/50 ml of 37% HCl under vigorous stirring and filtration, a white solid is recovered 55% constituted by giant calixarenes ($^1$H NMR analysis).

Example 2.5: Preparation of p-(methyl)calixarenes in the Presence of CsOH (0.4 Equivalent)

A 2-liter three-necked flask equipped with a mechanical stirrer and "Dean-Stark"-type water trap is loaded with a suspension of 54.03 g (0.52 mol) of 4-(methyl)phenol (p-cresol), 36 ml of a solution of CsOH at 50% (0.208 mol) and 100 ml of a 37% formaldehyde solution (1.34 mol). After 20 minutes of reflux, a bright yellow clear solution is obtained.

While still maintaining reflux, a strong stream of argon is then established inside the flask, with the aim of removing the water. The initially very fluid reaction medium becomes more and more viscous, until it completely solidifies into a brittle solid with a yellow colour.

After returning to ambient temperature, 200 ml of xylene is then added. The suspension obtained in this way is then taken to reflux under stirring. Monitoring the reaction then shows an evolution of the composition towards the formation of giant calixarenes.

At the end of 2 h of reflux, 50 ml of 37% hydrochloric acid is added, as well as 500 ml of tetrahydrofuran, under vigorous mechanical stirring. The resulting suspension is evaporated to dryness. A $^1$H NMR analysis shows that this solid is 50% constituted by giant calixarenes.

B) Examples of the Functionalization of Giant Calixarenes

Pegylation (PEG2) of the Low Crown of a Giant Calixarene (KOH 0.4 Equivalent without Stirring, Number of Phenolic Units at Peak=60)

1 g of giant calixarenes and 5 mL of 2-(2-ethoxyethoxy) ethyl bromide are introduced into a 25 mL three-necked flask under argon. Heating is carried out at 60° C. and a suspension of 377.4 mg of sodium hydride (60% in paraffin, 9.43 mmol, 2 equivalent by phenol) in 5 mL of DMF is introduced slowly under vigorous stirring. After a night at 60° C., the reaction medium is cooled down to ambient temperature and 50 mL of methanol is added, followed by filtering and rinsing the solid with water then with methanol. The solid is placed under stirring in 50 mL of acetonitrile for 2 h then filtered and dried under vacuum. 1.41 g (η=91%) of an orange-coloured solid is obtained which is solubilized hot in DMSO. 1H NMR (DMSO-d$_6$, 50° C., δ, ppm): 7.22 (s, 5H, aromatics); 6.54 (s, 2H, hydroquinones); 4.83 (s, 2H, benzyl methylenes); 4.05 (s, 2H, PEG); 3.85 (s, 2H, bridging methylenes); 3.69 (s, 2H, PEG); 3.54 (s, 2H, PEG); 3.44 (s, 2H, PEG); 3.36 (m, 2H, PEG), 1.01 (s, 3H, PEG).

Acetylation of the Low Crown of a Giant Calixarene (Number of Phenolic Units at Peak=60)

0.6 g of calixarene, 1.6 mL of ethyl bromoacetate, 3.91 g of potassium carbonate (2.61 mmol, 80 equivalent by phenol), 100 mg of tetrabutylammonium sulphate (0.29 mmol) and 5 mL of acetonitrile are introduced into a 10 mL three-necked flask. Heating is carried out at 75° C. overnight and 50 mL of methanol is added. Filtering is carried out followed by rinsing with water then with methanol. The solid obtained is dried under vacuum (787 mg, η=91%). 1H NMR (DMSO-d$_6$, δ, ppm): 7.22 (s, 5H, aromatics); 6.52 (s, 2H, hydroquinones); 4.80 (s, 2H, benzyl methylene); 4.29 (s, 2H, methylene in the alpha position of the carbonyl); 4.05 (m, 2H, methylene function ethyl); 3.96 (s, 2H, bridging methylene); 1.11 (s, 3H, methyl).

Example C)

Use of Giant Calixarenes for the Synthesis of Nanomaterials: Star Polymers

The procedure used is in two stages. During the first stage, the phenolic groups of calixarene are acylated with bromopropionyl bromide. These groups constitute polymerization initiators, used during a second stage for the growth of polystyrene chains.

Synthesis of the initiator for calix[50]arene.

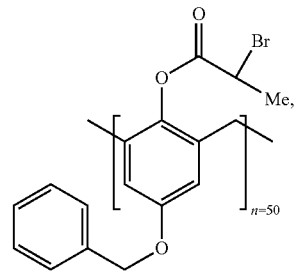

The giant calixarene (500 mg, 0.0002 mol) is introduced into a Schlenk tube. 5 mL of DMF and 1.5 mL of Et$_3$N are then added under argon. The system is immersed in an ice bath. Then 300 μL of bromopropionyl bromide is introduced. The solution is stirred for 1 h. Precipitation is carried out from 50 mL of MeOH, followed by filtering under vacuum. The initiator is solubilized in a few milliliters of THF. Then a second precipitation is carried out with 50 mL of MeOH, followed by filtering under vacuum. The product is dried in a desiccator.

yield=60%.

$^1$H NMR (350 MHz, CDCl$_3$) δ$_{ppm}$: 7.1-7.6 (m, 60H, —OCH$_2$—Ar), 6.8-6.4 (m, 24H, Ar), 5.1-4.7 (m, 24H, —OCH$_2$—Ar—), 4-3.5 (m, 24H, —Ar(phenol)-CH$_2$—), 3-1.5 (m, 24H, CH$_3$—CH(COR)—Br), 2-1.5 (m, 36H, CH$_3$—CH(COR)—Br).

This macroinitiator is also characterized by size exclusion chromatography (FIG. 24).

Synthesis of Star Polymer by Atom Transfer Radical Polymerization (ATRP)

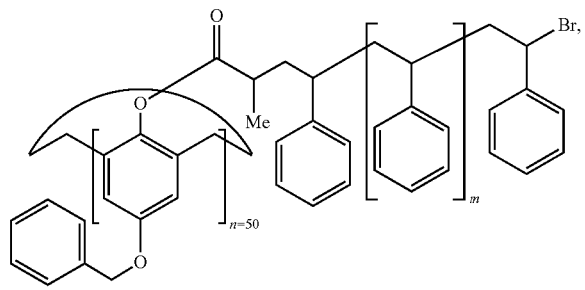

CuBr (25 mg, 0.00017 mol), bipyridine (80 mg, 0.00052 mol), the previously synthesized initiator (60 mg, 0.00017 mol) and 2 mL of styrene are introduced into a Schlenk tube under argon. The reaction medium is degassed using 3 freeze-thaw cycles. The Schlenk tube is immersed in an oil bath heated at 100° C. for a given time. The mixture is solubilized in THF. The mixture is filtered on a column of basic $Al_2O_3$. The polymer is precipitated from MeOH (with a $$\text{ratio} = \frac{THF}{MeOH} - 10),$$

then filtered under vacuum and rinsed with MeOH. The product is dried in a desiccator.

Yield=50%.

$^1$H NMR (360 MHz, $CDCl_3$) $\delta_{ppm}$: 7.1-7.6 (m, 5H, —$OCH_2$—Ar), 7.2-6.9 (m, 5H, $Ar_{styrene}$), 7.2-6.9 (m, 1H, —$CH_2$—CH(Ar)—$CH_2$—), 6.8-6.4 (m, 2H, Ar), 2.1-1.6 (m, 2H, —CH—$CH_2$—CH—), 2.1-1.6 (m, 1H, $HO_2C$—CH($CH_3$)—$CH_2$—), 1.6-1.3 (m, 3H, $CH_3$—CH—).

The star polymers obtained, which differ by the duration of the ATRP, are also characterized by size exclusion chromatography (FIG. 25).

Study of the Structure of the Polymers in Solution.

In order to study the behaviour of said star polymers in solution, a scaling law can be used:

$$Rh = KM^\alpha$$

where Rh corresponds to the hydrodynamic radius, M corresponds to the molar mass; K and $\alpha$ are coefficients. The terms K and $\alpha$ are constants which vary with the polymer.

$$\log Rh = \log K + \alpha \log M$$

The term $\alpha$ provides information on the behaviour of polymer in solution:

If $\alpha$ tends towards 1 then the polymer behaves as a linear polymer.

If $\alpha$ tends towards 0.5 then the polymer behaves as a random coil.

If $\alpha$ tends towards 0 then polymer behaves as a hard sphere.

The curve of the hydrodynamic radius (measured by light scattering) as a function of the molar mass (obtained by measuring the molar mass of the polystyrene branches (after "detaching" the central calixarene core by saponification) therefore make it possible to provide information on the structure of these nanoobjects in solution (FIG. 26).

In the case of said star polymers originating from calix[50]arene, the alpha exponent tends to 0 ("hard sphere"-type behaviour in solution). The giant calixarenes therefore exhibit specific "hard sphere"-type hydrodynamic behaviour, and therefore form well-defined nanoobjects in solution (THF), which are potentially useful for encapsulation and vectorization.

Example 3: Comparative Examples: Production of Small p-(benzyloxy)calixarenes with CsOH<0.5 Eq and Xylene Example A: Production of a Compound Consisting of p-(benzyloxy)calix[6]arene or of p-(benzyloxy)calix[7]arene in the Form of Caesium Salt or Neutralized or of a Mixture Comprising p-(benzyloxy)calix[6]arene and p-(benzyloxy)calix[7]arene with Caesium Hydroxide Example A.1: Concentration of Caesium Hydroxide of 0.15 Equivalent A suspension of 50.6 g of p-(benzyloxy)phenol (0.254 mol), 20 g (0.667 mol) of paraformaldehyde (melting point: 135° C.) in 700 ml of xylene is placed under argon in a 2-liter three-necked flask equipped with a mechanical stirrer and a "Dean-Stark" type water trap.

The suspension heated with stirring. When the temperature reaches 90° C., 7.4 ml (0.0425 mol) of a solution of CsOH at 50% (by weight) in water is added rapidly using a syringe (and under flushing with argon).

The suspension is left under reflux for 6 h, during which period of time the formation of a voluminous white precipitate is observed.

This precipitate is filtered, washed with xylene, then with pentane. M=35 g, yield of p-(benzyloxy)calix[7]arene (in the form of caesium monosalt): 58%

The spectroscopic characteristics of this precipitate correspond to that of a monoanion of p-(benzyloxy)calix[7]arene.

$^1$H NMR (DMSO-$d_6$): (chemical shifts, ppm) 7.60-7.20 (multiplet, aromatics); 6.72 (fine singlet, hydroquinone); 4.93 (fine singlet, benzyl protons); 3.71 (fine singlet, intracyclic methylenes). Mass spectrometry (MALDI, DHB matrix): m/z=1617.41 $(M+Cs)^+$.

A sample of 1 g of this precipitate is placed in suspension in 5 ml of dichloromethane, then neutralized with a concentrated aqueous solution of HCl, under vigorous stirring for 24 h.

The organic phase is recovered, then evaporated to dryness in a rotary evaporator.

0.91 g of a white solid is recovered, the spectroscopic characteristics of which are perfectly consistent with neutral p-(benzyloxy)calix[7]arene.

$^1$H NMR (DMSO-$d_6$): (chemical shifts, ppm) 7.30 (broad multiplet, aromatics); 6.62 (fine singlet, hydroquinone); 4.84 (fine singlet, benzyl protons); 3.74 (fine singlet, intracyclic methylenes).

Mass spectrometry (MALDI, DHB matrix): m/z=1507.65 $(M+Na)^+$.

The loss of mass observed (90 mg) is completely consistent with that expected for neutralization of a caesium monosalt: p-(benzyloxy)calix[7]arene$^-$.$Cs^+ \rightarrow$p-(benzyloxy)calix[7]arene.

Example A.2: Concentration of Caesium Hydroxide of 0.3 Equivalent

A suspension of 50.6 g of p-(benzyloxy)phenol (0.254 mol), 20 g (0.667 mol) of paraformaldehyde (melting point: 135° C.) in 700 ml of xylene is placed under argon in a 2-liter three-necked flask equipped with a mechanical stirrer and a "Dean-Stark" type water trap. The suspension is heated with stirring. When the temperature reaches 90° C., 14.8 ml (0.085 mol) of a solution of CsOH at 50% (by weight) in water is added rapidly using a syringe (and under flushing with argon).

The suspension is left under reflux for 5 h 30. Then a perfectly clear bright orange solution is obtained.

100 ml of a solution of 37% HCl in water is then added, and the formation of a precipitate is observed. The suspension is left under vigorous stirring for two days, then evaporated to dryness in a rotavapor.

After washing with 500 ml of water (removal of the salts and excess HCl), the solid is dissolved hot (130° C.) in 200 ml of DMSO. Then a clear solution black is obtained, to which 2 l of acetone is added hot.

After returning to ambient temperature, this clear solution is left for a week, during which a crystalline precipitate of p-(benzyloxy)calix[6]arene (18 g) is deposited on the walls of flask.

The filtrate is evaporated in a rotary evaporator, then with a heat gun until a black solid is obtained. This solid is washed with acetone, which leads to the recovery of a second batch of p-(benzyloxy)calix[6]arene (10 g). Total: 28 g, yield 51%.

$^1$H NMR (DMSO-d$_6$): (chemical shifts, ppm) 7.30 (broad multiplet, aromatics); 6.62 (fine singlet, hydroquinones); 4.79 (fine singlet, benzyl protons); 3.72 (fine singlet, intracyclic methylenes).

Mass spectrometry (MALDI, DHB matrix): m/z=1295.49 (M+Na)$^+$.

Production of a Compound Consisting of p-(benzyloxy) calix[6]arene or p-(benzyloxy)calix[7]arene in Neutralized Form or p-(benzyloxy)calix[8]arene or a Mixture Comprising p-(benzyloxy)calix[6]arene, p-(benzyloxy)calix[7]arene and p-(benzyloxy)calix[8]arene with Sodium or Potassium Hydroxide.

Example B.1: Concentration of Sodium or Potassium Hydroxide of 0.15 Equivalent A suspension of 34.5 g of p-(benzyloxy)phenol (0.173 mol), 20 g (0.667 mol) of paraformaldehyde (melting point: 135° C.) in 450 ml of xylene is placed under argon in a 1-liter three-necked flask equipped with a mechanical stirrer and a "Dean-Stark" type water trap. The suspension is heated with stirring. When temperature reaches 95° C., a solution of 1.43 g (0.03 mol) of KOH in 6 ml of Millipore water is added rapidly using a syringe (and under flushing with argon). The immediate appearance of a yellow coloration is observed.

The reaction medium is taken to reflux for 3 h 30, during which period of time the formation of a copious white precipitate and a bright orange solution is observed.

After returning to ambient temperature, the precipitate is recovered by filtration, washed with 100 ml of xylene and 300 ml of pentane.

Analysis of this precipitate indicates that it is constituted by pure p-(benzyloxy)calix[7]arene. M=20 g, yield 54%.

Characterizations:

$^1$H NMR (DMSO-d$_6$): (chemical shifts, ppm) 7.30 (broad multiplet, aromatics); 6.62 (fine singlet, hydroquinone); 4.84 (fine singlet, benzyl protons); 3.74 (fine singlet, intracyclic methylenes). Mass spectrometry (MALDI, DHB matrix): m/z=1524.62 (M+K)$^+$.

Example B.2: Concentration of Sodium or Potassium Hydroxide of 0.3 Equivalent A suspension of 51.5 g of p-(benzyloxy)phenol (0.258 mol), 20 g (0.667 mol) of paraformaldehyde (melting point: 135° C.) in 700 ml of xylene is placed under argon in a 2-liter three-necked flask equipped with a mechanical stirrer and a "Dean-Stark" type water trap.

The suspension is heated with stirring. When the temperature reaches 90° C., 3.056 g of NaOH (0.0764 mol) in 10 ml of water is added rapidly using a syringe (and under flushing with argon).

The suspension is left under reflux for 4 h30, a period at the end of which the reaction medium solidifies.

After returning to ambient temperature, the reaction medium is neutralized with 500 ml of a 2M HCl solution, under very vigorous stirring.

The resulting emulsion is evaporated to dryness and washed with 500 ml of water (removal of the sodium salts).

The resulting orange solid is washed with 500 ml of THF and the resulting white precipitate is filtered, which leads to the recovery of 20 g of pure p-(benzyloxy)calix[8]arene. Yield: 36.6%.

$^1$H NMR (DMSO-d$_6$): (chemical shifts, ppm) 7.30 (broad multiplet, aromatics); 6.58 (fine singlet, hydroquinones); 4.80 (fine singlet, benzyl protons); 3.77 (fine singlet, intracyclic methylenes).

Mass spectrometry (MALDI, DHB matrix): m/z=1719.62 (M+Na)$^+$.

The corresponding filtrate is evaporated to dryness, and dissolves hot in 45 ml of DMSO, which leads to formation of a black homogeneous solution. 1 liter of toluene is added thereto, and the dark orange clear solution is placed in the freezer (−23° C.) for 1 week, which leads to the formation of a microcrystalline precipitate. This precipitate is filtered, and its analysis by $^1$H NMR shows that it is pure p-(benzyloxy)calix[6]arene; m=6.3 g, 11%.

$^1$H NMR (DMSO-d$_6$): (chemical shifts, ppm) 7.30 (broad multiplet, aromatics); 6.62 (fine singlet, hydroquinone); 4.79 (fine singlet, benzyl protons); 3.72 (fine singlet, intracyclic methylenes).

Mass spectrometry (MALDI, DHB matrix): m/z=1295.49 (M+Na)'.

The corresponding DMSO/toluene filtrate is evaporated until an orange-coloured liquid is obtained. After the addition of 1 liter of methanol and filtration, 28.5 g of pure p-(benzyloxy)calix[7]arene is recovered. Yield: 52%.

$^1$H NMR (DMSO-d6): (chemical shifts, ppm) 7.30 (broad multiplet, aromatics); 6.62 (fine singlet, hydroquinones); 4.84 (fine singlet, benzyl protons); 3.74 (fine singlet, intracyclic methylenes).

Mass spectrometry (MALDI, DHB matrix): m/z=1524.62 (M+K)$^+$.

Example 4: Comparative Example: Reaction of p-(t-butyl)phenol with a Base at <0.5 Eq in Water without Organic Solvent A 2-liter three-necked flask equipped with a mechanical stirrer, a Dean-Stark trap and a condenser as well as heating using an oil bath, is loaded with 100 g of 4-(tBu)phenol (0.666 mol) and 135 ml of 37% formaldehyde in an aqueous solution.

The resulting suspension is heated at 140° C. under the protection of argon.

A solution of 15 g of KOH (0.266 mol; 0.4 equivalent) in 10 ml of water is rapidly injected at 90° C., while continuing heating. The white suspension transforms into a bright yellow clear solution. This solution is maintained under reflux for 1 h.

One of the ground glass necks of the flask is then equipped with a swan-neck connected to a bubbler, and the solution is then subjected to vigorous flushing with argon (20 bubbles/s), the argon inlet being via the top of the condenser.

At the end of approximately 40 min of flushing, the initially clear and fluid solution becomes more and more viscous, and finally solidifies at the end of 1 h.

NMR analysis of this solid (DMSO-d6) is shown in FIG. 17.1.

This solid seems essentially constituted by p-(tBu)calix [8]arene, by comparison with the reference sample of this compound in DMSO-d6 (FIG. 17.2).

400 ml of toluene is then added to this solid, and the resulting suspension is taken to reflux without stirring for 2 h.

After neutralization with a mixture of 500 ml of THF/50 ml of 37% HCl under vigorous stirring, NMR analysis of this solid (CDCl$_3$, FIG. 18) shows that the product obtained comprises a significant proportion of p-(tBu)calix[4,6,8] arenes (comparison with authentic samples), as well as a high proportion of polymers (broad signals).

The characteristic evolution of the spectroscopic signature of the bridging methylenes of the large-sized calixarenes (9 to 16 repeat units) in CDCl$_3$ is not observed (C. D. Gutsche et al., JACS 1999).

Moreover, the presence of intense signals at 5 ppm indicates a high proportion of linear oligomers.

Example 5: Comparative Example: Preparation of a Mixture of p-benzyloxycalix[9-20]arenes with CsOH or RbOH (0.6 Eq)

A suspension of 50 g (0.25 mol) of 4-(benzyloxy)phenol and 18 g (0.6 mol) of paraformaldehyde in 700 ml of xylene is prepared under argon in a 2-liter two-necked flask equipped with a Dean-Stark trap and a condenser.

The suspension is heated under argon and vigorous magnetic stirring, and at 90° C. 26 ml of a solution of CsOH at 50% in water is added rapidly.

The reaction medium is taken to reflux for 6 h, during which period of time a clear orange-coloured solution is obtained.

An NMR analysis (DMSO-d6, FIG. 19) of this solution shows that it comprises approximately 60% of large calixarenes (identifiable by characteristic signals at 6.52 ppm).

This solution is neutralized by the addition of 200 ml of THF containing 20 ml of 37% HCl under vigorous stirring.

The resulting suspension is evaporated, and washed with 200 ml of acetonitrile (removal of the small calixarenes).

The resulting solid is dissolved in 1 liter of an acetone/DMSO mixture (90/10 by volume), filtered (removal of calix[8]arene) and left in a refrigerator (1° C.) for 4 days.

15 g of a microcrystalline solid is recovered.

This solid is constituted by a mixture of large calixarenes.

Its different constituents can be separated by a succession of recrystallizations/chromatographies using different solvents. The corresponding purification diagram is given in FIG. 20.

The invention claimed is:
1. Mixture of calixarenes of the following formula (IV):

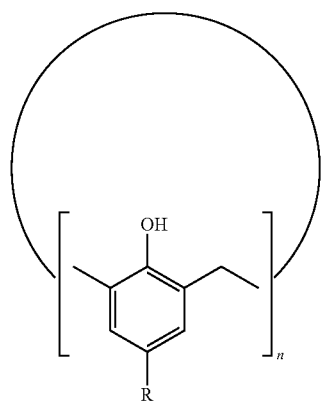

(IV)

in which n is an integer comprised from 21 to at most 220, and in which R is selected from the group consisting of:

a benzyloxy group optionally substituted in the ortho and/or para and/or meta position with one or more substituents selected from a halogen, SR' and OR', R' representing a linear or branched C$_1$-C$_{20}$ alkyl chain, a C$_3$ to C$_{20}$ cycloalkyl group, NR$_a$R$_b$, PR$_a$R$_b$, P(O)R$_a$R$_b$, P(O)OR$_a$OR$_b$, R$_a$ and R$_b$ representing, independently of one another, a linear or branched C$_1$-C$_{20}$ alkyl, a linear or branched C$_1$-C$_{20}$ alkyloxy group, a linear or branched PEG-1 to 10, the —OH end group of which is alkylated with a linear or branched C$_1$-C$_{20}$ alkyl, a benzyl thioether group —S—CH$_2$-Ph optionally substituted in the ortho and/or para and/or meta position with one or more substituents selected from a halogen, SR' and OR', NR$_a$R$_b$, PR$_a$R$_b$, P(O)R$_a$R$_b$, P(O)OR$_a$OR$_b$, R$_a$ and R$_b$ representing, independently of one another, a linear or branched C$_1$-C$_{20}$ alkyl, a linear or branched C$_1$-C$_{20}$ alkyl thioether group, of formula —S—(C$_1$-C$_{20}$-alkyl), an —NR$_a$R$_b$ group, R$_a$ and R$_b$ representing, independently of one another, a linear or branched C$_1$-C$_{20}$ alkyl, and a dibenzylamine group of formula —N(benzyl)$_2$, in which the two benzyl groups are, independently of one another, optionally substituted in the ortho and/or para and/or meta position with one or more substituents selected from a halogen, SR' and OR', R' representing a linear or branched C$_1$-C$_{20}$ alkyl chain, a C$_3$ to C$_{20}$ cycloalkyl group, NR$_a$R$_b$, PR$_a$R$_b$, P(O)R$_a$R$_b$, P(O)OR$_a$OR$_b$, R$_a$ and R$_b$ representing, independently of one another, a linear or branched C$_1$-C$_{20}$ alkyl.

2. A material comprising a mixture of giant p-(R)calixarenes the size of which is greater than 20, R being selected from the group consisting of:

a benzyloxy group optionally substituted in the ortho and/or para and/or meta position with one or more substituents selected from a halogen, SR' and OR', R' representing a linear or branched C$_1$-C$_{20}$ alkyl chain, a C$_3$ to C$_{20}$ cycloalkyl group, NR$_a$R$_b$, PR$_a$R$_b$, P(O)R$_a$R$_b$, P(O)OR$_a$OR$_b$, R$_a$ and R$_b$ representing, independently of one another, a linear or branched C$_1$-C$_{20}$ alkyl, a linear or branched C$_1$-C$_{20}$ alkyloxy group, a linear or branched PEG-1 to 10, the —OH end group of which is alkylated with a linear or branched C$_1$-C$_{20}$ alkyl, a benzyl thioether group —S—CH$_2$-Ph optionally substituted in the ortho and/or para and/or meta position with one or more substituents selected from a halogen, SR' and OR', NR$_a$R$_b$, PR$_a$R$_b$, P(O)R$_a$R$_b$, P(O)OR$_a$OR$_b$, R$_a$ and R$_b$ representing, independently of one another, a linear or branched C$_1$-C$_{20}$ alkyl, a linear or branched C$_1$-C$_{20}$ alkyl thioether group, of formula —S—(C$_1$-C$_{20}$-alkyl), an —NR$_a$R$_b$ group, R$_a$ and R$_b$ representing, independently of one another, a linear or branched C$_1$-C$_{20}$ alkyl, and a dibenzylamine group of formula —N(benzyl)$_2$, in which the two benzyl groups are, independently of one another, optionally substituted in the ortho and/or para and/or meta position with one or more substituents selected from a halogen, SR' and OR', R' representing a linear or branched C$_1$-C$_{20}$ alkyl chain, a C$_3$ to C$_{20}$ cycloalkyl group, NR$_a$R$_b$, PR$_a$R$_b$, P(O)R$_a$R$_b$, P(O)OR$_a$OR$_b$, R$_a$ and R$_b$ representing, independently of one another, a linear or branched C$_1$-C$_{20}$ alkyl, as the constitution of said material or in the context of reinforcement of materials.

3. A material comprising a mixture of calixarenes according to claim 1, as the constitution of as material or in the context of reinforcement of materials.

4. The mixture of calixarenes according to claim 1, wherein R is selected from the group consisting of:
   a benzyloxy group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl, and
   a linear or branched $C_1$-$C_{20}$ alkyloxy group, a linear or branched PEG-1 to 10, the —OH end group of which is alkylated with a linear or branched $C_1$-$C_{20}$ alkyl.

5. The mixture of calixarenes according to claim 4, wherein R is selected from the group consisting of:
   a benzyloxy group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_5$-$C_{20}$ alkyl, and
   a linear or branched $C_5$-$C_{20}$ alkyloxy group, a linear or branched PEG-1 to 10, the —OH end group of which is alkylated with a linear or branched $C_5$-$C_{20}$ alkyl.

6. The mixture of calixarenes according to claim 1, wherein R is an octyloxy group, using GPC a peak molar mass corresponding to 35 phenolic units.

7. The mixture of calixarenes according to claim 1, wherein R is a benzyloxy group and average size determined by the centred Gaussian measure varies from 21 to approximately 212.

8. The material according to claim 2, wherein in which said mixture further comprises a p-(R)calix[7]arene and/or a p-(R)calix[8]arene.

9. The material according to claim 3, wherein said mixture further comprises a p-(R)calix[7]arene and/or a p-(R)calix[8]arene.

10. The material according to claim 1 wherein R is selected from the group consisting of:
   a benzyloxy group optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl,
   a linear or branched $C_5$-$C_{20}$ alkyloxy group, a linear or branched PEG-1 to 10, the —OH end group of which is alkylated with a linear or branched $C_5$-$C_{20}$ alkyl,
   an —$NR_aR_b$ group, $R_a$ and $R_b$ representing, independently of one another, a linear or branched $C_1$-$C_{20}$ alkyl, and
   a dibenzylamine group of formula —$N(benzyl)_2$, in which the two benzyl groups are, independently of one another, optionally substituted in the ortho and/or para and/or meta position with one or more substituents selected from a halogen, SR' and OR', R' representing a linear or branched $C_1$-$C_{20}$ alkyl chain, a $C_3$ to $C_{20}$ cycloalkyl group, $NR_aR_b$, $PR_aR_b$, $P(O)R_aR_b$, $P(O)OR_aOR_b$, $R_a$ and $R_b$ representing, independently of one another, a linear or branched $C_1$-$C_{20}$ alkyl.

\* \* \* \* \*